(12) United States Patent
Xia et al.

(10) Patent No.: US 7,786,264 B2
(45) Date of Patent: Aug. 31, 2010

(54) MONOCLONAL ANTIBODY AGAINST HEPATITIS E VIRUS OR ITS FRAGMENT WITH BINDING ACTIVITY AND USE THEREOF

(75) Inventors: Ningshao Xia, Xiamen (CN); Jun Zhang, Xiamen (CN); Ying Gu, Xiamen (CN); Shaowei Li, Xiamen (CN); Shengxiang Ge, Xiamen (CN); Zhiqiang He, Xiamen (CN)

(73) Assignee: Beijing Wantai Biological Pharmacy Enterprise Co., Ltd, Haikou (CN)

( * ) Notice: Subject to any disclaimer, the term of this patent is extended or adjusted under 35 U.S.C. 154(b) by 870 days.

(21) Appl. No.: 10/495,091

(22) PCT Filed: Nov. 8, 2002

(86) PCT No.: PCT/CN02/00797

§ 371 (c)(1),
(2), (4) Date: Nov. 30, 2004

(87) PCT Pub. No.: WO03/040187

PCT Pub. Date: May 15, 2003

(65) Prior Publication Data

US 2006/0233822 A1    Oct. 19, 2006

(30) Foreign Application Priority Data

Nov. 8, 2001    (CN) ............................. 01 1 34643

(51) Int. Cl.
  *C12P 21/08*    (2006.01)
  *C17K 16/00*    (2006.01)
(52) U.S. Cl. ............... 530/387.1; 530/388.1; 530/388.8
(58) Field of Classification Search ...................... None
  See application file for complete search history.

(56) References Cited

U.S. PATENT DOCUMENTS

| 5,667,966 | A | 9/1997 | Paul et al. |
| 5,830,636 | A | 11/1998 | Paul et al. |
| 5,885,768 | A | 3/1999 | Reyes et al. |
| 6,291,641 | B1 | 9/2001 | Fuerst et al. |

FOREIGN PATENT DOCUMENTS

| CN | 1345775 A | 4/2002 |
| EP | 0671472 A1 | 9/1995 |
| JP | 7165799 A | 6/1995 |
| WO | WO-93/14116 A1 | 7/1993 |
| WO | WO-95/17501 A1 | 6/1995 |

OTHER PUBLICATIONS

Schofield et al. Identification by phage display and characterization of two neutralizing chimpanzee monoclonal antibodies to the hepatitis E virus capsid protein. J Virol. Jun. 2000;74(12):5548-55.*
Kashmiri S. et al. :SDR grafting-a new approach to antibody humanization Methods, 36 (2005) 25-34.*
Stuart Rudikoff, et al. "Single Amino Acid Substitution Altering Antigen-Binding Specificity" PNAS 1982 79: 1979-1983.*
Krawczynski K et al. "Hepatitis E". Infect Dis Clin North Am. Sep. 2000;14(3):669-87. Review. Abstract only.*
Keller C et al "Passive immunity in prevention and treatment of infectious diseases". Clin Microbiol Rev. Oct. 2000;13(4):602-14. Review.*
J. Mol. Biol. 219(4), 603-604 (1991), Brady, R.I. et al., "Crystallization and preliminary X-ray diffraction study of a chimaeric Fab' fragment of antibdy binding tumour cells."
Proc. Natl. Acad. Sci. U.S.A. 71(4), 1123-1127(1974), Francis, S. H. et al., "Amino-acid sequence of the variable region of the heavy (alpha) chain of a mouse myeloma protein with anti-hapten activity."
Hybridoma 14(3), 217-223 (1995), Czerwinski, M. and Usnarska, "Molecular characterization of mouse monoclonal antibody BIII.136 and the epitope recognized by the antibody in human band 3 protein."
Proc. Natl. Acad. Sci. U.S.A. 91(3), 1089-1093 (1994), Bhat, T.N. et al., "Bound water molecules and conformational stablization help mediate an antigen-antibody association."
J. Exp. Med. 171(1), 265-292 (1990), Shlomchik, M. et al., "Anti-DNA antibodied from autoimmune mice arise by clonal expansion and somatic mutation."
GenBank LOCUS CAA07256 112a linear Jun. 6, 1998, immunoglobulin light chain, variable region [Mus musculus].

(Continued)

*Primary Examiner*—Bo Peng
(74) *Attorney, Agent, or Firm*—Blank Rome LLP

(57) ABSTRACT

The present invention relates to monoclonal antibody specifically binding to polypeptide(s) comprising the amino acid sequence as set forth in SEQ ID No. 1 of hepatitis E virus ORF 2 or its conserved variants or its active fragments, or other monoclonal antibodies against ORF2 which can cross react with said monoclonal antibody of present invention, and its nucleotide sequence or its degenerate sequence; to the antigenic determinant in hepatitis E virus ORF2; to a method for screening isolated or recombined polypeptide or polypeptide analog, which has the same property of specifically binding said monoclonal antibody 8C11 and/or 8H3 as said antigenic determinant 1) or 3) of hepatitis E virus ORF2; to polypeptide or polypeptide analog screened by the method above and its nucleotide sequence or degenerate sequence; to a use of said polypeptide or polypeptide analog in preparation of a medicament for the diagnosis and/or precaution of hepatitis E virus infection; to a diagnostic kit for hepatitis E virus infection and a vaccine composition for prophylaxis of hepatitis E virus infection; to use of said monoclonal antibodies or their active fragments or conserved variants in preparation of a medicament for diagnosis, prophylaxis and/or treatment of hepatitis E virus infection; to pharmaceutical composition for prophylaxis and/or treatment of hepatitis E virus infection and a method for prophylaxis and/or treatment of hepatitis E virus infection; to a recombinant expression vector comprising said nucleotide molecule in present invention and a host cell transformed with said recombinant expression vector that is able to express monoclonal antibody and its conserved variants or active fragments or polypeptide or polypeptide analogs.

10 Claims, 21 Drawing Sheets

OTHER PUBLICATIONS

GenBank LOCUS CAA80048 115aa linear Apr. 1, 1993, immunoglobulin variable region [Mus musculus domesticus].

GenBank LOCUS BAA01867 660aa linear Feb. 3, 1999, ORF2 {Hepatitis E virus].

GenBank LOCUS AAD09445 344aa linear Jan. 26, 1999 structural protein 2 [Hepatitis E virus].

International Search Report, Apr. 3, 2003.

Yang et al., "CDR Walking Mutagenesis for the Affinity Maturation of a Potent Human Anti-HIV-1 Antibody into the Picomolar Range," J. Mol. Biol. 1995, 254:392-403 (12 pages).

Lippow et al., "Computational design of antibody-affinity improvement beyond in vivo maturation," Nature Biotechnology 2007, 25:1171-1176 (6 pages).

Chowdhury, "Engineering Hot Spots for Affinity Enhancement of Antibodies," Methods in Molecular Biology edited by: M. Welschof and J. Krauss. Humana Press Inc., Totowa, NJ, 207:179-196 (18 pages), Sep. 16, 2002.

Kashmiri et al., "SDR grafting—a new approach to antibody humanization," Methods 2005, 36:25-34 (10 pages).

Meng J et al: "Identification and charectedzation of the neutralization epitopet(s) of the hepatitis E virus," Virology, Sep. 30, 2001; vol. 288, No. 2, Sep. 30, 2001, pp. 203-211.

Li Xiaofang et al "A C-terminai hydrophobic region is required for homo-oligomerization of the hepatitis E virus capsid (ORF2) protein" Journal of Biomedicine and Biotechnology, vol. 1, No. 3, 2001, pp. 122-128.

Gu Ying et al: "Selection of a peptide mimicking neutralization epitope of hepatitis E virus with phage peptide display technology." World Journal of Gastroenterology : WJG. Jun. 1, 2004, vol. 10, No. 11, Jun. 1, 2004, pp. 1583-1588.

Khudyakov Y E et al: "Antigenic domains of the open reading frame 2-encoded protein of hepatitis E virus." Journal of Clinical Microbiology. Sep. 1999, vol. 37, No. 9, Sep. 1999, pp. 2663-2871.

Depelchin A et al: "Bovine teutiemie vires (BLV)-infected B-cells express a marker similar to the CD5 T cell marker," Immunology Letters. Jan. 15, 1989, vol. 20, No. 1, Jan. 15, 1989, pp. 69-78.

Li F et al: "Amino-terminal epitopes are exposed wrien full-tength open reading frame 2 of hepatitis E virus is expressed in *Eschenchia coli*, but carboxy-terminal epitopes are masked." Journal of Medical Virology Jul. 1997, vol. 52, No. 3, Jul. 1997, pp. 209-300.

Zhang Jun et al: "Analysis of hepatitis E virus neutralization sites using monoclonal antibodies directed against a virus capsid protein." Vaccine. Apr. 22, 2005, vol. 23, No. 22, Apr. 22, 2005, pp. 2881-2892.

* cited by examiner

Fig.4
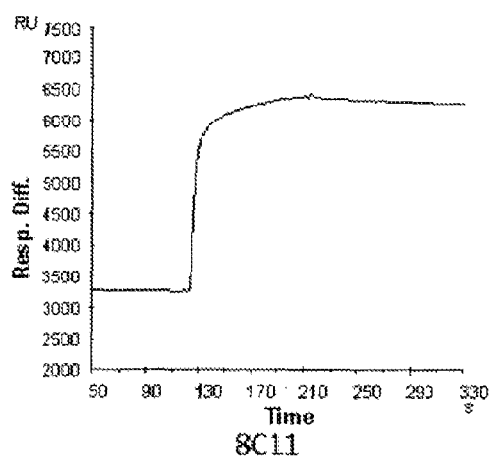
8C11
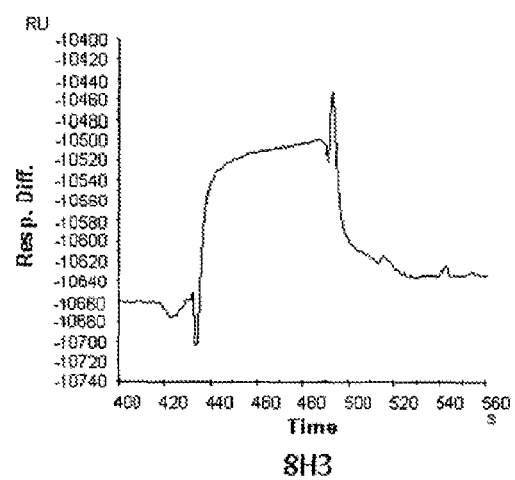
8H3
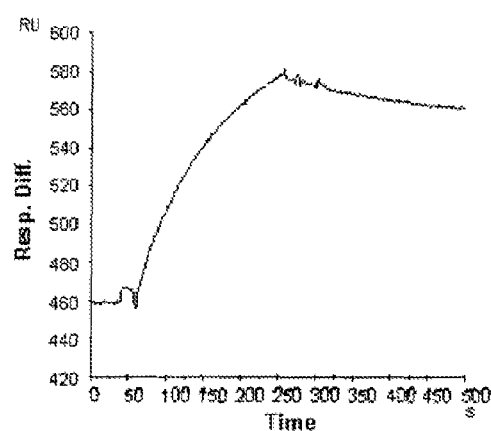
13D8
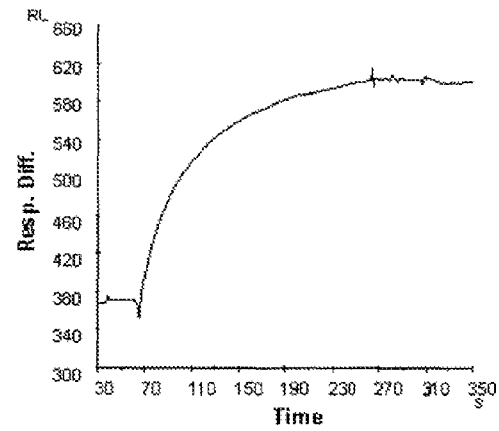
16D7
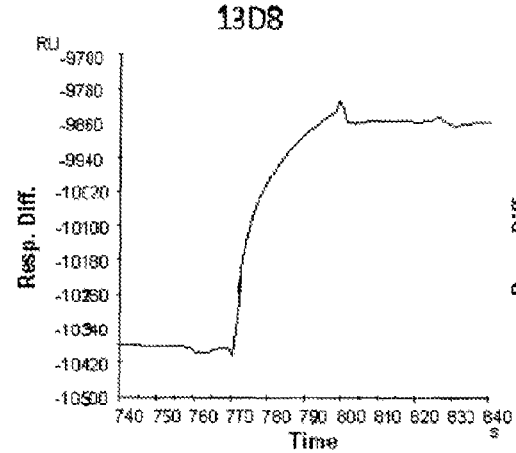
8C11 Fab
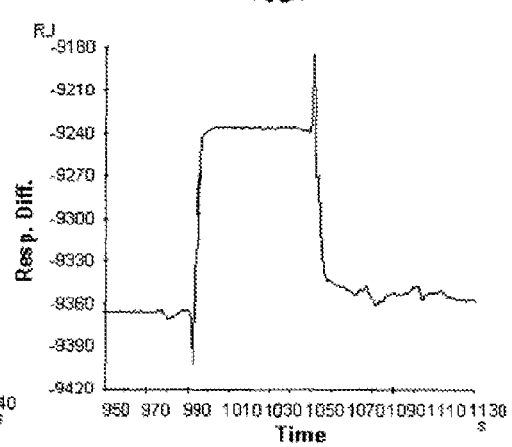
8H3 Fab

MONOCLONAL ANTIBODY AGAINST HEPATITIS E VIRUS OR ITS FRAGMENT WITH BINDING ACTIVITY AND USE THEREOF This is a U.S. national phase application under 35 U.S.C. §371 of International patent application serial no. PCT/CN02/00797, filed Nov. 8, 2002 and claims the benefit of Chinese patent application serial no. 01134643.4, filed Nov. 8, 2001, which is hereby incorporated by reference in its entirety. The International Application was published in Chinese on May 15, 2003 as WO 03/040187 A1 under PCT Article 21(2).

FIELD OF THE INVENTION

The present invention relates to monoclonal antibody specifically binding to polypeptide(s) comprising the amino acid sequence as set forth in SEQ ID No. 1 of hepatitis E virus ORF 2 or its conserved variants or its active fragments, or other monoclonal antibodies against ORF2 which can cross react with said monoclonal antibody of present invention, and its nucleotide sequence or its degenerate sequence; to the antigenic determinants in hepatitis E virus ORF2; to a method for screening an isolated or recombinant polypeptide or polypeptide analog, which has the same property of specifically binding said monoclonal antibody 8C11 and/or 8H3 as the antigenic determinant 1) or 3) of hepatitis E virus ORF2; to a polypeptide or polypeptide analog screened by the above method and its nucleotide sequence or degenerate sequence; to a use of said polypeptide or polypeptide analog in the manufacture of a medicament for diagnosis and/or prophylaxis of the infection of hepatitis E virus; to a kit for the diagnosis of hepatitis E virus infection and a vaccine composition for prophylaxis of hepatitis E virus infection; to a use of said monoclonal antibodies or their active fragments or conserved variants in the preparation of a medicament for diagnosis, prophylaxis and/or treatment of hepatitis E virus infection; to pharmaceutical composition for prophylaxis and/or treatment of hepatitis E virus infection and a method for prophylaxis and/or treatment of hepatitis E virus infection; to a recombinant expression vector comprising the nucleotide molecule of present invention and a host cell transformed with said recombinant expression vector and capable of expressing the monoclonal antibody, its conserved variants or active fragments or polypeptide or polypeptide analogs of the invention.

BACKGROUND OF THE INVENTION

Hepatitis E Virus (HEV) was firstly identified as a pathogen of enterically transmitted non-A, non-B hepatitis in 1983 (Balayan et al., 1983. Intervirology 20:23). Hepatitis E is endemic mainly in developing countries in Asia, Africa and Middle America. In developed countries, hepatitis E cases were mostly found in immigrants or traveler from abroad. Both sporadic cases and pandemic have been reported. During the period from 1950s to 1990s, several hepatitis E outbreaks happened due to polluted drinking water (Visvanathan, 1957, Indian J. Med. Res. (Suppl.). 45:1-30; Wong et al., 1980 Lancet., 2:882-885; Myint et al., 1985, Am J Trop Med Hyg., 34:1183-1189; Belabbes et al., 1985 J Med Virol., 16:257-263; Hau et al., 1999, Am J Trop Med Hyg., 60:277-280). Most hepatitis E infection was self-limited and scarcely developed into a chronic disease; but for the pregnant women, the sequel was severe with a mortality rate up to above 17% (Tsega et al., 1992, Clin. Infec Dis., 14:961-965; Dilawari et al., 1994, Indian J Gastroenterol., 13:44-48; Hussaini et al., 1997, J Viral Hepat., 4:51-54).

In 1991, researchers got the complete genome sequence of HEV for the first time, and it was found that HEV is a single-strand non-enveloped positive RNA virus (Tam et al., 1991, Virology 185:120-131). Sequence analysis showed the genome was about 7.2 kb long with three open reading frames. ORF1, which is located at 5' end, encodes non-structural protein of the virus, and ORF2, which is located at 3' end, encodes major structural proteins of the virus. At 5' end of ORF3, there is one base overlapped with ORF1 3' end. At 3' end of ORF3, there are 339 bases overlapped with ORF2. It's acknowledged that ORF3 encodes another structure protein with unknown function (Tam et al., 1991, Virology, 185:120-131; Aye et al., 1992, Nucleic Acids Res., 20:3512; Aye et al., 1993, Virus Genes., 7:95-109; Huang et al., 1992, Virology, 191:550-558; Reyes et al., 1993, Arch Virol Suppl.,7:15-25).

HEV ORF2, beginning at the base no. 5147, has 1980 nucleotides, which encodes a polypeptide with 660 amino acids presumed to be the major structural protein constituting the capsid of virus. At N-terminal of ORF2 protein, there is a classical signal peptide sequence followed by an arginine-rich region, which is highly positive charged region and is believed to involve in genomic RNA encapisidation during virus assembly. During the translation process, ORF2 enters endoplasmic reticulum (ER) by a mechanism of signal peptide recognizing protein (SRP), and is glycosylated and accumulated in ER, then probably forms the capsomer of capsid in suit. Three N-glycosylated sites on ORF2, Asn-137, Asn-310 and Asn-562, are highly conservative among different virus strains, and Asn-310 is the major glycosylated site. ORF2-transfected mammalian cells COS and human hepatocarcinoma cells Huh-7 and HepG2 can thereby express a 88 kD glycoprotein which can be found in both cytoplasma and membrane. The mutation in those glycosylated sites did not affect the location of PORF2 onto cell membrane. However after the signal peptide sequence was removed therefrom, PORF2 can only be found in cytoplasma. This implied that the shift of PORF2 instead of glocosylation is necessary for protein location onto cell membrane. Like MS protein in HBV, PORF2 is possibly secreted to cell membrane directly through ER, not through Golgi body. On the surface of transfected cell, gpORF2 is not randomly distributed, but concentrated in some zone, which implied an active combination process of protein subunits, which maybe aggregate into certain more ordered advanced forms. The final assembly/maturation of the virus need the encapisidation of genomic RNA, thus must occur in cytoplasma outside of ER or inner wall of cell membrane. The accumulation of gpORF2 on membrane may imply the assembly of virus. At the same time, the localization of capsid protein on membrane also implied the possibility of secretion of matured virus from the cell through budding.

In U.S. Pat. No. 5,885,768, Reyes et al. firstly reported that 4 cynomolgus monkeys were injected i.m. at days 0 and 30 with recombinant protein trpE-C2 expressed in *E. coli* comprising HEV Burma strain ORF2 C terminal 2/3 (aa225~660) in an amount of 50 μg/dose, wherein said protein is formulated with an alum adjuvant. Two monkeys as controls were injected with adjuvant only. In bloods collected four weeks later no antibody is detected by Western Blotting. A third-time immunization on two monkeys among them by administering 80 μg per animal unsolvable recombinant protein without adjuvant. Four weeks later, both monkeys were positive (WB). Then the six monkeys were grouped into two groups, each including three monkeys: one immunized three-times, one two-times, and one as control. The first group was attacked with Burma HEV, and the second group Mexico HEV. The results were that (1) ALT was normal all the time in the immunized group, but it increased 6~10 times higher than before immunization in control; (2) when liver biopsy sample was detected by Immunological Fluorescence method, the antigen was detected in all other monkeys except those immunized with three doses and attacked by Burma strain; (3) virus excretion in feces was found in all other monkeys except those immunized with three doses and attacked by Burma strain. This research sample was small, but it implied that recombinant protein from ORF2 could block the occurrence of biochemical indexes of virus hepatitis and protect completely some monkeys from infection when the monkeys were attacked by wild HEV.

Anderson group in Australia (Anderson et al., 1999. J. Virol. Methods., 81:131-142; Li et al., 1994, J Clin Microbio. 32:2060-2066; Li et al., 1997 J. Med. Virol., 52:289-300; Li et al., 2000, J. Med. Virol., 60:379-386) used ORF2 aa394~660 (ORF2.1) expressed in *E. coli*. The expression product was a fusion protein with GST or poly-His which could form a highly conformation-dependent convalescence epitope. This epitope could detect a high rate of convalescence sera, but it disappeared when the fragment was extended towards N-terminal or truncated. The serum 30 weeks after mice were immunized with recombinant ORF2.1 protein was used to block the serum from convalescence patients with VLP expressed in baculovirus as the coated antigen. The blocking rate reached 81%~86%. Different data showed that ORF2.1 had a major epitope structure rather similar to VLP. The antibody to the epitope can exist for a long time in serum of HEV infected individuals. It's probably an important protective epitope, and antibodies to ORF2.1 would be of value.

In order to overcome many problems during the process of preparation and application of HEV monoclonal antibody, on the basis of obtaining a series of polypeptide fragments with excellent antigenecity within hepatitis E virus ORF2 (see Chinese patent No. CN00130634.0), the inventors prepared monoclonal antibody with NE2 fragment as antigen by hybridroma technology and obtained the cell line which can secrete the monoclonal antibody specifically binding the polypeptide encoded by hepatitis E virus ORF2 and the monoclonal antibody produced by said cell line.

SUMMARY OF THE INVENTION

The present invention in one aspect relates to a monoclonal antibody specifically binding to polypeptide(s) (the amino acid sequence as set forth in SEQ ID No. 1) of hepatitis E virus (HEV) ORF 2, or conserved variants or active fragments thereof wherein one or more of the conserved amino acid residues have been replaced, added or deleted in the amino acid sequences compared to that of said monoclonal antibody of the present invention and which retain the capability of specifically binding to HEV. The present invention also relates to other monoclonal antibodies directed to ORF2 which can cross react with said monoclonal antibody.

In another aspect of the present invention, it relates to a nucleotide molecule comprising nucleotide sequence encoding heavy chain and/or light chain variable regions of the monoclonal antibody of the invention, or its degenerate sequence.

In another aspect of the present invention, it relates to antigenic determinants in hepatitis E virus ORF2.

In another aspect of the present invention, it relates to an isolated or recombinant polypeptide, which comprises at least one of said antigenic determinants of hepatitis E virus ORF2 of the invention or any combination thereof, or comprises fragments with high sequence homology to at least one of said antigenic determinants of the invention.

In another aspect of the present invention, it relates to a nucleotide molecule comprising a nucleotide sequence encoding the isolated or recombinant polypeptide or polypeptide analog, or its degenerate sequence.

In another aspect of the present invention, it relates to a method for screening said isolated or recombinant polypeptide or polypeptide analog which has the equivalent property of specifically binding the monoclonal antibody 8C11 and/or 8H3 of the invention to the antigenic determinants 1) or 3) of hepatitis E virus ORF2 of the invention do.

The present invention also relates to an isolated or recombinant polypeptide or polypeptide analog screened by the above method.

The present invention also relates to a nucleotide molecule comprising a nucleotide sequence encoding said polypeptide or polypeptide analog above or its degenerate sequence.

The present invention also relates to the use of said polypeptide or polypeptide analog in the preparation of a medicament for the diagnosis and/or prophylaxis of the infection of hepatitis E virus.

The present invention also relates to a diagnostic kit for the diagnosis of hepatitis E virus infection, especially the detection of antibody IgG or IgM or total antibody against hepatitis E virus, which comprises a diagnosis effective amount of at least one of said antigenic determinant, polypeptide or polypeptide analogs of hepatitis E virus, and a detection agent suitable for detection of said interaction of antigen and antibody.

The present invention also relates to a vaccine composition for prophylaxis of hepatitis E virus infection, which comprises an immunity effective amount of at least one of said polypeptides or polypeptide analogs of the invention, or any combination thereof, and suitable immunological adjuvant.

The present invention also relates to a use of said monoclonal antibodies or their active fragments or conserved variants in the preparation of a medicament for diagnosis, prophylaxis and/or treatment of hepatitis E virus infection.

The present invention also relates to a diagnostic kit for the diagnosis of hepatitis E virus infection, especially for the detection of hepatitis E virus antigen in samples, comprising at least one of said monoclonal antibodies or their active fragments or conserved variants of the invention, or any combination thereof, in an amount effective for diagnosis, and detection agent suitable for the detection of interaction of said antigen and antibody.

The present invention also relates to a pharmaceutical composition for prophylaxis and/or treatment of hepatitis E virus infection, which comprises a treatment effective amount of at least one of said monoclonal antibodies or their active fragments or conserved variants of the invention, and a pharmaceutically acceptable vehicle and/or excipient.

The present invention also relates to a method for prophylaxis and/or treatment of hepatitis E virus infection, which comprises administrating to the subject a prophylaxis- and/or treatment-effective amount of at least one of said monoclonal antibodies or their active fragments or conserved variants of the invention.

The present invention also relates to a recombinant expression vector comprising said nucleotide molecule of the invention and a host cell transformed with the recombinant expression vector, which is able to express the said monoclonal antibody, its conserved variants or active fragment, or the polypeptide or polypeptide analog of the invention.

The present invention also provides a method for detecting antigen of hepatitis E virus and/or antibody against hepatitis E virus in samples.

DETAILED DESCRIPTION OF THE PREFERRED EMBODIMENT

Unless otherwise indicated, all the terms or nomenclatures used herein have the same meaning as those conventionally used in the art. The procedures of cell culturing, molecular genetics, nucleic acid chemistry, and immunology used herein are routine techniques commonly used in the art.

An antibody comprises aggregation of polypeptide chains linked by disulfide bridges. Two polypeptide chains called light chain and heavy chain constitute all of the main structure of an antibody (isotypes). Both of the heavy and light chain can be further divided into some subregions of variable regions and constant regions. Each heavy chain has a single variable region and three constant domains. Each light chain has a single variable region different from that of the heavy chain and a single constant region different from that of the heavy chain. The variable regions of the heavy and light chain are responsible for the binding specificity of the antibody.

One aspect of the present invention relates to a monoclonal antibody able to specifically bind the polypeptide encoding by hepatitis E virus ORF2 as set forth in SEQ ID NO: 1. In one embodiment, said monoclonal antibody is monoclonal antibody 8C11 against hepatitis E virus produced by hybridoma cell tine CCTCC-C200116, which can directly capture HEV virus, and has protective effect of neutralizing, and has significant sera blocking effect in both acute phase and convalescence phase sera of HEV infection. HEV infected sera can block binding of 8C11 to HEV antigen. Binding of 8C11 to HEV or analog can lead to the change of the spatial structure of HEV or analog, and to significant enhance of the binding of another monoclonal antibody 8H3 against HEV to HEV or analog. The affinity constant of 8C11 with HEV recombinant polypeptide NE2 is about $2 \times 10^{-8}$, and the affinity constant of its Fab fragment is about $6 \times 10^{-7}$.

In another embodiment of the present invention, said monoclonal antibody is monoclonal antibody 13D8 against hepatitis E virus produced by hybridoma cell line CCTCC-C200114, which can directly capture HEV virus, and has protective effect of neutralizing, and has significant sera blocking effect in both acute phase and convalescence phase sera of HEV infection. HEV infected sera can block the binding of 13D8 to HEV antigen. The binding of 13D8 with HEV antigen can be blocked by monoclonal antibody 8C11 and can block the binding of monoclonal antibody 8C11 with HEV antigen. The binding of 13D8 with HEV or analog cannot lead to significant enhance of the binding of another monoclonal antibody 8H3 against HEV to HEV or analog. The affinity constant of 13D8 with HEV recombinant polypeptide NE2 is about $2 \times 10^{-8}$, and the affinity constant of its Fab fragment is about $3 \times 10^{-7}$.

In another embodiment of the present invention, said monoclonal antibody is monoclonal antibody 8H3 against hepatitis E virus produced by cell line CCTCC-C200117, which can directly capture HEV virus. The synergetic action of 8H3 with monoclonal antibody 8C11 can significantly enhance the protective neutralizing effect of 8C11, and has more significant sera blocking effect in both acute phase and convalescence phase sera of HEV infection than monoclonal antibody 8C11 only. HEV infected sera can block binding of 8H3 with HEV antigen. Binding of 8C11 to HEV or analog can lead to significant enhance of the binding of monoclonal antibody 8H3 to HEV or analog. The affinity constant of 8H3 with HEV recombinant polypeptide NE2 is about $2 \times 10^{-6}$, and the affinity constant of its Fab fragment is about $6 \times 10^{-11}$.

In another embodiment of the present invention, said monoclonal antibody is monoclonal antibody 16D7 against hepatitis E virus produced by hybridoma cell line CCTCC-C200115. HEV infected sera can block the binding of 16D7 to HEV antigen. The affinity constant of 16D7 with HEV recombinant polypeptide NE2 is about $2 \times 10^{-8}$.

Another embodiment of present invention relates to said monoclonal antibody, wherein 1) the amino acid sequence of the heavy chain variable region of said monoclonal antibody 8C11 is set forth in SEQ ID No. 12; the amino acid sequence of the light chain variable region is set forth in SEQ ID No. 10; or
2) the amino acid sequence of the heavy chain variable region of said monoclonal antibody 13D8 is set forth in SEQ ID No. 8; the amino acid sequence of the light chain variable region is set forth in SEQ ID No. 6; or
3) the amino acid sequence of the heavy chain variable region of said monoclonal antibody 8H3 is set forth in SEQ ID No. 16; the amino acid sequence of the light chain variable region is set forth in SEQ ID No. 14; or
4) the amino acid sequence of the heavy chain variable region of said monoclonal antibody 16D7 is set forth in SEQ ID No. 20; the amino acid sequence of the light chain variable region is set forth in SEQ ID No. 18.

The term "heavy chain variable region" means a polypeptide, which is 110 to 125 amino acid residues in length, and the amino acid sequence of which corresponds to that of the heavy chain of the monoclonal antibody of the invention beginning from the amino acid of the N terminal. The term "light chain variable region" means a polypeptide, which is 95 to 115 amino acid residues in length, and the amino acid sequence of which corresponds to that of the light chain of the monoclonal antibody of the invention beginning from the amino acid of the N terminal.

The present invention also relates to a binding composition which specifically binds to hepatitis E virus ORF2 protein, comprising at least one of the variable regions of the heavy and/or light chain of the monoclonal antibody of the invention, or any combination thereof.

Said term "binding composition" of the invention means composition comprising two polypeptide chains which: (1) when they effectively bind together, will present the conformation of high binding affinity to the polypeptide encoded by hepatitis E virus ORF2; (2) can be obtained from the hybridoma cell producing said monoclonal antibody or from genetically transformed host cells which express The polypeptide chains of light chain and/or heavy chain variable region of said monoclonal antibody of the invention.

The term "effectively bind" means that when binding together, the two polypeptide chains can be located relatively to each other by various manners, including, but not limited to, binding as in a natural antibody fragment Fab or Fv, or binding by means of genetically engineered single chain antibody (scFv). The two polypeptide chains generally correspond to the light and heavy chain variable regions of said monoclonal antibody.

The terms of Fab, Fc, F(ab)2 and Fv used herein have their respective immunological meanings (Klein, Immunology, John Wiley, New York, 1982; Parham, Chapter 14, in Weir, ed. Immunochemistry, 4th Ed., Blackwell Scientific Publishers, Oxford, 1986).

In the invention, said heavy chain and/or light chain variable region can be prepared by methods conventionally used in the art such as digesting with papain. Examples attached herein disclose the method for preparing Fab of monoclonal antibody 8C11, 8H3 and 13D8.

Another aspect of the present invention relates to nucleotide molecules comprising a nucleotide sequence encoding the variable regions of the heavy chain and/or light chain of said monoclonal antibody of the invention, or its degenerate sequence.

In an embodiment of the present invention, said nucleotide sequence encodes the amino acid sequence of the heavy chain variable region of monoclonal antibody 8C11 as set forth in SEQ ID No. 12, and preferably has the nucleotide sequence of SEQ ID No. 11, or encodes the amino acid sequence of the light chain variable region of monoclonal antibody 8C11 as set forth in SEQ ID No. 10, and preferably has the nucleotide sequence of SEQ ID No. 9.

In an embodiment of the present invention, said nucleotide sequence encodes the amino acid sequence of the heavy chain variable region of monoclonal antibody 13D8 as set forth in SEQ ID No. 8, and preferably has the nucleotide sequence of SEQ ID No. 7, or encodes the amino acid sequence of the light chain variable region of monoclonal antibody 13D8 as set forth in SEQ ID No. 6, and preferably has the nucleotide sequence of SEQ ID No. 5.

In another embodiment of the present invention, said nucleotide sequence encodes the amino acid sequence of the heavy chain variable region of monoclonal antibody 8H3 as set forth in SEQ ID No. 16, and preferably has the nucleotide sequence of SEQ ID No. 15, or encodes the amino acid sequence of the light chain variable region of monoclonal antibody 8H3 as set forth in SEQ ID No. 14, and preferably has the nucleotide sequence of SEQ ID No. 13.

In another embodiment of the present invention, said nucleotide sequence encodes the amino acid sequence of the heavy chain variable region of monoclonal antibody 16D7 as set forth in SEQ ID No. 20, and preferably has the nucleotide sequence of SEQ ID No. 19, or encodes the amino acid sequence of the light chain variable region of monoclonal antibody 16D7 as set forth in SEQ ID No. 18, and preferably has the nucleotide sequence of SEQ ID No. 17.

The invention also relates to the conserved variants or active fragments of said monoclonal antibody, in which one or more of the conserved amino acid residues have been replaced, added or deleted in the amino acid sequence of the monoclonal antibody of the invention, and which still retain the ability of specifically binding to hepatitis E virus.

Term "conserved variants" used in the invention means that the variants substantially retain the parent's properties, such as basic immunological properties, structural properties, regulating properties or biochemical properties. Generally, the amino acid sequence of the conserved variants of the polypeptide is limitedly different from the parent polypeptide such that the conserved variants and the parent polypeptide are closely similar as a whole and are identical in a lot of regions. The difference of amino acid sequence between the conserved variants and parent polypeptide can be replacement, addition and deletion of one or more amino acid residues or any combination thereof. The replaced or added amino acid residues may or may not be encoded by genetic code. The conserved variants of the polypeptide may be variants produced spontaneously or not spontaneously. The polypeptide's conserved variants produced not spontaneously may be produced by induced mutation technique or by direct synthesis.

According to the disclosed contents of the invention, a person skilled in the art would appreciate that the fragment of said monoclonal antibody of the invention may be modified to preserve substantially the property of specifically binding of the monoclonal antibody derivates to hepatitis E virus.

The inventors further conceive other monoclonal antibodies against ORF2 which have cross reactivity with said monoclonal antibody of the invention. According to the detailed information of antigenic determinants disclosed herein, those skilled in the art can prepare hybridoma by the methods known in the art and may obtain monoclonal antibodies with amino acid sequence different from that of said monoclonal antibody of the invention. But both of this monoclonal antibodies and said mono clonal antibody of the invention aim at the same antigenic determinant of said hepatitis E virus, that is, they have immunological activity of cross reactivity. Therefore, the invention also comprises the monoclonal antibody prepared based on the disclosed antigenic determinants and having cross reactivity with said monoclonal antibody of the invention.

In another aspect of the present invention, it further provides an antigenic determinant selected from the antigenic determinants 1)-4) of the polypeptides encoded by HEV ORF2, which:

1) specifically binds the variable region of the monoclonal antibody 8C11 or its analogs; is exposed on the surface of hepatitis E virus particle; depends on conformation, with its correct formation and sufficient exposure being facilitated by the dimerization of the polypeptide fragment of hepatitis E virus ORF2; partly overlaps or is adjacent to the antigenic determinant specifically recognized by monoclonal antibody 13D8; has the key amino acid residues involved in the formation of the antigenic determinant which are approximately located between amino acid residue Nos. 459~601 of hepatitis E virus ORF2; or 2) specifically binds the variable region of the monoclonal antibody 13D8 or its analogs; is exposed on the surface of hepatitis E virus particle; depends on conformation, with its correct formation and sufficient exposure being facilitated by the dimerization of the polypeptide fragment of hepatitis E virus ORF2; partly overlaps or is adjacent to the antigenic determinant specifically recognized by monoclonal antibody 13D8; has the key amino acid residues involved in the formation of the antigenic determinant which are approximately located between amino acid residue Nos. 459~601 of hepatitis E virus ORF2; or 3) specifically binds the variable region of the monoclonal antibody 8H3 or its analogs; is exposed on the surface of hepatitis E virus particle; depends on conformation, with its correct formation and sufficient exposure being facilitated by the dimerization of the polypeptide fragment of hepatitis E virus ORF2; has its sufficient exposure and stability of spatial structure and thereby remarkable enhancement of its ability of binding MAb 8H3 upon the binding of monoclonal antibody 8C11 to HEV; has the key amino acid residues involved in the formation of the antigenic determinant which are approximately located between amino acid residue Nos. 459~601 of hepatitis E virus ORF2; or 4) specifically binds to the variable region of the monoclonal antibody 16D7 or its analogs; is a linear antigenic determinant; is approximately located between amino acid residue Nos. 499~515 of hepatitis E virus ORF2.

In another aspect of the present invention, it further provides an isolated or recombinant polypeptide or polypeptide analogs, comprising at least one of said antigenic determinants of hepatitis E virus ORF2 of the invention or any combination thereof, or a fragment having high sequence homology with at least one of said antigenic determinants.

The term "sequence homology" used in the invention is intended to measure the homology between nucleotide sequences or amino acid sequences. Usually, the sequences are aligned together for the maximum matching. The term "homology" has the same meaning well-known in the art and may be calculated by technology disclosed (COMPUTATIONAL MOLECULAR BIOLOGY, Lesk, A. M., ed., Oxford University Press, 1998; BIOCOMPUTING: INFORMATIOCS AND GENOME PROJECTS, Smith, D. W., ed., Academy press, New York, 1993; COMPUTER ANALYSIS OF SEQUENCE DATA, PART I, Griffin, A. M. & Griffin, H. g., ed., Humana Press, New Jersey, 1994; SEQUENCE ANALYSIS IN MOLECULAR BIOLOGY, von Heinje, G., Academy press, 1987; and SEQENCE ANALYSIS PRIMER, Gribskov, M. & Devereux, J., eds., M Stockton Press, New York, 1991). Although there are many available methods for measuring homology of two polynucleotides or two polypeptides, the term "homology" is well-known by all related technicians (referred to SIAM J. Applied Math. Cartllo, H., & Lipton, D., (1988) 48:1073). The common methods for measuring the homology or similarity of two sequences include but are not limited to those published in Guide to Huge Computers, Martin J. Bishop, ed., Academy Press, San Diego, 1994 and SIAM J. Applied Math. Cartllo, H., & Lipton, D., (1988) 48:1073. All these methods are compiled in computer programs according to some specific rules. Among them, the preferable methods include but are not limited to GCG program (Devereux, J., etc, Nucleic Acids Research (1984) 12(1):387), BLASTP, BLASTN, FASTA (Atschul, S. F., etc, J. Molec. Biol. (1990) 215:403).

For example, a polynucleotide sequence, which has at least 95% "homology" to the reference sequence, means that except for 5 nucleotides in every 100 nucleotides of the polynucleotide, the other nucleotide sequence is identical to that of the reference sequence. In other words, to obtain a polynucleotide sequence having at least 95% homology to the reference sequence, 5% of all nucleotides of the reference sequence may be deleted or substituted with the other kind of nucleotides; or some nucleotides not more than 5% of all nucleotides of reference sequence may be inserted to the reference sequence; or any combination of deletion, insertion and substitution may occur among up to 5% of all nucleotides of reference sequence. And these mutations on the reference sequence may be located at 5' or 3' terminal of the reference sequence, or any place between the two terminals, or may be scattered individually or may form one or more adjacent groups in the reference sequence.

Similarly, a polypeptide sequence, which has at least 95% "homology" to the reference sequence, means that except for up to 5 amino acid residues in every 100 amino acid residues of the polypeptide, the other amino acid sequence is identical to that of the reference sequence. In other words, to obtain a polypeptide sequence having at least 95% homology to the reference sequence, up to 5% of all amino acid residues of reference sequence may be deleted or substituted with other kind of amino acid residues; or some amino acid residues no more than 5% of all amino acid residues of reference sequence may be inserted to the reference sequence; or any combination of deletion, insertion and substitution may occur among up to 5% of all amino acid residues of reference sequence. And these mutations on the reference sequence may be located on 5'- or 3'-terminal of the reference sequence, or any place between the two terminals, or may be scattered individually or may form one or more adjacent groups in the reference sequence.

In one aspect of the present invention, it provides an isolated or recombinant polypeptide or analogs thereof, comprising all of said antigenic determinants 1) and 3) of the present invention, which may form virus-like particle.

In another embodiment of the present invention, all of said isolated or recombinant polypeptide may form virus-like particle, which is 1) polypeptide 208 having amino acid sequence as set forth in SEQ ID NO: 22; or 2) polypeptide 239 having amino acid sequence as set forth in SEQ ID NO: 21; or 3) polypeptide 243 having amino acid sequence as set forth in SEQ ID NO: 23; or 4) polypeptide 251 having amino acid sequence as set forth in SEQ ID NO: 24; or 5) polypeptide 262 having amino acid sequence as set forth in SEQ ID NO: 25; or 6) polypeptide 292 having amino acid sequence as set forth in SEQ ID NO: 26.

In another aspect of the present invention, it further provides a nucleotide molecule comprising the nucleotide sequence encoding said polypeptides or its analogs, or its degenerate sequence.

In one embodiment of the present invention, the nucleotide sequence of said nucleotide molecule encodes: 1) amino acid sequence as set forth in SEQ ID NO: 22; or 2) amino acid sequence as set forth in SEQ ID NO: 21; or 3) amino acid sequence as set forth in SEQ ID NO: 23; or 4) amino acid sequence as set forth in SEQ ID NO: 24; or 5) amino acid sequence as set forth in SEQ ID NO: 25; or 5) amino acid sequence as set forth in SEQ ID NO: 26.

It would be understood by the technicians in the art that said polypeptide able to form virus-like particle (i.e. polymers of HEV NE2 polypeptide) may comprise one or more conserved amino acid replacements, additions and/or deletions and still maintain the property of forming virus-like particle and the immunogenicity. In a general way, polar amino acid residues in said polypeptides may be substituted by other kinds of polar amino acid residues, and nonpolar amino acid residues may be substituted by other kinds of nonpolar amino acid residues, without changing the ability of the polypeptides to form polymers. The specific substitution and modification of amino acids will be discussed in the after-mentioned Examples.

The present invention still provides a method for screening polypeptides or their analogs. Said polypeptides or their analogs have the same property of specifically binding said monoclonal antibody 8C11 and/or 8H3 of the invention as said antigenic determinant 1) or 3) of hepatitis E virus ORF2 of the invention. Said method comprises steps of:

1) contacting said monoclonal antibody 8C11 and/or 8H3 with analyte for a time enough for occurring of the immunoreaction under the conditions suitable for the interaction of antigen and antibody;

2) detecting the existence of the analyte reacting with said monoclonal antibody 8C11 and/or 8H3; and 3) recovering the resultant analyte able to react with said monoclonal antibody.

In one embodiment of the present invention, polypeptides or their analogs, which may specifically bind with said monoclonal antibody 8C11 and/or 8H3 of the invention, may be screened from a 7-peptide phage display library.

In another aspect of the present invention, it further provides some polypeptides or their analogs screened by above-mentioned method. Hereinto, the polypeptides may be selected from a synthesized peptide library using the preceding methods, and the selected polypeptides may have similar amino acid sequence to those preceding polypeptides. Technicians in this research field would appreciate that the polypeptide analogs may be selected from a compound library. So the selected polypeptide analogs could belong to a kind of non-peptide compound, which have similar or mimic property of HEV ORF2 antigenic determinant to bind with said monoclonal antibodies.

In still another aspect of the present invention, it further provides a nucleotide molecule comprising the nucleotide sequence encoding said polypeptides or polypeptide analogs, or its degenerate sequence. Technicians in this research field would appreciate that the polynucleotide sequence or its degenerate sequence may be deduced from the amino acid sequence of the polypeptide or polypeptide analog upon the polypeptide or polypeptide analog is obtained using methods mentioned of the invention.

In another aspect of the present invention, it further provides an use of said polypeptide or its analog in the preparation of a medicament for the diagnosis and/or prophylaxis of hepatitis E virus infection.

In another aspect of the present invention, it further provides a diagnostic kit for the diagnosis of hepatitis E virus infection in biological sample, which comprises a diagnosis effective amount of at least one of said HEV antigenic determinants, polypeptides or their fragments with binding activity according to the present invention, or polypeptides and their analogs screened by the method of the present invention, and a detection reagent suitable for detection of said interaction of antigen and antibody.

In particular, the present invention provides a diagnostic kit for the detection of antibody IgG against hepatitis E virus in the biological sample, which comprises a diagnosis effective amount of at least one of said antigenic determinants, or their fragments; and detection agents corresponding to the adopted detection method.

In one embodiment of the present invention, anti-HEV IgG antibodies of biological sample are detected by ELISA methods using a diagnostic kit comprising NE2 of the present invention.

The present invention also provides a diagnostic kit for detecting IgM antibodies against HEV, which comprises a diagnosis effective amount of at least one of the antigenic determinants or fragments thereof according to the present invention, and a detection reagent suitable for the related methods.

In one embodiment of the present invention, IgM antibodies against HEV are detected by a μ-chain capture ELISA method (E2-IgM), wherein a diagnostic kit is used comprising horseradish peroxidase-labeled antigenic determinant NE2 of the present invention.

In another aspect of the present invention, it further provides a diagnostic kit for detecting total antibodies against HEV, which comprises a diagnosis effective amount of at least one of the antigenic determinants or fragments thereof according to the present invention, and a detection reagent suitable for the related methods.

In an embodiment of the present invention, total antibodies against HEV are detected by a double-antigen sandwiched ELISA method (E2-IgM), wherein a diagnostic kit is used comprising antigenic determinant NE2 and horseradish peroxidase-labeled antigenic determinant NE2 of the present invention.

The term "diagnosis effective amount" of the invention is intended to mean the antigenic determinants or fragments, and polypeptides or polypeptide analogs of the present invention at the amount effective for detection of HEV in biological sample. According to the known immunochemical methods, technicians in the art recognize that the amount of the above-mentioned material would be variable depending on different immunochemical methods in use. Under the teachings of the published references, they know how to select an appropriate amount of the antigenic determinants or fragments, and polypeptides or polypeptide analogs of the present invention so as to diagnose of HEV in biological sample. And they also know that the diagnostic kit, where appropriate, should further include suitable absorbent carrier, buffer reagent/solution, reagent used to produce visible signal for test and user manual. The optimal diagnosis effective amount is 1 ng-10,000 ng per dose, preferably 10 ng-1,000 ng per dose, and more preferably 100 ng-1,000 ng per dose.

Those skilled in the art would be competent for the design of an appropriate immunological method, and relevant reagent, and buffer system suitable for the preceding diagnostic kit according to specific interaction of antigen and antibody, immunochemical test methods as commonly used and the disclosure in the present invention.

In a general way, the immunochemical methods suitable for the preceding diagnostic kit include, but are not limited to:

A method for detecting total antibodies against HEV in biological sample comprising the steps of: immobilizing at lease one of the polypeptides containing the antigenic determinant of the present invention, preferably both antigenic determinants recognized by monoclonal antibody 8C11 and/or 8H3, on the surface of a solid-phase support; adding analyte in suitable buffer; adding a polypeptide carrying a detectable label and comprising said antigenic determinants, preferably both antigenic determinants recognized by monoclonal antibody 8C11 and/or 8H3; and detecting the carried detectable label, thereby determining the presence or amount of anti-HEV antibodies. Preferably the detectable label is horseradish peroxidase or alkaline phosphatase.

A method for detecting antibody IgG against HEV in biological sample comprising the steps of: immobilizing at lease one of the polypeptides comprising the antigenic determinant of the present invention, preferably the polypeptides comprising antigenic determinant recognized by monoclonal antibody 8C11 and/or antigenic determinant recognized by monoclonal antibody 8H3, on the surface of a solid-phase support; adding sample to be detected which is in suitable buffer; adding a secondary antibody carrying a detectable label against IgG antibody of species from which the sample to be detected is derived; and detecting the detectable label carried by the secondary antibody, thereby determining the presence or amount of anti-HEV IgG antibodies in the sample. Preferably the detectable label is horseradish peroxidase or alkaline phosphatase.

A method for detecting antibody IgM against HEV in biological sample comprising the steps of: immobilizing at lease one of the polypeptides comprising the antigenic determinant of the present invention, preferably the polypeptides comprising antigenic determinant recognized by monoclonal antibody 8C11 and/or antigenic determinant recognized by monoclonal antibody 8H3, on the surface of a solid-phase support; adding sample to be detected which is in suitable buffer; adding a secondary antibody carrying a detectable label against IgM antibody of species from which the sample to be detected is derived; and detecting the detectable label carried by the secondary antibody, thereby determining the presence or amount of anti-HEV IgM antibodies in the sample. Preferably the detectable label is horseradish peroxidase or alkaline phosphatase.

A method for detecting antibody IgM against HEV in biological sample comprising the steps of: immobilizing a secondary antibody against IgM antibody of species from which the sample to be detected is derived, on the surface of a solid-phase support; adding sample to be detected which is in suitable buffer; adding at lease one of the polypeptides comprising the antigenic determinant of the present invention, preferably the polypeptides comprising antigenic determinant recognized by monoclonal antibody 8C11 and/or antigenic determinant recognized by monoclonal antibody 8H3, and carrying a detectable label; adding a secondary antibody carrying a detectable label and recognizing said polypeptide; and detecting the carried detectable label, thereby determining the presence or amount of anti-HEV IgM antibodies in the sample. Preferably the detectable label is horseradish peroxidase or alkaline phosphatase.

Hereinto, a method to select a suitable secondary antibody is known to technicians in the field; in addition to horseradish peroxidase and alkaline phosphatase, the detectable label for detecting the interaction of antigen and antibody may be radioisotope, fluorescein, biotin, straptavidin, β-galactosidase, etc.

In another aspect of the present invention, it further provides a vaccine composition for prophylaxis of hepatitis E virus infection in mammals, which comprises immunity effective amount of at least one of the polypeptides or polypeptide analogs according to the present invention or any combination thereof, and a suitable adjuvant. In one embodiment of the present invention, the mentioned vaccine comprises immunity effective amount of at lease one of the polypeptides or polypeptide analogs of the present invention, which comprise antigenic determinants recognizable by monoclonal antibody 8C11 and 8H3.

In one embodiment of the present invention, the vaccine composition for prophylaxis of hepatitis E virus infection in mammals comprises an immunity effective amount of the polypeptides of the present invention, and is able to specifically bind to at least one of the monoclonal antibodies of the present invention. The vaccine may optionally comprise of immunologically acceptable vehicles and/or adjuvant. Those skilled in the art would appreciate whether the adjuvant is used and how to select an adjuvant commonly used in immunology.

The available immunological adjuvants include, but not limited to aluminum hydroxide, aluminum phosphate, complete Freud's adjuvant, incomplete Freud's adjuvant, etc.

In one embodiment of the present invention, said polypeptide 239 with the property of assembling into virus-like particle, is used to prepare vaccine with aluminum-adjuvant or without any adjuvant. And immunization with this vaccine can effectively prevent mice from infection by HEV. The term "immunity effective amount" of the present invention refers to the amount of vaccine sufficient for induction of effective protective immune response in vaccinated individuals. Immunity effective amount of a vaccine may be variable depending on different vaccinating modes, dosage types and vaccinated individuals. With general knowledge in the art, those skilled in the art know how to determine an appropriate amount of a vaccine without undue trials. Preferably, the immunity effective amount is 0.0001 mg-0.1 mg per dose, more preferably 0.001 mg-0.06 mg per dose, and further more preferably 0.1 mg-0.04 mg per dose.

In another aspect of the present invention, it further provides a use of the monoclonal antibodies or their active fragments or conserved variants of the invention in the preparation of a medicament for diagnosis, prophylaxis and/or treatment of hepatitis E virus infection.

HEV particles may be detected using monoclonal antibodies 8C11, 13D8 or 8H3 because these monoclonal antibodies recognize antigenic determinants located on the surface of HEV. In one embodiment of the present invention, it provides a method for detecting HEV particle, comprising the steps of: immobilizing at lease one of the above-mentioned monoclonal antibodies on the surface of a solid-phase support; contacting it with sample to be detected which may contain HEV; adding an antibody against HEV carrying a detectable label; and detecting the complex of monoclonal antibody/HEV immobilized on the surface of the support. In another embodiment of the present invention, it provides a method for detecting HEV particle, comprising the steps of: immobilizing an anti-HEV antibody on the surface of a solid-phase support; contacting it with sample to be detected which may contain HEV; adding said monoclonal antibody carrying a detectable label; and detecting complex of antibody/HEV immobilized on the surface of the support. In another embodiment of the present invention, it provides a method for detecting HEV particle, comprising the step of: mixing the said monoclonal antibody with a detectable label (including colloidal gold particle, emulsion particle, etc.) carrying anti-HEV polyclonal antibody or said monoclonal antibody carrying a detectable label; contacting it with sample to be detected which may contain HEV; and detecting the signal by binding the complex of antibody/HEV to anti-mouse antibody immobilized on the immuno-chromatographic resin during immuno-chromatography.

Similarly, because the monoclonal antibodies 8C11, 13D8 and 8H3 recognize antigenic determinants located on the surface of HEV, these monoclonal antibodies and various derivative antibodies developed based on their antigen binding region (variable regions of heavy chains and light chains of antibody) may be applied for prophylaxis and/or passive immunization treatment of hepatitis E virus infection.

In one aspect of the present invention, in particular, it provides a diagnostic kit for diagnosing the infection of HEV, i.e., detecting the HEV antigen, including diagnosis effective amount of at lease one of the monoclonal antibodies, their active fragments, and conserved variants of the invention, or any combination thereof, and a detection reagent suitable for the interaction of antigen and antibody.

In one embodiment of the present invention, double-antibody sandwiched ELISA is used for detecting HEV antigen, wherein the diagnostic kit comprising the monoclonal antibody of the present invention and horseradish peroxidase-labeled monoclonal antibody 8C11 is used.

The term "diagnosis effective amount" of the present invention refers to the amount of the monoclonal antibody of the present invention sufficient to effectively detect the presence of HEV in biological sample. According to the known immunochemical methods, those skilled in the art recognize that the amount of the above-mentioned material would be variable depending on different specific immunochemical methods used. According to the teachings of the published references, they know how to select an appropriate amount of the monoclonal antibody of the present invention so as to diagnose HEV in biological sample. And they also know that where appropriate, the diagnostic kit may include suitable carrier, buffer reagent/solution, reagents used to detect any signal produced and a user manual. Preferably, the diagnosis effective amount is 1 ng-10,000 ng per dose, more preferably 10 ng-1,000 ng per dose, and still more preferably 100 ng-1,000 ng per dose.

In another aspect of the present invention, it further provides a method for detecting the presence of HEV antigen and/or anti-HEV antibody in biological sample, comprising the steps of:

a) providing a primary antibody being able to specifically bind to HEV and a secondary antibody, wherein at least one of the primary antibody and secondary antibody is the monoclonal antibody or available fragments thereof according to claim 1;

b) providing a signal producer able to bind to the secondary antibody, the intensity of the produced signal being only related to the amount of the secondary antibody; or preferably a signal producer tagged directly to the secondary antibody;

c) linking the primary antibody with a support, forming a binding complex of primary antibody/support;

d) contacting the binding complex with a biological sample to be detected, allowing HEV probably present in sample to bind to the binding complex antibody/support;

e) contacting the secondary antibody which binds effectively to the signal producer with the complex HEV/primary antibody/support, thereby forming a complex of signal producer/secondary antibody/HEV/primary antibody/support; and f) detecting the signal produced from the signal producer.

If desired, in the above detection method, the primary antibody or secondary antibody may be one of or any combination of a plurality of monoclonal antibodies or bindingly active fragments thereof according to claim 1, respectively.

In still another aspect of the present invention, it further provides pharmaceutical composition for treatment of HEV infection, comprising a therapeutically effective amount of at least one of monoclonal antibodies of the present invention, or active fragments or conservative mutants thereof, and pharmaceutically acceptable carriers and/or excipients.

In another aspect of the present invention, it further provides a method for prophylaxis and/or treatment of hepatitis E virus infection, comprising administering to subjects a prophylactically effective amount or a therapeutically effective amount of at least one of preceding monoclonal antibodies of the present invention, or their active fragments or conservative mutants.

The term "prophylactically effective amount" can be replaced with the preceding term "immunologically effective amount", which means the amount sufficient to elicit immune prevention for vaccinated individuals. It is well known that the "prophylactically effective amount" may vary according to the vaccinating ways, chances, vaccinated individuals and the used monoclonal antibodies or their active fragments. According to the published references, teachings and corresponding clinical criterion in the art, the "prophylactically effective amount" can be determined with limited tests. The preferable prophylactically/immunologically effective amount is 0.0001 mg-0.1 mg per dose, more preferably 0.001 mg-0.06 mg per dose, and the most preferably 0.01 mg-0.04 mg per dose.

Similarly, the term "therapeutically effective amount" means the amount sufficient to elicit effective protection for the subjects and to neutralize HEV. And it is well known that a therapeutically effective amount of a monoclonal antibody may vary depending on different treating schemes, illness courses, situations of individuals and the monoclonal antibodies or the active fragment used. According to the published references, teachings and corresponding clinical criterion in the art, a clinician can determine the "therapeutically effective amount" of a monoclonal antibody based on their own experience. The preferable therapeutically effective amount is 0.001 mg-20 mg per kg weight, the more preferably 0.01 mg-10 mg per kg weight, and the most preferably 0.1 mg-10 mg per kg weight.

All of the monoclonal antibodies and active fragment(s) thereof, the antigenic determinant(s) and active fragment(s) thereof, the polypeptides selected by said method of the present invention and their analogs can be expressed in proper host cells by the genetic engineering methods. Therefore, the present invention also relates to a recombinant expression vector comprising the nucleic acid molecule encoding the above monoclonal antibodies or active fragments, the antigenic determinants or their active fragments, the polypeptides selected by said method of the present invention or their analogs. And the invention relates to host cells transformed with said recombinant expression vectors. Many expression host cells can be used in the present invention, for example, prokaryotic cells including but not limited to *Escherichia coli, Bacillus, Streptomyces*; eukaryotic cells including but not limited to *Aspergillus, Saccharomycetes*, and mammalian cells, plant cells and so on. The expression of all interested products mentioned above in the present invention does not only limited to any specific expression-vectors or host cells as long as they can be used to express said monoclonal antibodies, its conservative mutants or active fragments, or said antigenic determinants or their active fragments, and the polypeptides selected by the method in the present invention or their analogs.

The hybridoma cell of this invention can be produced by the known technology in the art. Specifically, it comprises fusing an immortalized cell line with a B lymphocyte that can produce the desired antibody. The method to collect lymphocytes from mammal immunized by special antigen is known. Generally, as to human, peripheral blood lymphocytes can be used; as to the other mammals, splenocyte or lymphocyte can be used. The host mammal repeatedly injected with a purified antigen will produce the desired antibody-producing cells. These cells are collected, and then fused with the immortalized cells. The method for cell fusion is also known in the art. Generally, it comprises the steps of: mixing the cells with fusing agents such as PEG; selecting the hybridoma cells by standard methods such as HAT selection; analyzing the culture medium of the hybridoma by standard immunoassays such as ELISA to select the hybridoma cells that can secrete the desired monoclonal antibodies; and purifying the monoclonal antibodies from culture medium by standard methods for protein purification. For any method mentioned above, there are many reference documents (for example, Kohler et al, hybridoma Techniques, Cold Spring Harbor Laboratory, New York, 1980; Tijssen, Practice and Theory of Enzyme Immunoassays, Elsevier, Amsterdam, 1985; etc).

The application and production of antibody fragments are also well known in the art, for example, Fab (Tijssen, Practice and Theory of Enzyme Immunoassays, Elsevir, Amsterdam, 1985) and Fv (Hochman et al, Biochemistry, 12:1130-1135, 1973; Sharon et al, Biochemistry, 15:1591-1594, 1976; Ehrlich et al, U.S. Pat. No. 4,470,925). Furthermore, bi-specific antibody can be constructed with the compounds and compositions of the present invention by known methods, such as further fusion of the hybridoma cells (which will result in quadromas) (Reading, U.S. Pat. No. 4,474,493) or chemical recombination of half-molecules (Brennan et al, Science, 229:81-83, 1985).

The antibodies and fragments specifically secreted by hybridoma cells in the present invention can also be produced by the method of recombination. The encoding sequences of the monoclonal antibodies in the present invention, especially the encoding sequences of the variable regions of heavy chains and light chains, can be easily obtained by the known methods in the art. The skilled can easily determine the amino acid regions important for the specific binding of monoclonal antibody, for example, the determinant complementary regions (CDR) CDR1, CDR2 and CDR3, in variable regions of heavy chains and light chains of antibody genes, the corresponding amino acid sequences thereof constituting the specific binding regions of the antibodies. Based on these amino sequences the polypeptides with the same or similar specific binding activity to the monoclonal antibody can be prepared by recombination method. For instance, recombination of the DNA sequences encoding variable regions of heavy chain and light chain of an antibody can form a single chain Fv (ScFv); replacement of the corresponding parts of a human antibody with the heavy chain and light chain variable regions or CDRs will give out humanized antibody which is much closer to human antibody while keeping the specific binding activity of original monoclonal antibody; and so on.

In one embodiment of the present invention, an immunoprotective antigen, recombinant protein NE2 from HEV ORF2, was used to immunize mice to prepare monoclonal antibodies, with four hybridoma cell lines obtained that steadily secret monoclonal antibodies and that are named 13D8, 16D7, 8C11 and 8H3 respectively, all secreting IgG1 subtype as determined by subtype test. According to Budapest Treaty, inventors have deposited all these four hybridoma cell lines in CCTCC (Wuhan University, Wuhan province, China), and the deposit numbers are CCTCC-C200114, CCTCC-C200115, CCTCC-200116, CCTCC-C200117, respectively.

According to the monoclonal antibodies or their active fragments prepared in the present invention, the skilled in the art can get the nucleotide sequences encoding the same and get their variants according to codon degeneracy. According to the disclosed contents in the present invention, the skilled in the art can get recombinant expression vectors containing the nucleotide sequences described above, and host cells transformed with the expression vectors by many methods. Selection of host cells and transformation technology were well known in the art, as long as it can be used to express said monoclonal antibodies or their active fragments in the present invention.

Western blottings of boiled and un-boiled NE2 proteins showed that all of the monoclonal antibodies 8C11, 8H3 and 13D8 recognize conformational antigenic determinants, while 16D7 recognizes linear antigenic determinant. Blocking tests and binding inhibition tests show that monoclonal antibodies 8C11 and 13D8 recognize the same antigenic determinant, and that 8H3 and 16D7 identified two other antigenic determinants respectively. Antibody-capturing PCR test shows that monoclonal antibodies 8C11, 13D8 and 8H3 could bind nature hepatitis E virus, demonstrating that the recognized antigenic determinants were on the surface of HEV. Neutralization-protection tests of these monoclonal antibodies show that monoclonal antibodies 8C11 and 13D8 had neutralizing activity, and the antigenic determinant they recognize was neutralizing antigenic determinants, so the polypeptide vaccine containing this antigenic determinant could induce neutralizing antibodies. Moreover, the antigenic determinant recognized by monoclonal antibody 8H3 was also on the surface of HEV, so its antibody may also have the neutralizing activity, or play a role in anti-HEV immunization of individuals.

The present invention also discloses the antigenic determinants formed by the polypeptides of HEV ORF2, which had the characteristic of specific binding to at least one of said monoclonal antibodies 8C11, 8H3, 13D8 or 16D7 in the present invention. These determinants depend on the spacial structures on the surface of natural HEV.

Therefore, the present invention provides pharmaceutical composition for prophylaxis and/or treatment of hepatitis E virus infection, which comprises a therapeutically effective amount of at least one of said monoclonal antibodies or their binding active fragments, and pharmaceutically acceptable carriers and/or excipients. According to the specific conditions of the subject to be treated, the skilled in the art know how to select proper dose and administration routes. The preferable therapeutically effective amount is 0.001 mg-20 mg per kilogram, the especially preferring 0.01 mg-10 mg, and the further more preferably 0.1 mg-10 mg in the present invention.

Western blotting tests showed that monoclonal antibody 16D7 is able to sensitively react with recombinant protein NE2 of HEV ORF2 in various existent conditions, capable of detecting trace amount of HEV protein in Western blotting. So monoclonal antibody 16D7 can be used to detect the purity and the present conditions during the preparation of HEV recombinant protein, which is especially advantage for the preparation of recombinant protein, such as HEV recombinant vaccine in high purity.

BRIEF DESCRIPTION OF THE DRAWINGS

FIG. 4 shows the binding and disassociation course of monoclonal antibodies or their Fab fragment with NE2 chip.

Figure 1:
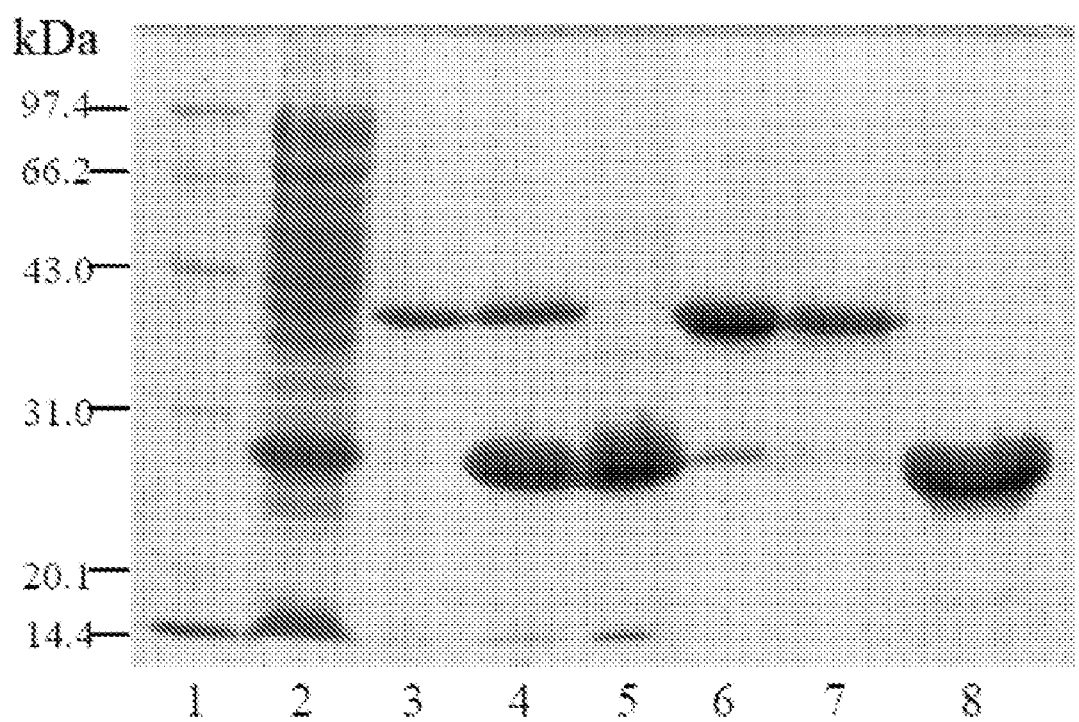
FIG. 1 shows the SDS-PAGE electrophoresis of purified recombinant products of antigen NE2 on HEV ORF2. Lane 1 is molecule weight markers; lane 2 is bacteria lysate; lane 3 is supernatant of 2 mmol/L Urea wash; lane 4 is supernatant of 4 mmol/L Urea wash; lane 5 is supernatant of 8 mmol/L Urea wash; lane 6 is supernatant of 4 mmol/L Urea wash dialysed by PBS; lane 7 is recombinant protein purified by HPLC (unboiled); lane 8 is HPLC purified protein (boiled).

The present invention is further illustrated in details with the following drawings and examples. The following examples are intended only to describe the present invention. Selections of vectors, host cells, reagent concentrations, temperature, and other variants are only illustrative and should in no way be interpreted as the limitation to the protection scope of the present invention.

EXAMPLES

1. Preparation of the Monoclonal Antibodies of the Present Invention

Example 1

Preparation of HEV ORF2 Polypeptide for Use as Antigen

Preparation of HEV ORF2 Fragments for Use as Template.

Using a full-length HEV gene cloned from HEV-infected patient (from Xin Jiang Provine, China) as template (Aye, T. T., Uchida et. al., Nucleic Acids Research, 20 (13), 3512 (1992); GeneBank accession number D11092), two primers, ORF2 FP: 5'-atgcgccctcggcca-3' (SEQ ID NO: 32) as forward primer and ORF2 RP: 5'-aaataaactataactcccga-3' (SEQ ID NO: 33) as reverse primer, polymerase chain reaction (PCR) is carried out in PCR thermal cycler (BIOMETRA T3) under following condition: 94° C. 5 min; then 25 circles of: 94° C. 50 sec. 57° C. 50 sec and 72° C. 2.5 min; ended by 72° C. 10 min, and a specific DNA fragment of HEV ORF 2 about 2 kb is obtained and will be used as the template for the preparation of the polypeptide of the present invention. The above said PCR product is further linked into the commercial available vector pMD18-T (TAKARA Co.) and then the positive clone inserted with ORF2 gene are identified by digestion with BamH I/Hind III. The 2 DNA fragments of HEV ORF 2 obtained by the above method for use as template for preparing polypeptide of the present invention were sequenced in Shanghai Bo Ya Bioengineering Co., Using M13 (+)/(−) primer. One is a conservative sequence (Template 1, SEQ ID NO:2) and the other is a mutant sequence (Template 2, SEQ ID NO: 3).

By sequence alignment and the analysis for open reading frame (ORF), it is found that said mutant sequence of HEV ORF2 (SEQ ID NO:3) for use as template for preparing the polypeptide of the present invention lacks a base A when compared to the conservative sequence (SEQ ID NO:2) and this results in a shift mutation so that the amino acid residues 604-605 in ORF2 is mutated from His-Ser-Val to Pro-Pro-Arg, and the translation of the polypeptide is thereby stopped by a stop code tag formed by the mutation.

Preparation of Polynucleotide Encoding Polypeptide NE2 of the Present Invention and the Expression Vector Comprising the Polynucleotide.

The 810 bp or so DNA fragment is obtained to be the nucleotide sequence encoding polypeptide NE2 of present invention, corresponding to the amino acid sequence listed as SEQ ID NO:4, by PCR using the above-obtained sequence SEQ ID NO:3 as template, forward primers HEFP: 5'-ggatc-catatgcagctgttctactctc gtc-3' (SEQ ID NO: 34), in 5' terminal of which Bam HI site, NdeI site (CAT ATG), and ATG as start codon in *E. coli* system are introduced, and HERP: 5'-ctc-gagaaataaacta taactcccga-3' (SEQ ID NO: 35) as reversed primer, in 5' terminal of which EcoR I site is introduced. The PCR is carried out in thermo cycler (Biometra T3) as follows: heat-denatured for 5 min at 94° C., then amplified for 30 circles: 50 sec at 94° C., 40 sec at 57° C. and 40 sec at 72° C., finally 10 min at 72° C.

The expression vector pTO-T7 for expressing the polypeptide of present invention is constructed according to the known method in the art (LUO Wen-Xin, et al., Chinese Journal of Biotechnology, 2000, 16:53-57), comprising the following particular steps: cloning above-mentioned PCR product into commercial available pMD18-T vector (TAKARA company), and obtaining a positive subclone inserted with the polynucleotide encoding polypeptide NE2 by identification with BamHI/HindIII; further digesting the positive subclone with NdeI and EcoRI to obtain polynucleotide sequence comprising the gene encoding polypeptide NE2, which is then ligated with NdeI/EcoRI-digested pTO-T7. The positive clones pTO-T7-NE2, containing polynucleotide sequence encoding the polypeptide NE2 is verified by digesting with NdeI/EcoRI.

Expression of Polypeptide NE2

1 ul plasmid pTO-T7-NE2 (0.15 mg/ml) was used to transform 40 ul competent cells of *E. coli* ER2566 (from New England BioLabs company) prepared by calcium chloride method. Then the mixture was plated onto kanamycin (to a final concentration of 25 μg/ml, same for the below) containing solid LB medium, and the plate was incubated at 37° C. for 10~12 hours till individual clones were visible. The individual clones were picked and further inoculated in 4 ml LB culture medium in tubes, under 220 rpm at 37° C. for 10 hours, until the $OD_{550\ nm}$ value of the culture is about 1.5. Then 1 ml culture medium was stored at 4° C. for later use, and 2 ul 0.5M IPTG was added into the rest 3 ml of culture (to a final concentration of 0.3 mM). The culture medium contain IPTG was incubated at 37° C. for 4 hours under 220 rpm for inducing the expression of interest polypeptide. 1.5 ml induced culture medium was centrifuged at 12000 g for 30 seconds. The pellet were re-suspended in 100 ul 1×gel loading buffer (50 mM Tris.Cl pH6.8, 100 mM DTT, 2% SDS, 0.1% Bromophenol Blue, 10% Glycerol), and further boiled for 10 minutes, then centrifuged at 12000 g for 10 minutes. 10 ul supernatant was loaded onto 12% SDS-PAGE for analysis of the expression of polypeptide NE2. The transformed strains with highest expressing yield were chosen for large scale expression and stored as seed for future.

200 ul stored bacterium culture was added into 500 ml fresh LB medium in 1 L Erlenmeyer flask, and then shaken under 190 rpm at 37° C. for about 11 hours till the $OD_{550\ nm}$ value reaches 2.0. 300 ul 0.5M IPTG was added to a final concentration of 0.3 mM. Then the mixture was further shaken under 190 rpm at 37° C. for 4 hours. At last, the bacterium pellet was collected from the culture medium after centrifugation.

Purification of Polypeptide NE2 Expressed in *E. coli* Inclusion Body

The *E. coli* culture containing recombinant polypeptide NE2 was centrifuged at 4000 rpm for 15 minutes, and each pellet from 500 ml culture was re-suspended in 15 ml lytic buffer (50 mM Tris.Cl, 10 mM EDTA and 300 mM NaCl, pH7.2). The cell supernatant of 200 ml culture were sonicated in a 250 ml flask in ice bath (Uilbra-Cell VCX500, SONICS & MATERIALS company) with power 70% and big ultrasonic head positioned in center of the liquid, sonicated with 40 seconds on and 1 min off for 20 minutes in total until not obviously viscous and to the extend that there are litter black substance produced by carbonization in the cell pellet obtained by 12000 rpm for 10 minutes at 4° C. The pellet was resuspended with buffer I solution (200 mM Tris.Cl, pH8.5; 5 mM EDTA; 100 mM NaCl) in ½ volume of the suspension, and then supplemented with buffer I solution containing 4% Triton-X100 in equal volume, reaching a Triton-X100 final concentration of 2%. The mixture was shaken at 200 rpm for 30 minutes at 37° C., then centrifuged at 10000 rpm for 10 minutes at 4° C. The pellet was resuspended in equal volume of buffer I, and the mixture was sonicated under conditions as above (40 seconds on, 1 min off; 3 minutes totally), then centrifuged (10000 rpm) for 10 minutes at 4° C. The pellet was resuspended in ½ volume buffer I, and then added another equal volume buffer I containing 4% Triton-X100. After the mixture was shaken (200 rpm) for 30 minutes at 37° C., it was centrifuged (10000 rpm) for 10 minutes at 4° C. The pellet was resuspended in equal volume of buffer I, shaken (200 rpm) for 30 minutes at 37° C. Then the mixture was centrifuged 10000 rpm for 10 minutes at 4° C. The pellet was resuspended in equal volume of buffer I which contains 2M Urea. After shaken at 200 rpm for 30 minutes at 37° C., the mixture was centrifuged 10000 rpm for 10 minutes at 4° C. This supernatant was marked with NE2 2M. The pellet was resuspended in equal volume of buffer I containing 4M Urea. After shaken (200 rpm) for 1 hour at 37° C., the mixture was set at 4° C. overnight, and then it was centrifuged 12000 rpm for 10 minutes at 4° C. This supernatant was marked with NE2 4M, and the pellet was discarded.

Renaturation of Recombinant Polypeptide NE2

100 ml of sample NE2 4M was loaded into 2 dialysis bags (36 DM, retentate MW: 8000~10000 Da, United Carbon Compound, U.S.A.) and dialyzed under stirring in a 1 L beaker, with 900 ml of 1×PBS (20×PBS (1L) containing 73.344 g of $Na_2HPO_4.12H_2O$, 4 g of $KH_2PO_4$, 163.632 g of NaCl, 4.024 g of KCl and pH 7.45) at 25° C. over night (10 hours), and then white precipitates appeared in the dialysis bags. Refreshing the dialysate and going on the dialysis, and then the dialysate was refreshed every 3 hours for 4 times. In principle, the concentration of urea in the sample would be $4\times10^{-6}$M when the dialysis is over. The dialyzed sample was centrifuged at 25° C., 12000 rpm for 10 minutes; the supernatant was filtrated with 0.22 μm filter membrane for further purification.

Purification of Recombinant Polypeptide NE2 with Gel Filtration HPLC

The renaturized NE2 sample was further purified by HPLC as below:

Instrument: Beckman System Gold Nouveau 125NMP/166NMP HPLC,
Column: TSK GEL SW3000 21.5 mm×60 cm,
Elution: 1×PBS pH 7.45,
Flow Rate: 4 ml/min,
Detection wave: UV at 280 nm,
Sample: 2 ml of 4M NE2 (8 mg/ml),
Collection: automatic peak collection of window mode,
Collection time: 1 tube/20 seconds,
Collection delay: 6 seconds.

The results show that after treated in boiling water for 10 minutes, the purity of a sole peak of the interested protein analyzed by SDS-PAGE with 12% acrylamide is up to 90%.

The *E. coli* cell transformed with pTO-T7-E2 plasmid gives out a band on position of 29 kD in SDS-PAGE analysis after being induced, which is about 40% of whole proteins in host cell (FIG. 1, Lane 2), and was mainly present as inclusion bodies. Treated with 2 mol/L, 4 mol/L and 8 mol/L urea in turn, the NE2 inclusion body is present as different forms: in 2 mol/L urea supernatant protein are mainly 40 kD (FIG. 1, Lane 3); in 4 mol/L urea supernatant abundant 29 kD protein appears while a visible 40 kD band still shown (FIG. 1, Lane 4); proteins in 8 mol/L urea supernatant are mainly 29 kD band while 40 kD band almost invisible (FIG. 1, Lane 5); proteins of 4 mol/L urea undergoing dialysis by PBS are mainly 40 kD and 29 kD in ratio of 5:1 (FIG. 1, Lane 6); the renaturized protein being further purified by Gel-filtration HPLC (FIG. 1, Lane 7) and after boiled for 10 min bands 29 kD significantly increased while band 40 kD disappears and no other contaminant band shows (FIG. 1, Lane 8).

MALDI-TOF-MS Analysis of NE2 Polypeptide

Figure 2:
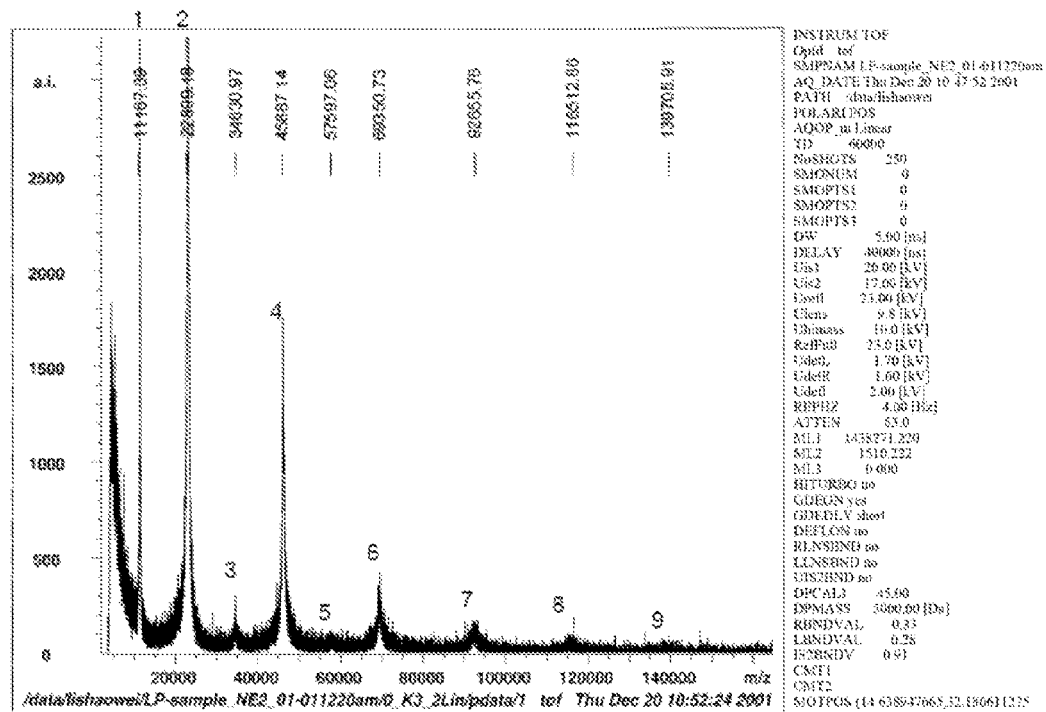
FIG. 2 shows the MALDI-TOF profiles of recombinant protein NE2.

The working matrix solutions was saturated α-cyano-4-hydroxy-cinnamic acid (HCCA) in acetonitrile-0.1% TFA (1:2, v/v), and then mixed with NE2 sample in equal volume which has been purified by HPLC and desalted by pure water. Then the mixture was loaded on a mass spectrometer (Bruker Daltonics company, type REFLEX III) for MS analysis. The NE2 protein showed nine obvious peaks with the mass/charge for the most intensive peak was 22899.18 m/z, comparable to the theoretic molecular weight of NE2 monomer (23,097.02 Da) with one charge. The other eight peaks were multiples of 23,097.02 Da (FIG. 2), which may be different multimers of NE2. In the experimental conditions, protein molecules usually carried 1~2 charges, and thus the nine peaks are deduced to be NE2 proteins from monomer to dodecamer (Table 1).

TABLE 1

The main peaks of recombinant protein NE2 in MALDI-TOF-MS

| Peak No. | measured m/z | Deduced charge number | Expected m/z | Deduced oligomer status |
|---|---|---|---|---|
| 1 | 11167.39 | 2 | 11548.51 | Monomer |
| 2 | 22899.18 | 1/2 | 23097.02 | Monomer/Dimer |
| 3 | 34630.97 | 2 | 34645.53 | Trimer |
| 4 | 45887.14 | 1/2 | 46194.04 | Dimer/Tetramer |
| 5 | 57597.06 | 2 | 57742.55 | Pentamer |
| 6 | 69350.73 | 1/2 | 69291.06 | Trimer/Hexamer |
| 7 | 92655.76 | 1/2 | 92388.08 | Tetramer/Octamer |
| 8 | 116512.86 | 1/2 | 115485.10 | Pentamer/Decamer |
| 9 | 139705.91 | 1/2 | 138582.12 | Hexamer/Dodecamer |

Example 2

Preparation of Hybridoma Cell Lines that Secret Monoclonal Antibodies 8C11, 13D8, 8H3 and 16D7

Immunization of Mice and Fusion Splenocytes thereof with Myeloma Cells

For the primary immunization, each Balb/C female mouse (6-8 weeks old) was inoculated with 5 ug recombinant antigen NE2 emulsified with Freund's complete adjuvant (the total volume is 50 ul). Fifteen days later, the mouse was intramuscularly immunized for the second time with the same amount of NE2 emulsified in Freud's incomplete adjuvant. 30 days later, the mouse was then boosted intravenously (via the tail vein) with 5 ug antigens without the adjuvant. The mice were sacrificed 72 hours after booster immunization. The blood was then collected and the spleen was resected to prepare the suspension of the splenocytes (suspending in RPMI 1640 medium). The splenocytes were counted with a cell counter. Then the splenocytes were mixed in a 6:1 ratio with the SP2/0 mouse myeloma cells and centrifuged. The mixed cells were fused by PEG (PEG 1500) and then mixed with the equal volume of feeder cells, and transferred to 96-well plate (200 ul/well). At the atmosphere of 5% CO2, the plate was incubated in a incubator (ESPEC BNA-31) at 37° C. 3 days later, half of the culture medium was replaced by HT medium (1.361 mg hypoxanthn and 0.388 mg thymidine, in RPMI 1640 medium (GIBCO Int.) to a final volume of 100 ml, dissolved at about 45-50° C. and filtrated for sterilization). 7 days later, in a 96-well plate coated with NE2, ELISA assay was performed on the supernatant of the hybridoma cell culture as described below. The cells positive in ELISA assay were cloned by limited dilution means.

ELISA Assay

HPLC purified NE2 is dissolved in 0.05 mol/L carbonic acid coating buffer (20.02 g $Na_2CO_3$ and 2.52 g $NaHCO_3$, in dd$H_2O$ to a final IL, pH9.5) to a final concentration of 0.3 ug/ml. The 96-well polyvinyl micro-titer plate was treated with the obtained solution at 37° C. for 2 hours and then at 4° C. overnight. The micro-titer plate was washed with PBST (8.0 g NaCl, 0.2 g $KH_2PO_4$, 2.9 g $Na_2HPO_4.12H_2O$, 0.2 g KCl and 0.5 ml Tween-20, in dd$H_2O$ to a final 1 L, pH7.4) to remove the unbound antigens. Then 200 ul blocking solution (2% gultin, 0.2% casein and 2% sucrose in 1×PBS) were added per well for blocking at 37° C. for 2 hours. Then pour off the solution, dry the well and seal the plates in vacuum, stored at 4° C.

For assay, 100 ul supernatant of cell culture were added to each well, and set one positive control (add 100 ul 1:100 diluted mouse multiple anti-NE2 sera) and one negative control (add 100 ul HT medium) for each plate. After incubated at 37° C. for 30 min, the plate was washed with PBST for 5 times and then decanted. HRP-GAM Ig (DAKO company) was added and incubated for another 30 min at 37° C. The plate was washed with PBS-Tween-20 again for 5 times and decanted. 50 ul substrate solution A (13.42 g $Na_2HPO_4.12H_2O$, 4.2 g citric acid.$H_2O$ and 0.3 g $H_2O_2$, in dd$H_2O$ to a final 700 ml) and 50 ul revealing solution B (0.2 g TMD and 20 ml dimethylformamide, in dd$H_2O$ to a final 700 ml) were added to the plate and revealed for 10 min at 37° C. 50 ul stopping solution terminates the reaction. The $OD_{450}$ value of each well was read in an ELISA reader. In general, the $OD_{450}$ value at least twice higher than the negative control can be considered as positive.

Preparation and Purification of Monoclonal Antibody Containing Ascites

Each 10-week-old Balb/C mouse was inoculated intraperitoneally with 0.5 ml incomplete Freud's adjuvant. 2-7 days later, the hybridroma cells were collected and centrifuged. Then the supernatant is discarded and serum-free medium is added to the cells to a final concentration of $2\times10^5$–$2\times10^6$ cells/ml and 0.5 ml was used to inoculate each mouse. The ascites were harvested 7-10 days later when the abdomen of the mouse swelled, and then centrifuged for 15 min at 3,000 rpm. The clear liquid in the middle part of the tube was pipetted out and filtered with 0.45 um micropore membrane for sterilization. The filtrate was stored at −20° C.

Dilute the treated ascites with the equal volume of 0.02 mol/l PBS pH7.4 (81 ml 0.2 mol/L $Na_2HPO_4$ and 19 ml 0.2 mol/L $NaH_2PO_4$, in physiological saline to a final 100 ml). $(NH_4)_2SO_4$ was then added dropwise with gently stirring till 50% saturation, and the ascites was kept at 4° C. overnight. The solution was centrifuged (12,000 rpm) at 4° C. for 15 min, and the supernatant was discarded. The pellet was dissolved in 2 volumes of PBS. $(NH_4)_2SO_4$ was added dropwisely again to the solution with stirring till 33% saturation, and the solution was kept overnight at 4° C. The solution was centrifuged (12,000 rpm) at 4° C. for 15 min, and the supernatant was discarded. The pellet was dissolved in PBS (2 volumes of the ascites used). (NH$_4$)$_2$SO$_4$ was added dropwise with gently stirring until 50% saturation, and kept at 4° C. overnight. The solution was centrifuged (12,000 rpm) at 4° C. for 15 min, and the supernatant was discarded. The pellet was then dissolved in proper amounts of PBS in a dialysis bag and dialyzed in 50-100 volumes of 120 mmol/L Tris-HCl buffer (20 mmol/L NaCl, pH7.8) for about 12 hours at 4° C. under stirring. Replace the buffer for more than three times. The interested product was stored at −20° C. in aliquot package.

According to the method described above, 8 hybridoma cell lines secreting anti-HEV-ORF2 monoclonal antibodies were identified (1F6, 2C9, 7E8, 8C11, 8H3, 13D8, 15B2 and 16D7).

Titration of the Culture Supernatant of Hybridoma Cell Line

Dilute the cell culture supernatant or ascites induced then titer them by indirect ELISA. The results are listed in Table 2.

TABLE 2

Titration of culture supernatants of monoclonal antibody secreting cell and ascites

| | 1F6 | 2C9 | 7E8 | 8C11 | 8H3 | 13D8 | 15B2 | 16D7 |
|---|---|---|---|---|---|---|---|---|
| Supernatant | 1:10$^3$ | 1:10$^4$ | 1:10$^3$ | 1:10$^4$ | 1:10$^4$ | 1:10$^4$ | 1:10$^3$ | 1:10$^4$ |
| Ascites | 1:10$^5$ | 1:10$^6$ | 1:10$^5$ | 1:10$^7$ | 1:10$^6$ | 1:10$^7$ | 1:10$^5$ | 1:10$^7$ |

2. Identification and Characterization of the Monoclonal Antibodies in the Present Invention Example 3

Identification of Types and Subtypes of Monoclonal Antibodies

The ELISA micro-titer plates are coated with purified NE2 according to example 2. 100 ul supernatant of each monoclonal antibody secreting cell culture were added to the plates, then incubated at 37° C. for 30 minutes. Then the plates were washed for 5 times with PBST using TECAN micro-titer plate washer, with the interval of 20 seconds, then decanted. Proper dilutions of the second antibodies of HRP-GAM IgM, IgG1, IgG2a, IgG2b, IgG3 (Serotec company) labeled with enzyme was added in and incubated for another 30 min at 37° C. The plate was washed with PBS-Tween-20 again for 5 times and decanted. One drop for revealing substrate solution A (H$_2$O$_2$) and B (TMD) each were added to the plate and developed for 10 min at 37° C. One drop of stop solution (H$_2$SO$_4$) terminates the reaction. The OD$_{450}$ value for each well is read by an ELISA reader. In general, the threshold is the twice of negative mean and the OD$_{450}$ values above the threshold is positive. The results show that the light chain of all monoclonal antibodies are κ; monoclonal antibody 1F6 is IgG2b, 2C9 is IgG2a, the others 8C11, 8H3, 12G8, 13D8, 15B2 and 16D7 are all IgG1 (Table 3)

TABLE 3

Subtype of monoclonal antibody

| | 1F6 | 2C9 | 7E8 | 8C11 | 8H3 | 13D8 | 15B2 | 16D7 |
|---|---|---|---|---|---|---|---|---|
| HRP-IgG1 | − | − | + | + | + | + | + | + |
| HRP-IgG2a | − | + | − | − | − | − | − | − |
| HRP-IgG2b | + | − | − | − | − | − | − | − |
| HRP-IgG3 | − | − | − | − | − | − | − | − |
| HRP-IgM | − | − | − | − | − | − | − | − |
| Heavy chain subtype | IgG2b | IgG2a | IgG1 | IgG1 | IgG1 | IgG1 | IgG1 | IgG1 |
| Light chain subtype | κ | κ | κ | κ | κ | κ | κ | κ |

Example 4

Western Blotting of HEV Recombinant Protein by Monoclonal Antibodies

Figure 3:
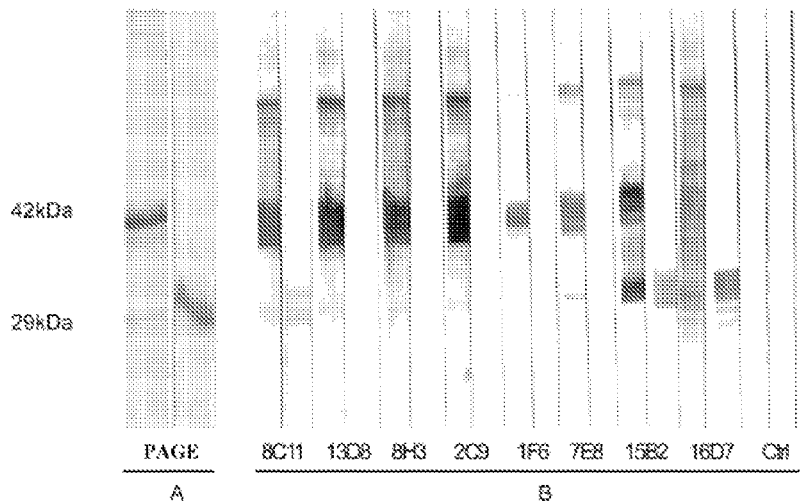
FIG. 3 shows the Western blotting by different monoclonal antibodies of boiled and unboiled recombinant protein NE2. Lanes 1, 2 are SDS-PAGE results; lanes 3~20 are Western blotting results, with odd lanes being unboiled NE2 protein while even lanes being the corresponding boiled NE2 protein. Lanes 3, 4 are monoclonal antibody 1F6; lanes 5, 6 are monoclonal antibody 2C9; lanes 7, 8 are monoclonal antibody 7E8; lanes 9, 10 are monoclonal antibody 8C11; lanes 11, 12 are monoclonal antibody 8H3; lanes 13, 14 are monoclonal antibody 13D8; lanes 15, 16 are monoclonal antibody 15B2; lanes 17, 18 are monoclonal antibody 16D7; and lanes 19, 20 are monoclonal antibody as control.

Recombinant protein NE2 purified by HPLC gel filtration was boiled for 10 minutes, together with unboiled NE2 was separated by 12% SDS-PAGE, and were transferred onto the nitrocellulose membrane. After blocking with 5% skim milk for 1.5 hours at room temperature, the membrane was cut into 0.5 cm wide slots. Monoclonal antibodies were added respectively, reacting at room temperature for 1 hour; then washed 3 times using TNT with 5 mins interval. The AP-labeled Goat anti-mouse (H+L) IgG was added as enzyme-labeled second antibody (Protos Company, diluted in 1:1000 with 5% skim milk) and reacted at room temperature for 1 hour. Washed 3 times by TNT with 5-min intervals, NBT/BCIP was added to develop color (FIG. 3). All the monoclonal antibodies can react well with NE2. Since NE2 is apt to form polymer and the dimmer was still observed on SDS-PAGE, the difference of reaction of monoclonal antibodies with monomer or dimmer of NE2 can be found: monoclonal antibody 1F6, 2C9, 7E8, 8C11, 8H3 and 13D8 react better with NE2 polymer than with NE2 dimmer; on the contrary, monoclonal antibody 15B2 and 16D7 react comparably with NE2 polymer and monomer. NE2 protein disassembled into monomer after boiling, and the reactivity with monoclonal antibody 15B2 and 16D7 is not influenced, while the reactivity with monoclonal antibody 1F6, 2C9, 7E8, 8C11, 8H3 and 13D8 was decreased or disappear.

These results indicate that monoclonal antibody 15B2 and 16D7 recognize the liner epitopes of NE2, and monoclonal antibody 1F6, 2C9, 7E8, 8C11, 8H3 and 13D8 recognize the conformational epitopes of NE2 which are exposed more on the dimmer or polymer than on monomer of NE2 protein.

Example 5

Mensuration of the Binding Kinetics Constant of Monoclonal Antibody to HEV-ORF2 Recombinant Polypeptide Conjugation of HEV-ORF2 Recombinant Polypeptide to Sample Cuvette 1# of Biosensor The recombinant polypeptide NE2 was conjugated on the CMD-treated cuvette of IAsys biosensor (Affinity System company, Iasys Plus) according to the user manual: 200 ul NHS (N-Hydroxysuccinimide) and 200 ul EDC (1-Ethyl-3 (3-Dimethyl-Aminopropyl) Carbodiimide) were mixed, then used to activate hydroxyl groups of CMD (Caarbixtnetgtk Detran) cuvette, which was washed twice with 40 ul EDC/

NHS, and then filled with the above mixture for 7 minutes. Wash with 50 ul of PBST (8.0 g NaCl, 0.2 g KH$_2$PO$_4$, 2.9 g Na$_2$HPO$_4$.12H$_2$O, 0.2 g KCl and 0.5 ml Tween-20, in ddH$_2$O to 1 litter, pH7.4 ) for three times, and equalized for about one minute; then washed for 3 times with 40 ul 10 mM NaAc buffer (pH4.5) and equalized for about one minute, then into either of wells of the cuvette 10 ul NE2 (0.675 mg/ml, 95% in purity) and 10 ul BSA (10 mg/ml) as control are added respectively for observing the binding. Washed for three times with 50 ul of PBST and equalized for one minute, then washed for 3 times with 40 ul 10 mM acetic acid buffer (pH4.5) and equalized for another one minute, then 10 ul NE2 (0.675 mg/ml, 95% in purity) was added for binding for 7 minutes. The cuvettes are washed for three times with 50 ul of PBST and equalized for one minute, then the vacant carboxyl groups are blocked with 1M ethanolamine pH8.5: washing with 40 ul for 3 times and then blocking for 3 minutes. The cuvettes are washed for three times with 50 ul of PBST, and equalized for about one minute, and then washed three times with 50 ul of 10 mM HCl to remove the free and non-specifically abound protein molecule, and equalized for 2 minutes. The cuvettes were washed for three times with 50 ul of PBST, and equalized for 1 minute. The amount of conjugated protein is about 900 arc sec, about 4.5 ng NE2/mm$^2$.

washed three times with 50 ul of 10 mM HCl to remove the free and non-specifically abound protein molecule, and equalized for 2 minutes. The cuvettes were washed for three times with 50 ul of PBST, and equalized for 1 minute. The amount of conjugated protein finally is about 180 arc sec, about 0.9 ng NE2/mm$^2$.

Determination of the Binding Kinetic Constant

The binding kinetic constant of each monoclonal antibody was determined using 2# CMD cuvette by IAsys biosensor. The monoclonal antibody is diluted with PBST into more than 5 dilutions. The cuvette was washed with 45 ul PBST for 2 times and equalized for about one minute. 5 ul diluted monoclonal antibody purified ascites sample is added for binding curve for about 3~5 minutes. The cuvette was washed with 45 ul PBST for 2 times and equalized for about 1~3 minutes for the disassembling curve. The cuvette was washed with 50 ul 50 mM HCl for 3 times and equalized for about one minute; then washed for three times with 50 ul of PBST, and equalized for about one 20 minute. Collect the binding curve of monoclonal antibody binding on the NE2 protein coupling on CMD cuvette during 0~1 minute, and analyze the kinetic constant with FASTfit software. The results are shown in table 4.

TABLE 4

| | Kinetic constants of monoclonal antibodies 8C11, 8H3, 13D8 and 16D7 | | | |
| --- | --- | --- | --- | --- |
| | 8C11 | 8H3 | 13D8 | 16D7 |
| $k_{ass}$ | 10916.1 | 2852.98 | 8364.41 | 5210.99 |
| $k_{diss}$ | 0.00475656 | 0.0435215 | 0.0100895 | 0.00418202 |
| $K_D$ | $4.35738 \times 10^{-7}$ | $1.52548 \times 10^{-5}$ | $1.20624 \times 10^{-6}$ | $8.02538 \times 10^{-7}$ |
| $K_A$ | $2.29496 \times 10^6$ | $6.55533 \times 10^4$ | $8.29021 \times 10^5$ | $1.24605 \times 10^6$ |
| Corr Coeff | 0.999949 | 0.99965 | 0.999993 | 0.998783 |

Conjugation of HEV-ORF2 Recombinant Polypeptide to Sample Cuvette 2# of Biosensor The recombinant polypeptide NE2 was conjugated on the CMD-treated cuvette of IAsys biosensor (Affinity System company, Iasys Plus) according to the user manual: 200 ul NHS and 200 ul EDC were used to activate hydroxyl groups of CMD cuvette, which was washed twice with 40 ul EDC/NHS, and then filled with the mixture for 7 minutes. Wash with 50 ul of PBST for three times, and equalized for about one minute; then washed for 3 times with 45 ul 10 mM acetic acid buffer (pH4.5) and equalized for about one minute, then into either of wells of the cuvette 5 ul NE2 (0.675 mg/ml, 95% in purity) and 5 ul BSA (10 mg/ml) as control are added respectively for observing the binding. Washed for three times with 50 ul of PBST and equalized for one minute, then washed for 3 times with 45 ul 10 mM acetic acid buffer (pH4.5) and equalized for another one minute, then 5 ul NE2 (0.675 mg/ml, 95% in purity) was added for observing the binding amount and the reaction time was controlled not over 300 arc sec according to the first adding amount of NE2 protein. The cuvettes are washed for three times with 40 ul of 10 mM acetic acid buffer (pH 4.5) and equalized for one minute, then additional 10 ul NE2 (0.675 mg/ml, 95% in purity) was added. The cuvettes are washed for three times with 50 ul of PBST and equalized for one minute, then the vacant carboxyl groups are blocked with 1M ethanolamine pH8.5: washing with 40 ul for 3 times and then blocking for 3 minutes. The cuvettes are washed for three times with 50 ul of PBST, and equalized for about one minute, and then Preparation of Fab Fragment of Monoclonal Antibody Purified monoclonal antibody 8C11 (10 mg/ml) is dialysed with 0.1 mol/L Tris-HCl (pH8.0) over night. Papain (from Sigma Co.) was diluted with the same buffer to 2 mg/ml, containing 2 mmol/L EDTA, 1 mmol/L DTT, and incubated at 37° C. for 30 min to be activated. Then the activated papain is added into dialysed monoclonal antibody in weight ratio of 1:100, and incubated at 37° C. for 1 hour. The reaction was terminated by iodoacetamide (to final concentration of 20 mmol/L) in photophobic ice-bath for one hour. Then cleaved monoclonal antibodies is dialysed by 20 mmol/L PB (pH 7.4) overnight. The Fab fragment is purified by DEAE-HPLC with the elution conditions of: eluting with 20 mmol/L PB (pH 7.4) for 0~10 min, renewing with 0.5 mol/L NaCl in 20 mmol/L PBS (pH 7.4) for 10~15 min, then equalizing for 15~20 min with 20 mmol/L PB (pH 7.4). 10~100 mg antibodies are loaded, flow rate is 5 ml/min, and detection wavelength is 280 nm. The Fab fragment purified is condensed with PEG, and dialysed with 20 mmol/L PBS (pH 7.4), and then sterilized with 0.22 μm micropore filter and then aliquoted, that is to obtain the Fab pure product of monoclonal antibody 8C11.

The Fab fragment of 8H3, 13D8 could be obtained by the same means.

Conjugation of HEV-ORF2 Recombinant Polypeptide on CMD-treated Chip CM5 of the Biosensor (BIAcore Type X, BIAcore Co.)

Kinetic Analysis of Conjugation with CM5-NE2 Chip

NE2 is conjugated using amine on CMD-treated Chip CM5 according to BIAcore user manual. 200 ul NHS and 200 ul EDC are mixed to activate the carboxyl groups on CM5 chip: setting reaction temperature at 22° C., and flow rate 10 µL/min, 70 µL mixture is loaded to activate the surface for 7 minutes contact time. NE2 protein (0.675 mg/ml, 95% in purity) diluted in 10 mM Acetate pH 5.5 (in ratio of 1:5) is loaded for coating with the controlled amount. Collect about one minute of baseline date. Unreacted carboxyl groups are then blocked by 75 µl 1M ethanolamine pH8.5. The amount of conjugated protein is about 84RU, and that is about 0.042 ng/mm$^2$.

Binding Kinetic Constants of Monoclonal Antibody 8C11, 8H3 and their Fab Fragment Determined by BIAcore Biosensor Each of monoclonal antibodies and their Fab fragments is diluted with PBS into more than 5 dilutions, and then detected for their binding with NE2 protein coupled on the CM5 chip, and analyzed the kinetics constants by BIAevaluation software.

The KD results for each Fab fragment are shown in table 5. The dissociation rates of 8C11, 13D8 Fab fragment are all relatively quick, similar to the association; association rate of 8H3 Fab fragment becomes significantly increased, and dissociation rate becomes decreased, affinity rate increased 10$^5$. The association and dissociation process of monoclonal antibody to NE2 coupled on the chip is showed in FIG. 4.

TABLE 5

Kinetics constants of monoclonal antibody 8C11, 8H3, 13D8, 16D7 and their Fab fragments with NE2

| Monoclonal antibody | Ka | Kd | KD |
|---|---|---|---|
| 8C11 | | | |
| Full antibody | $2 \times 10^4$ | $5 \times 10^{-4}$ | $2 \times 10^{-8}$ |
| Fab | $8 \times 10^3$ | $5 \times 10^{-3}$ | $6 \times 10^{-7}$ |
| 8H3 | | | |
| Full antibody | 128 | $3 \times 10^{-4}$ | $2 \times 10^{-6}$ |
| Fab | $2 \times 10^5$ | $4 \times 10^{-6}$ | $2 \times 10^{-11}$ |
| 13D8 | | | |
| Full antibody | $1 \times 10^4$ | $2 \times 10^{-4}$ | $2 \times 10^{-8}$ |
| Fab | $2 \times 10^4$ | $6 \times 10^{-3}$ | $3 \times 10^{-7}$ |
| 16D7 | | | |
| Full antibody | $3 \times 10^3$ | $4 \times 10^{-5}$ | $2 \times 10^{-8}$ |

Example 6

Blocking Test of Biosensors

Each of the monoclonal antibodies was diluted to moderate saturation binding concentration based on their binding kinetics analysis, and partnered each other to detect the interaction of 8H3 with monoclonal antibodies 8C11, 13D8, 16D7 using 1# CMD cuvette, and the interaction of 8C11, 13D8, 16D7 each other using 2# CMD cuvette. By first washing the cuvette with 45 uL PBST for 2 times and equilibrating for 1 minute, 5 uL diluted purified ascites sample of monoclonal antibody Ab1 was added and allowed binding of 3~5 minutes; washing the cuvette with 45 uL PBST for 2 times and equilibrating for 1~3 minutes (for the monoclonal antibody which may disassociate such as 8H3, the binding time was extended properly to keep the reaction in balance as possible, and the procedure of dissociation by PBST washing was eliminated); further 5 uL diluted purified ascites sample of monoclonal antibody Ab2 was added and allowed binding for 3~5 minutes, then the binding curve was observed. After washing the cuvette with 45 uL PBST for 2 times and equilibrating for 3~5 minutes, the dissociation curve was observed. The cuvette was washed with 50 uL 50 mM HCl for 3 times and equilibrated for 1 minute; then washed with 50 uL of PBST for 3 times and equilibrated for 1 minute. Exchange the order of Ab1 and Ab2, and repeat the processes above. The binding amount of monoclonal antibody (R) was the increased value of signal at the first 3 minutes from adding the monoclonal antibody. The binding amount of each monoclonal antibody as first antibody (R1) and that as second antibody (R2) were compared. If R2 is more than R1 (enhance rate=(R2−R1)/R1, if it is larger than 20%, it is enhancement), it can be regarded as the added another monoclonal antibody enhances the binding activity of this monoclonal antibody; on the contrary, if R2 is less than R1, it is to say that this monoclonal antibody is inhibited by the added another monoclonal antibody (inhibition rate=(R1−R2)/R1, if it is larger than 30%, it will be regarded as existing inhibition; according to the inhibition rate, there are gentle inhibition (30%~40%), inhibition (40%~60%), evident inhibition (60%~80%) and marked inhibition (more than 80%), and it was considered inhibition when two monoclonal antibodies can inhibit each other.

The inhibition rate of 8C11 on 13D8 is 82%, and the rate of 13D8 on 8C11 is 53%, which suggests that the epitopes recognized by these two monoclonal antibodies overlap each other; while 8C11 and 16D7, 13D8 and 16D7 do not inhibit each other, which shows that there is evident space-interval between the epitope recognized by 16D7 and that recognized by 8C11 and 13D8; similarly there is no inhibition between 8H3 and 13D8, 8H3 and 16D7 each other, which shows that the epitope region recognized by 8H3 is different from those by 13D8 and 16D7 (Table 6). It is unexpected that 8C11 have evident enhancement of 8H3 (enhancement rate near 50%), and the resulted dissociation curve showed that previously the rapid dissociation rate of monoclonal antibody 8H3 became slower due to the influence of 8C11, which indicated that the binding of 8C11 with antigen resulted in spartial conformation changes of antigen so that leads to more sufficient exposure of the epitope on the antigen recognized by 8H3.

TABLE 6

Interaction between MAbs 8C11, 8H3, 13D8 and 16D7

| | Add 8C11 first | Add 13D8 first | Add 8H3 first | Add 16D7 first |
|---|---|---|---|---|
| Add 8C11 then | — | Inhibition | No effects | No effects |
| Add 13D8 then | Marked inhibition | — | Gentle inhibition | No effects |
| Add 8H3 then | Enhancement | No effects | — | No effects |
| Add 16D7 then | No effects | No effects | No effects | — |

Example 7

ELISA Test of the Cross-blocking Effect between the MAbs

The purification of MAb 8C11: 10 ml of 8C11 ascites was precipitated three times with saturated ammonium sulfate, and dialyzed against pH7.2, 10 mM phosphate saline buffer, then loaded on DEAE-52 chromatography equilibrated in the same buffer and the flow-through peak was collected.

Labeling MAb 8C11 with Horseradish Peroxidase (HRP)

Dissolving 1 mg of HRP and NaIO$_4$ each in ultra-pure water; then adding dropwisely NaIO$_4$ solution into HRP solution with agitation, the full mixed solution was placed in dark at room temperature for 30 minutes; dropwisely adding 1 ul ethylene glycol in ultra-pure water into the above mixture solution with agitation, then standing for 30 minutes in dark at room temperature, so far the process of enzyme oxidation was achieved. During the process of HRP oxidation, the purified 8C11 was dialyzed against 50 mM CB, pH ~9.6. After HRP oxidation finished, HRP was mixed with dialyzed 8C11 in desired ratio and dialyzed in 50 mM pH 9.5 CB for more than 6 hours; then stopped by adding freshly prepared $NaBH_4$ solution with the amount of 0.2 mg $NaBH_4$; the resultant was full shaked and stood for 2 hours at 4° C. followed by being dialyzed in 10 mM PBS overnight.

The MAbs 8H3, 13D8 and 16D7 were purified and labeled with HRP in the similar way.

The ELISA microplates were coated with 0.05 ug/ml purified NE2 protein and blocked according to the similar method as described above in example 2. Dividing 20 wells into 4 groups, then adding each of four different MAbs (diluted to $1:10^5$ ELISA titers with 20% newborn bovine sera) into four wells of every group respectively at 100 ul per well and 100 ul of 20% newborn bovine sera in PBS into the rest well as control; after incubating for 30 minutes at 37° C., discarding the liquid and adding 100 ul of four different HRP-labelled MAbs (diluted to $1:10^3$ ELISA titers with 20% newborn bovine sera in PBS); then incubating for 30 minutes at 37° C.; washing five times with PBST and blotting dry, adding 50 ul of each of chromatogen A and chromatogen B, incubating for 15 minutes at 37° C., stopping the reaction with 50 ul of stop solution, and reading $OD_{450/620\ nm}$ in a absorbance reader (PBST, chromatogen A and chromatogen B were all purchased from Beijing Wantai Biomedical Company), finally, the blocking rate was calculated (blocking rate=1−blocked OD/control OD). The blocking rate above 50% was regarded as blocking existence. Only when blocking was incurring each other, it was considered that there exists blocking. As described below in table 7, MAb 8C11 and 13D8 can block each other evidently, but there is no blocking effect between each of them with MAb 8H3 and MAb 16D7; MAb 8H3 and MAb 16D7 can't block the rest three MAbs respectively. This suggested that MAb 8C11 and 13D8 may recognize the same antigenic determinant region, while MAb 8H3 and 16D7 recognized other two antigenic determinant regions.

TABLE 7

The blocking ELISA of MAbs 8C11, 8H3, 13D8 and 16D7

|  | 8C11 | 13D8 | 8H3 | 16D7 |
| --- | --- | --- | --- | --- |
| HRP-8C11 | Blocking | Blocking | No blocking | No blocking |
| HRP-13D8 | Blocking | Blocking | No blocking | No blocking |
| HRP-8H3 | No blocking | Blocking | Blocking | Blocking |
| HRP-16D7 | No blocking | No blocking | Un blocking | No blocking |

Example 8

Enhancement of MAb 8C11 and Fab Fragment thereof on the Binding Activity of MAb 8H3 and Fab Fragment thereof Detected by BIAcore Biosensor Coupling of CM5-NE2 Chips Useful for Detection Coupling was performed according to the manufacture manual: mixing 200 uL NHS and 200 uL EDC to activate carboxyl groups on CM5 chip; loading 100 uL of NE2 protein diluted 1:5 in 10 mM acetate buffer (pH 5.5) (0.675 mg/mL, 95% in purity) and reacting for 10 minutes; blocking unreacted carboxyl groups with 75 μl 1M ethanolamine (pH8.5). The final amount of coupled NE2 protein was 3295RU, corresponding to 1.65 ng/mm².

The Interaction of MAb 8C11 with MAb 8H3 and 8H3 Fab Antibody

Figure 5A:
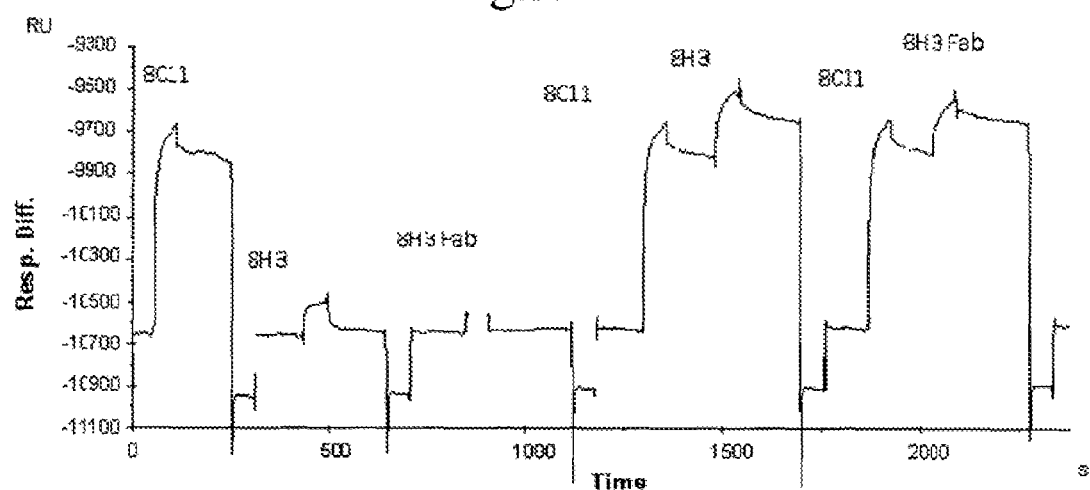
FIG. 5 shows enhanced effect of 8H3 or its Fab fragment by monoclonal antibody 8C11 and its Fab fragment. A is the enhanced effect of 8H3 or 8H3 Fab fragment by monoclonal antibody 8C11; B is the enhanced effect of 8H3 or 8H3 Fab fragment by 8C11 Fab fragment.
Figure 5B:
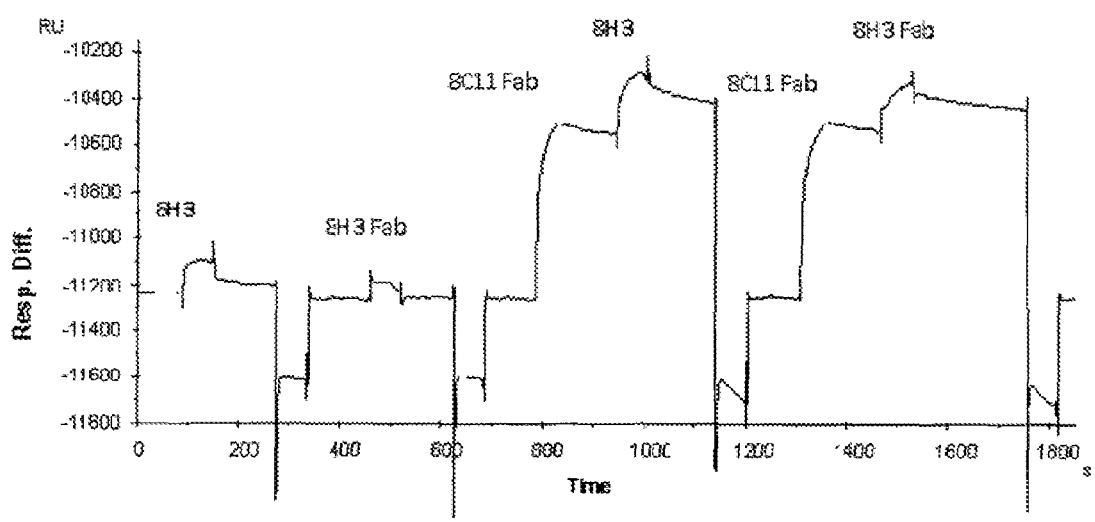

The CM5-NE2 sensor chip for detection was used, and the reaction temperature was set at 22° C., flow rate at 10 μL/min, and the reaction buffer was PBS. After reaching balance, 10 μL monoclonal antibody 8C11 was loaded, the binding and dissociation curves were observed, and then washed with 10 μL 50 mM HCl. The binding and dissociation curves of the monoclonal antibody 8H3 and 8H3 Fab antibody were detected in the same way. Then 10 μL monoclonal antibody 8C11 was loaded, after association and dissociation, 10 μL monoclonal antibody 8H3 was loaded to detect the binding and dissociation of monoclonal antibody 8H3 in the presence of monoclonal antibody 8C11. Then washed with 10 L 50 mM HCl. In the same way, association and dissociation of 8H3 Fab antibody was detected in the presence of monoclonal antibody 8C11. Less association and more dissociation of the monoclonal antibody 8H3 and 8H3 Fab were observed during separate binding procedures. In the presence of monoclonal antibody 8C11, the binding amount become higher and stable as shown in FIG. 5.

The Interaction of 8C11 Fab Antibody with MAb 8H3 and 8H3 Fab Antibody

The CM5-NE2 sensor chip for detection was used, and the reaction temperature set at 22° C., flow rate at 10 L/min, and the reaction buffer was PBS. After reaching balance, 10 L monoclonal antibody 8CH3 was loaded, the binding and dissociation curves were observed, and then washed with 10 μL 50 mM HCl. The binding and dissociation curves between 8H3 Fab antibody were detected in the same way. Then 10 μL monoclonal antibody 8C11 Fab antibody was loaded, after association and dissociation, 10 μL monoclonal antibody 8H3 was loaded to detect the binding and dissociation of MAb 8H3 in the presence of 8C11 Fab antibody. Then wash with 10 μL 50 mM HCl was conducted. In the same way, association and dissociation of 8H3 Fab antibody was detected in the presence of 8C11 Fab antibody. Less association and more dissociation of the monoclonal antibody 8H3 and 8H3 Fab antibody were observed during separate binding procedures. In the presence of 8C11 Fab, the binding amount becomes higher and stable as shown in FIG. 5.

Example 9

Testing the Binding of mAb to HEV Viral Particles by Antibody-captured RT-PCR

Figure 6:
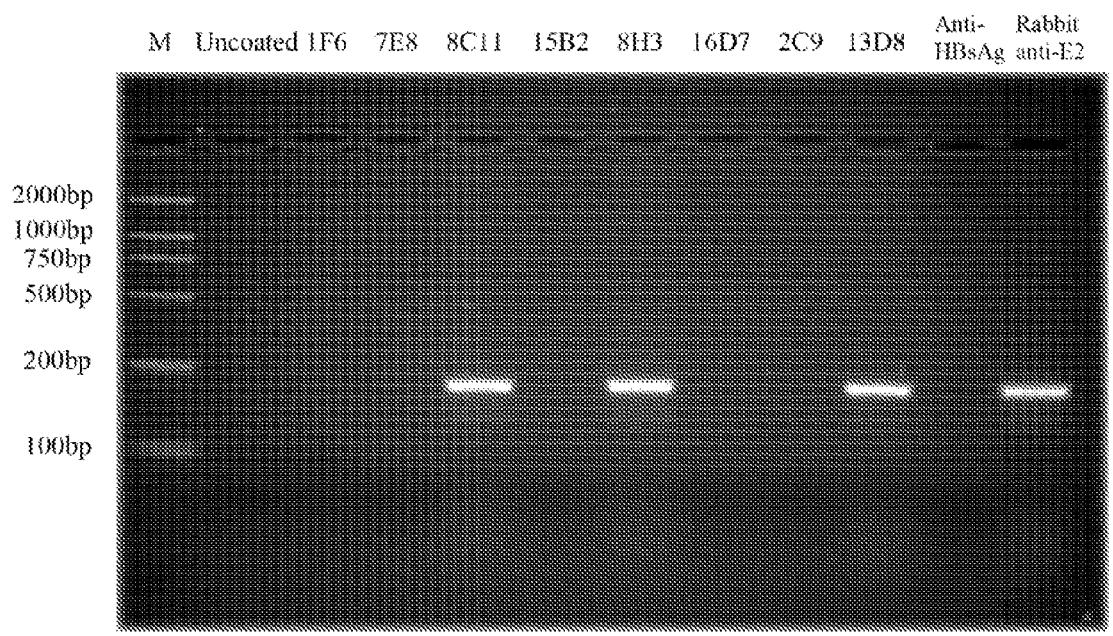
FIG. 6 shows capturing RT-PCR results by monoclonal antibody of HEV in excrement. Lane 1 is molecular weight markers; lane 2 is control without monoclonal antibody; lane 3 is monoclonal antibody 1F6; lane 4 is monoclonal antibody 7E8; lane 5 is monoclonal antibody 8C11; lane 6 is monoclonal antibody 15B2; lane 7 is monoclonal antibody 8H3; lane 8 is monoclonal antibody 16D7; lane 9 is monoclonal antibody 2C9; lane 10 is monoclonal antibody 13D8; lane 11 is anti-HBsAg monoclonal antibody as control; lane 12 is rabbit anti-NE2 polyclonal antibody.

The common 1.5 mL Eppendorf tubes were UV irradiated for 30 min, and then added with 500 uL different MAbs diluted 1:1000 in carbonate coating buffer (20.02 g $Na_2CO_3$ and 2.52 g $NaHCO_3$, with the addition of $ddH_2O$ to 1 L, pH9.5), then incubated overnight at 37° C.; the buffer was discarded, and added 1.5 mL blocking buffer (1× PBS with 2% albumin, pH7.4) to block for 2 hours at 37° C.; the blocking buffer was discarded and added 500 uL 10% HEV positive excrement suspension diluted in sterilized saline to react at 37° C. for 2 hours, then washed with PBST for 6 times; and finally added 250 uL $ddH_2O$ to each of the Eppendorf tubes. RNAs extracted using Trizol reagent (GIBCOL) according to its user manual were subjected to reverse transcription in a 20 μl reaction volume at 42° C. for 40 minutes using AMV reverse transcriptase with the specific primer A3 (4566-4586, 5'-ggctcaccggagtgtttcttc-3' (SEQ ID NO: 36)) as RT primer. Then, the first round of RT-PCR was carried out in a final volume of 20 ul using 2 ul RT template and A3 and A5 primers (4341-4362, 5'-ctttgatgacaccgtcttctcg-3' (SEQ ID NO: 37)) under the following reaction conditions: pre-denaturing at 94° C. for 5 min; 35 cycles of denaturing at 94° C. for 40 s, annealing and extending at 68° C. for 40 s; extending at 72° C. for 5 min. The second round of PCR was carried out in a final volume of 20 ul using 1 ul of the first round reaction product as template and using primers B5 (4372-4392, 5'-gccgcagcaaaggcatccatg-3' (SEQ ID NO: 38)) and B3 (4554-4575, 5'-gtgtttcttccaaaaccctcgc-3' (SEQ ID NO: 39)) under the following reaction conditions: pre-denaturing at 94° C. for 5 min; 35 cycles of denaturing at 94° C. for 40 s, annealing at 56° C. for 40 s and extending at 72° C. for 1 min 20 s; extending at 72° C. for 5 min. As a result, the monoclonal antibodies of 8C11, 8H3 and 13D8 were capable of binding the virus (FIG. 6).

Example 10

The Enhancing Effect of MAb 8C11 on the Ability of MAb 8H3 Capturing Virus

Figure 7:
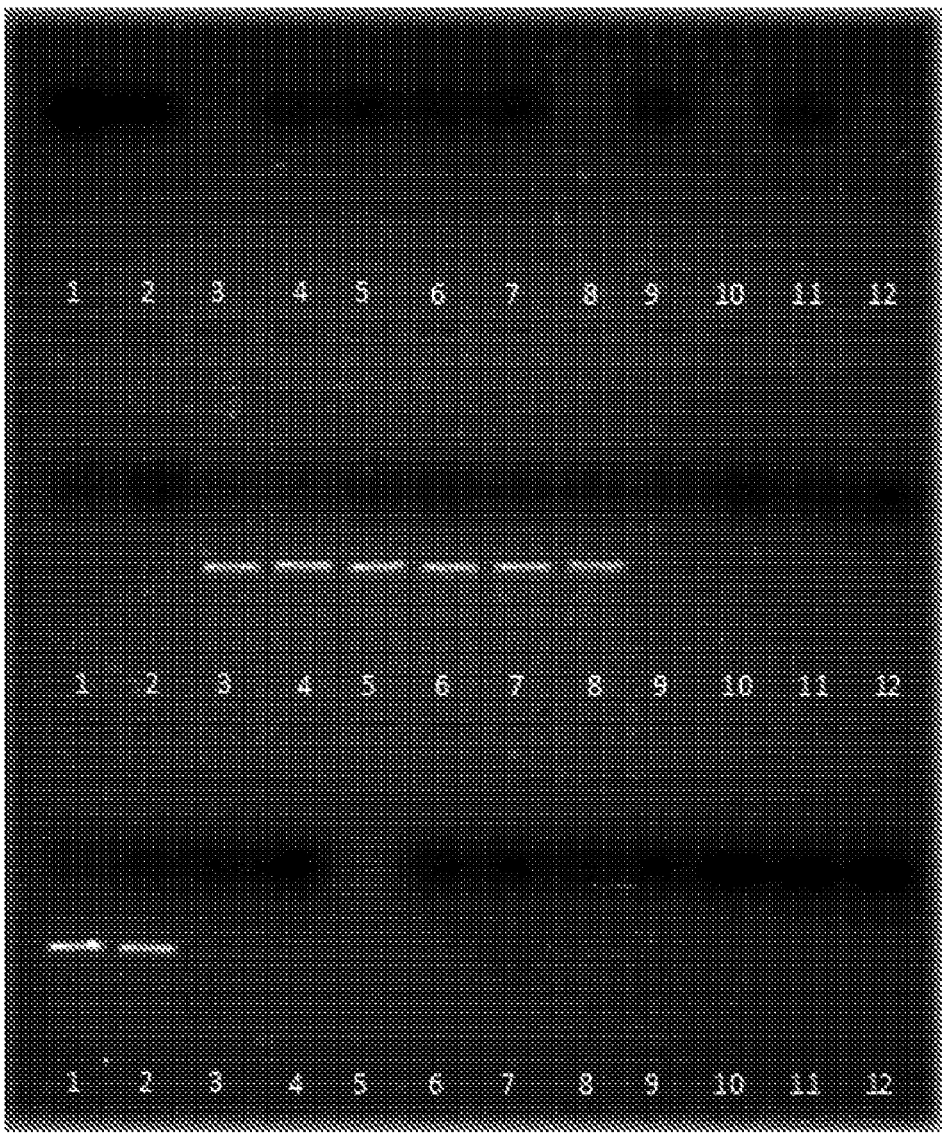
FIG. 7 shows the enhanced capturing activity for HEV of monoclonal antibody 8H3 by monoclonal antibody 8C11. A1~A4 is coated by 8C11; A6~A12 is free of coatings; B1~B12 is coated by 8H3; C1~C2 is coated by 8H3; C4~C7 is coated by 2C9; C9 is negative control of RNA extraction; C11 is the negative control of the second round PCR; A1~A2 is the result of excrement suspension added directly. A3~A4 is the excrement suspension incubated with 1:100 monoclonal antibody 8C11; A6 adds excrement suspension directly; A7~A11 is the result of excrement suspension incubated with 1:10, 1:100, 1:1000, 1:10000 and 1:100000 monoclonal antibody 8C11; A12 is the result of excrement suspension incubated with 1:100 monoclonal antibody 13D8; B1 and B2 add excrement directly; B3, B4 is the excrement incubated with 1:10 monoclonal antibody 8C11; B5, B6 is the excrement incubated with 1:100 monoclonal antibody 8C11; B7, B8 is the excrement incubated with 1:1000 monoclonal antibody 8C11; B9, B10 is the excrement incubated with 1:10000 monoclonal antibody 8C11; B11, B12 is the excrement incubated with 1:100000 monoclonal antibody 8C11; C1, C2 is the excrement incubated with 1:100 monoclonal antibody 13D8; C4, C5 add excrement directly; C6, C7 is the excrement incubated with 1:100 monoclonal antibody 8C11.

A HEV positive excrement suspension with low virus titer was used in immuno-captured RT-PCR assay. To detect the effect of MAb 8C11 or 13D8 (as control) on the ability of MAb 8H3 capturing HEV, various concentrations of the MAb 8C11 or 13D8 (as control) were previously added to the excrement suspension. As below described in FIG. 7, MAb 8C11 specifically enhanced the ability of MAb 8H3 binding the virus markedly, while MAb 13D8, recognizing the similar epitope region of MAb 8C11 and also capturing the virus, had no such effect.

tions, and were subjected to reverse transcription in a 20 μl reaction volume using AMV reverse transcriptase at 42° C. for 40 minutes with the specific primer A3 (4566-4586, 5'-ggctcaccggagtgtttcttc-3' (SEQ ID NO: 40)) as RT primer. RT-PCR was carried out in a final volume of 20 ul using 2 ul RT template and A3 and A5 primers (4341-4362, 5'-ctttgatgacaccgtcttctcg-3' (SEQ ID NO: 41)) under the following reaction conditions: pre-denaturing at 94° C. for 5 min; 35 cycles of denaturing at 94° C. for 40 s, annealing and extending at 68° C. for 40 s; extending at 72° C. for 5 min. The second round of PCR was carried out in a final volume of 20 ul using 1 ul of the first round reaction product as template and using primers B5 (4372-4392, 5'-gccgcagcaaaggcatccatg-3' (SEQ ID NO: 42)) and B3 (4554-4575, 5'-gtgtttcttccaaaac-cctcgc-3' (SEQ ID NO: 43)) under the following reaction conditions: pre-denaturing at 94° C. for 5 min; 35 cycles of denaturing at 94° C. for 40 s, annealing at 56° C. for 40 s and extending at 72° C. for 1 min 20 s; extending at 72° C. for 5 min. The PCR titer of the specimen was defined as the highest dilution at which the diluted specimen could be detected positive bands.

Challenged i.v. with 0.5 ml of $10^1$~$10^5$ PCR titers of diluted solution of HEV XM strain, all rhesus monkeys appeared virus excretion, which manifested successful infection. Meanwhile, two rhesus monkeys challenged with $10^0$ PCR titer showed no detectable virus in their excrement and no positive conversion of antibodies and abnormal ALT, which manifested unsuccessful infection. Therefore, the 50% monkey infectious dose ($MID_{50}$) of HEV XM strain was about $10^1$ PCR detectable amount. Furthermore, there was a trend that the lower infectious dose, the later onset time of positive conversion in virus excretion (table 8).

TABLE 8

The detectable HEV markers in different dose infected rhesus monkeys

| Infective dose (PCR titers) | Number | The period of virus excretion (days) | The period of ALT (days) | The peak value of ALT | The period of IgM (days) | The onset time of IgG positive (days) |
|---|---|---|---|---|---|---|
| $10^5$ | H1 | 4-55 | 28-56 | 347 | 21-63 | 21 |
|  | H2 | 4-49 | 21-49 | 333 | 28-49 | 28 |
| $10^4$ | H3 | 4-43 | 38-42 | 67 | 35-49 | 28 |
|  | H4 | 13-70 | 28-63 | 138 | 42-77 | 38 |
| $10^3$ | H5 | 4-49 | 14-28 | 89 | 28-63 | 28 |
|  | H6 | 4-37 | 28 | 105 | 21-63 | 28 |
| $10^2$ | H7 | 16-55 | — |  | 49-77 | 49 |
|  | H8 | 10-34 | 14-28 | 126 | 28-56 | 28 |
| $10^1$ | H9* | 10 |  |  |  |  |
|  | H10* | 16-25 |  |  |  |  |
| $10^0$ | H11 | None | — | — | — | — |
|  | H12 | None | — | — | — | — |

*H9 on day 13, H10 on day 27, H11 on day 63 died in dysentery respectively.

3. The Neutralization Protection Effect of the MAbs Described in the Present Invention Example 11

The Infectious Dose of HEV XM Strain to Rhesus Monkeys

Extraction, reverse transcription and PCR of HEV RNAs from excrement: HEV RNAs were extracted from 200 ul various dilutions of excrement suspensions using Trizol reagent (GIBCOL) according to its manipulation instruc- Example 12

The Neutralization Protection Effect of MAbs 8C11 and 8H3

Twelve monkeys were divided into four groups (3 monkeys per group). Group 1 (monkey KF25~27) was used as control, group 2 (monkey KF 16~18) was neutralized by MAb 8C11, group 3 (monkey KF 19~21) was neutralized by MAb 8H3, group 4 (monkey KF22~24) was neutralized by the combination of MAbs 8C11 and 8H3. The mixtures of 2 ml diluted HEV XM strain positive excrement (diluted to $10^3$ PCR titers)

and 2 ml monoclonal antibody 8C11 ascites (about 1:10$^5$ titers), or 2 ml 8H3 ascites (about 1:10$^4$ titers), or 1 ml 8C11 ascites with 1 ml 8H3 ascites were placed at 4° C. overnight (about 14 hours), then incubated for 2 hours at room temperature. The control group was not incubated with the MAbs. 1 ml of each mixture of virus-MAbs was injected i.v. into 3 rhesus monkeys, respectively. For detection of HEV-RNA in excretion by RT-PCR, excretion specimens were collected starting from the day of challenge, daily for 2 weeks and then twice weekly. Serum samples were taken weekly for measurement of ALT and anti-HEV antibodies.

The result was shown in table 9. All three monkeys in control group showed abnormal ALT and their virus excretion appeared earlier. All monkeys of neutralized groups postponed their onset time of virus excretion markedly, except that only one monkey in 8C11+8H3 group (KF22) appeared abnormal ALT. One monkey (KF24) in 8C11+8H3 group was completely protected without virus excretion and antibodies against HEV throughout the procedure. For another monkey (KF23) in this group, virus excretion happened on day 40 after infection, lasted for less than 2 weeks and then turned into negative; anti-HEV IgM antibody was throughout undetectable and IgG antibody turned into positive until day 56. These results manifested that both of MAb 8C11 and MAb 8H3 had certain neutralizing effect, and the neutralization of the combination of two MAbs was more evidently.

chromatogen and incubated for 10 minutes at 37° C. The reaction was stopped with 50 ul of stop buffer, and the absorbance OD450/620 nm for each well was measured. The NE2 epitope recognized by MAb 8H3 could be enhanced by 8C11, therefore the NE2 pre-coated microwells used in serum blocking test against MAb 8H3 were firstly saturated by 8C11 (1:1000) for 30 minutes so as to expose the 8H3 epitopeon NE2 completely, followed by the similar serum blocking test. The blocking rate of serum against MAb=(mean control OD−mean blocked OD)/mean control OD*100%. The blocking titer of serum was defined as the highest dilution at which the blocking rate was above 50%.

Figure 8:
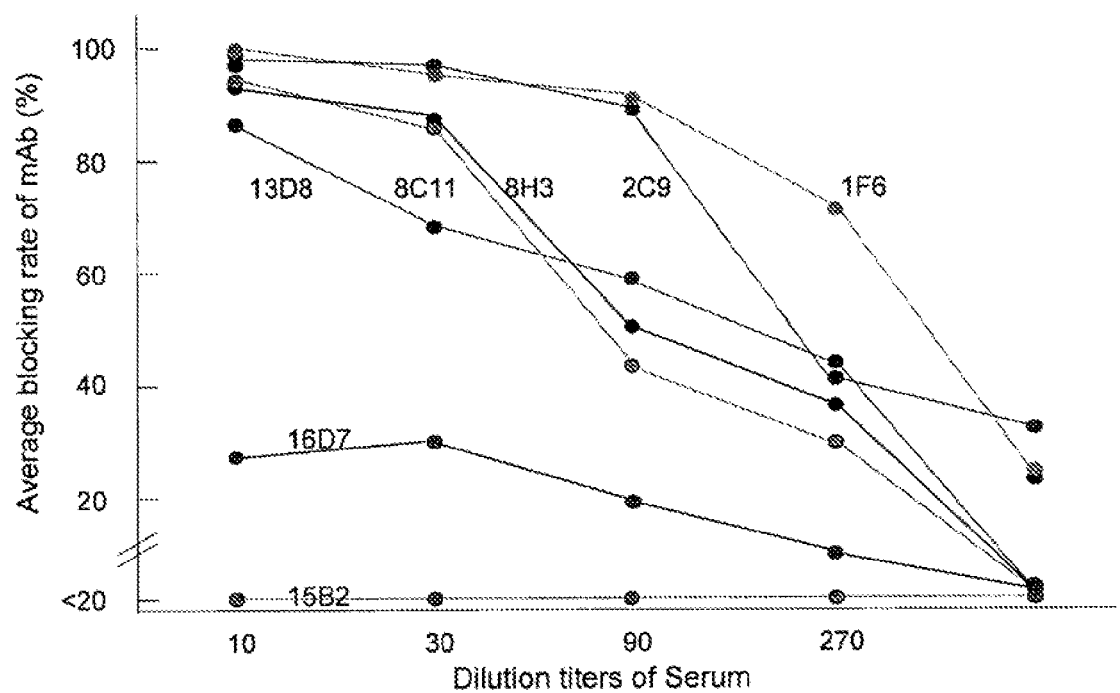
FIG. 8 shows the blocking effect to 8 kinds of anti-NE2 monoclonal antibody by serum from patient of acute HEV infection.

As described in table 10, the sera of acute patients blocked markedly the reaction of five MAbs that recognized conformational epitopes, but didn't block MAb 15B2 that recognized linear epitope. One acute patient's serum could block linear epitope MAb 16D7, and the blocking rate of the other serum was always below 50% with the descending trend along with rising dilution (FIG. 8). The normal human serum had no blocking effect against any MAb. The blocking effect of one acute patient's serum with different dilution series on different monoclonal antibodies was illustrated in FIG. 8. It can be seen that at low dilution, the blocking rates against 5 conformational MAbs were all over 90%, and it indicated an obvious dose effect that the blocking rate decreased with increasing dilution.

TABLE 9

The neutralization test of MAbs

| Group | No of monkey | Virus excretion (days) (onset-end, persistence) | ALT (Peak value/value before challenge) | IgM period (days) (onset-end) | The onset of E2-IgG (day) |
|---|---|---|---|---|---|
| Control | KF25 | 8-54, 47 | 3.3 | 35-63 | 35 |
|  | KF26 | 4-68, 65 | 4.5 | 28-63 | 35 |
|  | KF27 | 16-40, 25 | 3.6 | 35-63 | 35 |
| 8C11 | KF16 | 19-40, 22 | Unrisen | 35-70 | 35 |
|  | KF17 | 26-40, 15 | Unrisen | 42-49 | 42 |
|  | KF18 | 10-58, 49 | Unrisen | 35-49 | 35 |
| 8H3 | KF19 | 16-51, 36 | Unrisen | 49-70 | 49 |
|  | KF20 | 19-58, 40 | Unrisen | 35-84 | 42 |
|  | KF21 | 16-98, 83 | Unrisen | 42-70 | 42 |
| 8C11 + 8H3 | KF22 | 23-40, 18 | 2.3 | 42-49 | 35 |
|  | KF23 | 40-51, 12 | Unrisen | Undetectable | 56 |
|  | KF24 | Undetectale | Unrisen | Undetectable | Undetectable |

4. Inter-blocking Effect of Infectious Sera and the MAbs of the Present Invention Example 13

The Blocking Effect of HEV Patients' Sera on MAbs

The blocking abilities of two acute HEV patient's sera and two normal human sera against NE2 MAbs were detected. Seven enzymatic labeled MAbs were diluted to the concentration at which the OD value of those MAbs reacting with NE2 microplate was between 1.0 and 2.0. The microwells pre-coated with NE2 were divided into two groups, one was blocking group and the other was control group. The wells of blocking group were added with 100 ul of trebly serials diluted sera to be detected (1:10, 1:30, 1:90, 1:270 and 1:810), in duplicate for each dilution. 12 control wells were added with 100 ul of diluent, 2 control wells corresponding to each MAb. After incubated for 30 minutes, the plate was washed 5 times and added diluted enzymatic labeled MAbs 1F6, 2C9, 8C11, 13D8, 15B2 and 16D7. After incubated for another 30 minutes, the plate was washed 5 times, blotted dry, added

TABLE 10

The blocking effect of human serum against NE2 MAbs

| labeled MAb | The mean OD of control | The blocking titres of human serum* | | | |
|---|---|---|---|---|---|
| | | Acute serum 1 | Acute serum 2 | Normal human serum 1 | Normal human serum 2 |
| $T_{1.0}$& | | 2560 | 1280 | — | — |
| 8C11 | 1.36 | 30 | 30 | <10 | <10 |
| 13D8 | 1.76 | 90 | 30 | <10 | <10 |
| 8H3 | 1.05 | 90 | 10 | <10 | <10 |
| 2C9 | 1.79 | 90 | 90 | <10 | <10 |
| 1F6 | 1.36 | 270 | 90 | <10 | <10 |
| 16D7 | 1.27 | <10 | 30 | <10 | <10 |
| 15B2 | 1.18 | <10 | <10 | <10 | <10 |

*The blocking titer of serum was defined as the highest dilution at which the blocking rate was over 50%.
&$T_{1.0}$ was the highest serum dilution of control diluted serum at which the OD value was over 1.0 detected by indirect ELISA.

Example 14

The Blocking Effect of Anti-NE2 MAbs Against HEV Infected Sera

Blocking the Convalescent Serum of HEV Patients with Different Anti-NE2 MAbs

In the NE2 coated and blocked microplate, added 100 ul of 8 diluted anti-NE2 MAbs (1:1000), equal aliquot mixture of MAb 8C11 and 8H3 and diluent as unblocked control respectively; incubated for 30 minutes at 37° C., and blotted dry; then added control diluted convalescent serum from HEV patients and incubated for 30 minutes at 37° C., washed five times with PBST and blotted to dry, then added 100 ul of diluted anti-human IgG-HRP followed by incubating for 30 minutes at 37° C.; washed five times again and blotted to dry; added chromatogen to incubated for 10 minutes at 37° C., stopped the reaction with 50 ul of stop buffer (2M $H_2SO_4$), and the absorbance of $OD_{450/620\ mm}$ was measured. Selecting the dilution at which the control OD value was 1.0~2.0 to calculate the blocking rate by the formula: blocking rate=(1−blocked OD)/unblocked OD)*100%. If more than one unblocked wells had the OD value of 1.0~2.0, the mean blocking rate can be regarded as the blocking rate of said MAb against the serum. It will be considered as positive if the blocking rate was above 50%. As described in table 11, the mixture of 8C11 and 8H3 (8C11+8H3) could block the three patients' sera markedly, while MAbs 8C11 and 13D8 could also block sera 514 and 454.

TABLE 11

The blocking effect of anti-NE2 MAbs against convalescent sera of HEV patients

| Blocking MAb | Blocking rate (%) | | |
|---|---|---|---|
| | Serum 514 | Serum 515 | Serum 454 |
| 1F6 | — | — | — |
| 2C9 | — | — | — |
| 7E8 | — | — | — |
| 8C11 | 72.7 | — | 63.5 |
| 8H3 | — | — | — |
| 13D8 | 67.8 | — | 55.1 |
| 15B2 | — | — | — |
| 16D7 | — | — | — |
| 8C11 + 8H3 | 95.0 | 63.7 | 88.5 |

—, blocking rate was below 50%.

The Blocking Effect of Various MAbs Against the Sera from Different Phases of HEV Infected Monkeys To find out the difference of different MAbs blocking effect on the sera at different phases of 3 HEV infected monkeys, the blocking test was performed in the similar way. As shown in table 12, the results were similar to that from human sera: MAb 8C11 and 13D8 could prominently block the monkey sera at any phases, which indicated the epitope recognized by the two MAbs was immuno-dominant; the combined blocking rate of 8C11+8H3 was substantially over 90%, higher than that of 8C11 or 13D8, which manifested that the epitope recognized by 8H3 was another immuno-dominant one. The antibodies against these two epitopes were important among anti-NE2 antibodies at different infection phases. No effective blocking was observed using 8H3 alone, which could be explained by the binding curves of MAbs 8C11 or 8H3 with NE2 determined by a biosensor. The binding affinity of MAb 8H3 with NE2 was weak and easy to dissociate. When bound to NE2 at the same time as 8C11, the epitope recognized by 8H3 was exposed completely NE2 by the induced change of conformation through 8C11 and thereby could bind the corresponding antibody faster and tighter, therefore the combined blocking of 8C11 and 8H3 could effectively block the corresponding epitopes.

Figure 9:
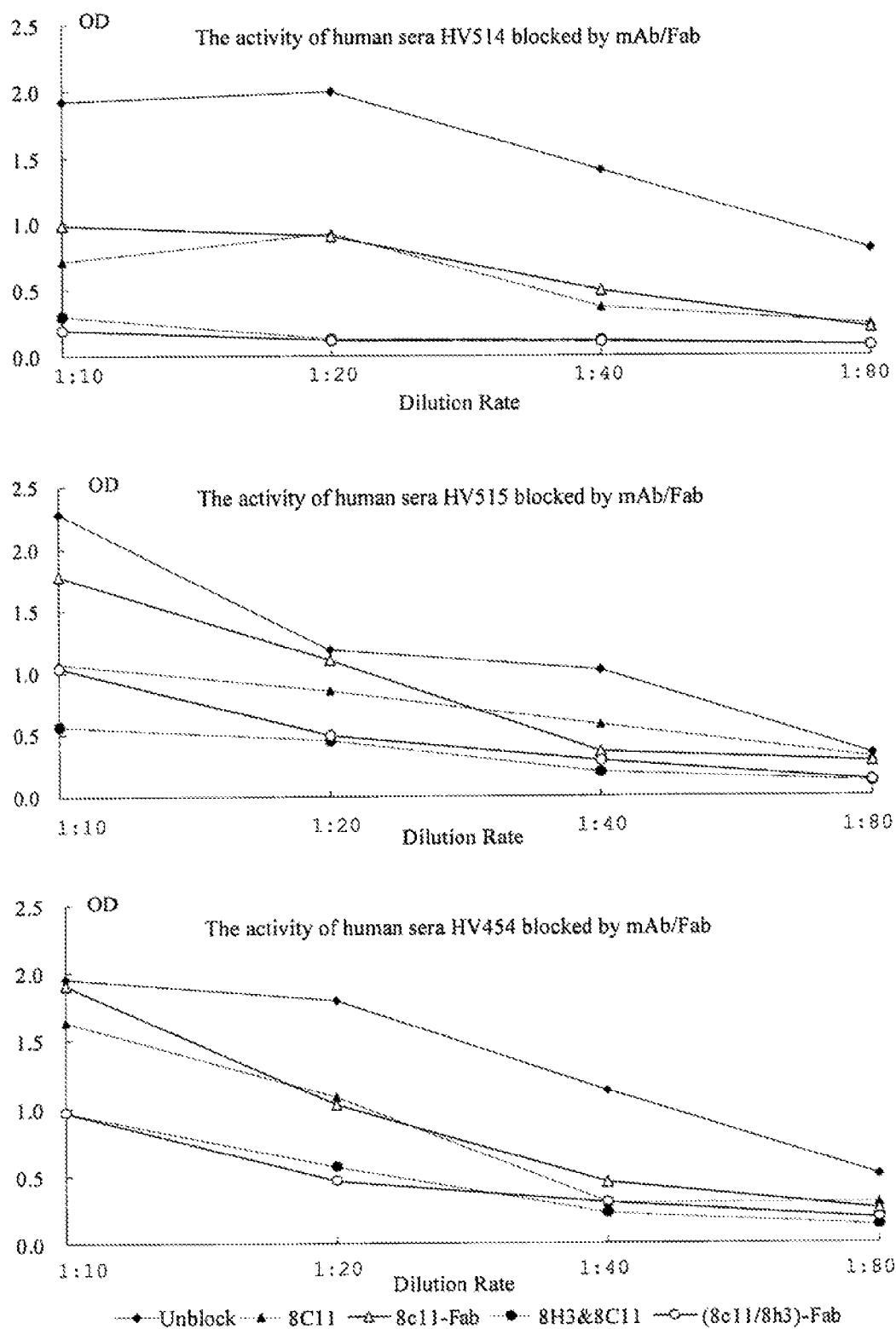
FIG. 9 shows the blocking effect to three serum of HEV infection in recovering phase by 8C11, 8H3 and their Fab fragments.
Figure 10:
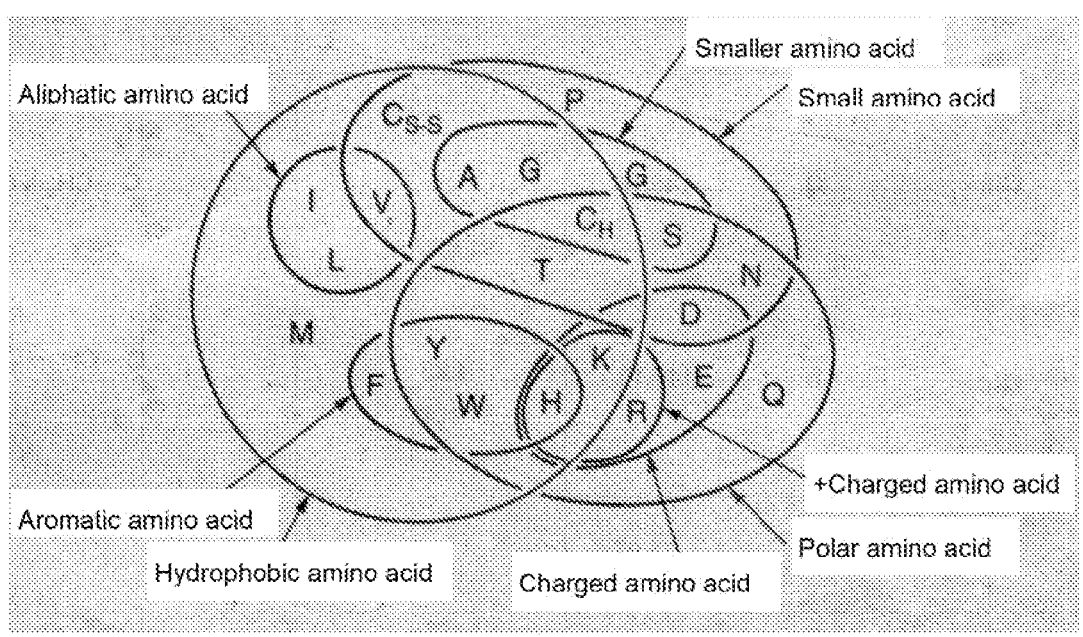
FIG. 10 shows the properties of 20 amino acids.
Figure 11A:
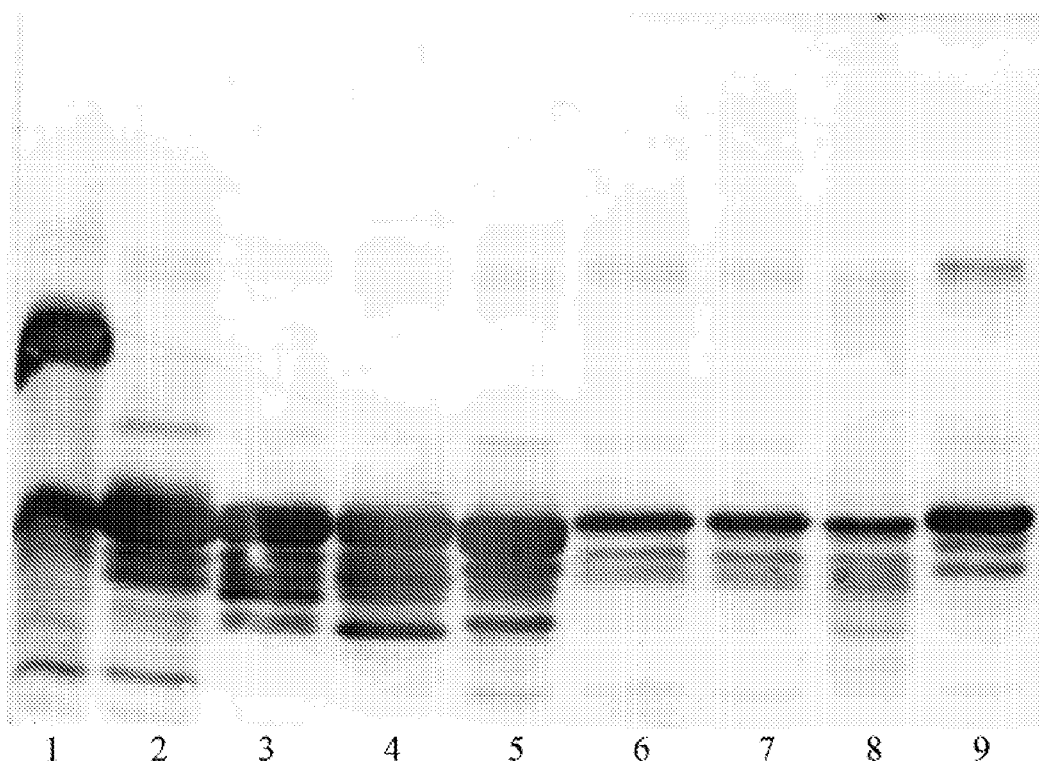
FIG. 11 shows Western blottings of 601 series of mutant proteins by different monoclonal antibodies. A, B are results by monoclonal antibody 16D7, 13D8 respectively: lane 1 is recombinant protein 600VE, lane 2 is recombinant protein 602LE, lane 3 is recombinant protein 599AE, lane 4 is recombinant protein 598VE, lane 5 is recombinant protein 597AE, lane 6 is recombinant protein 601LD, lane 7 is recombinant protein 601LK, lane 8 is 601LH, lane 9 is recombinant protein 601LD. C, D are results by monoclonal antibody 8C11, 8H3 respectively: lane 1 is recombinant protein NE2, lane 2 is recombinant protein 600VE, lane 3 is recombinant protein 602LE, lane 4 is recombinant protein 599AE, lane 5 is recombinant protein 598VE, lane 6 is recombinant protein 597AE, lane 7 is recombinant protein 601LQ, lane 8 is recombinant protein 601LK, lane 9 is 601LH, lane 10 is recombinant protein 601LD. E is SDS-PAGE result of AA601 mutant protein, lane 1 is NE2, lane 2 is 601LP, lane 3 is 601LI, lane 4 is 601LG, lane 5 is 601LE, lane 6 is 601LD, lane 7 is 601LK, lane 8 is 601LN, lane 9 is 601LH.
Figure 11B:
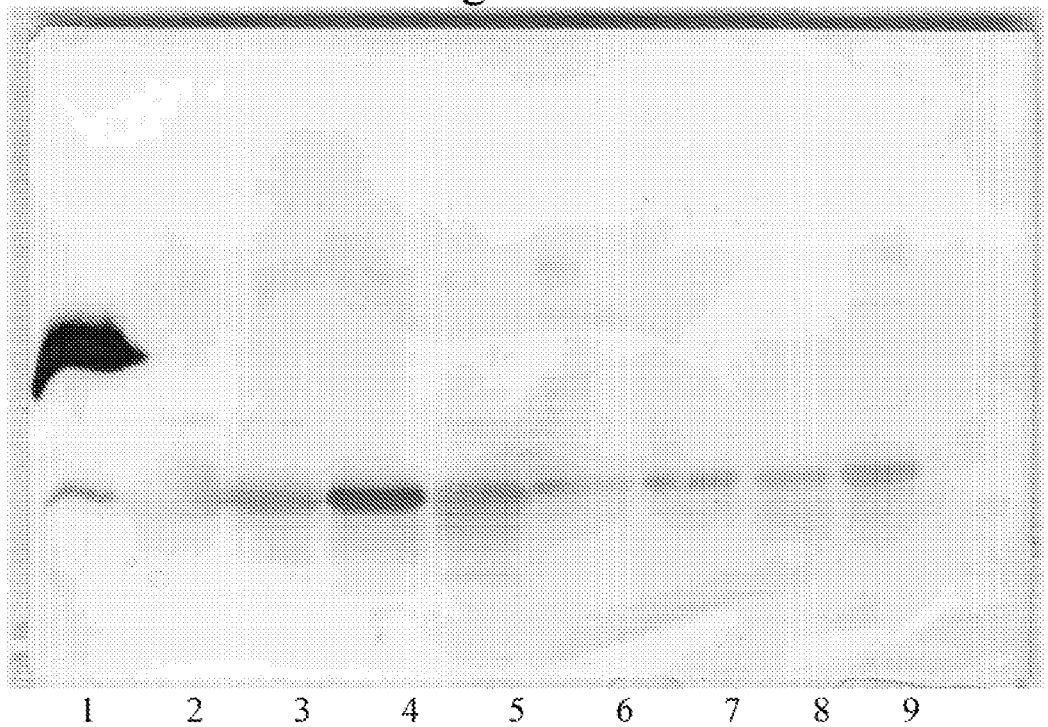
Figure 11C:
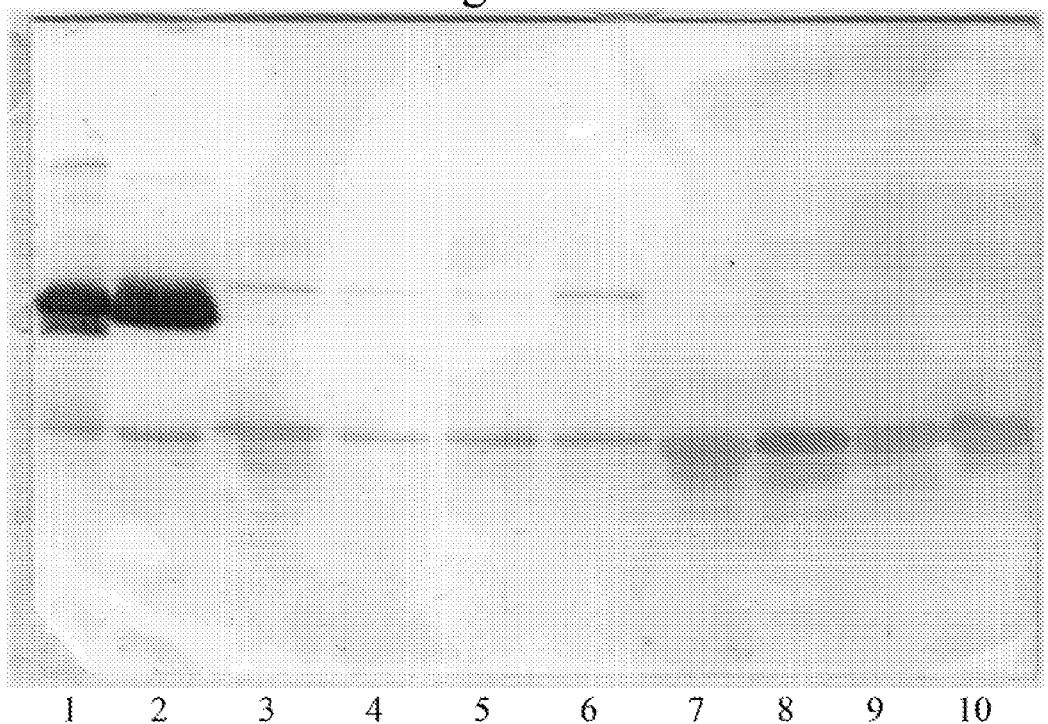
Figure 11D:
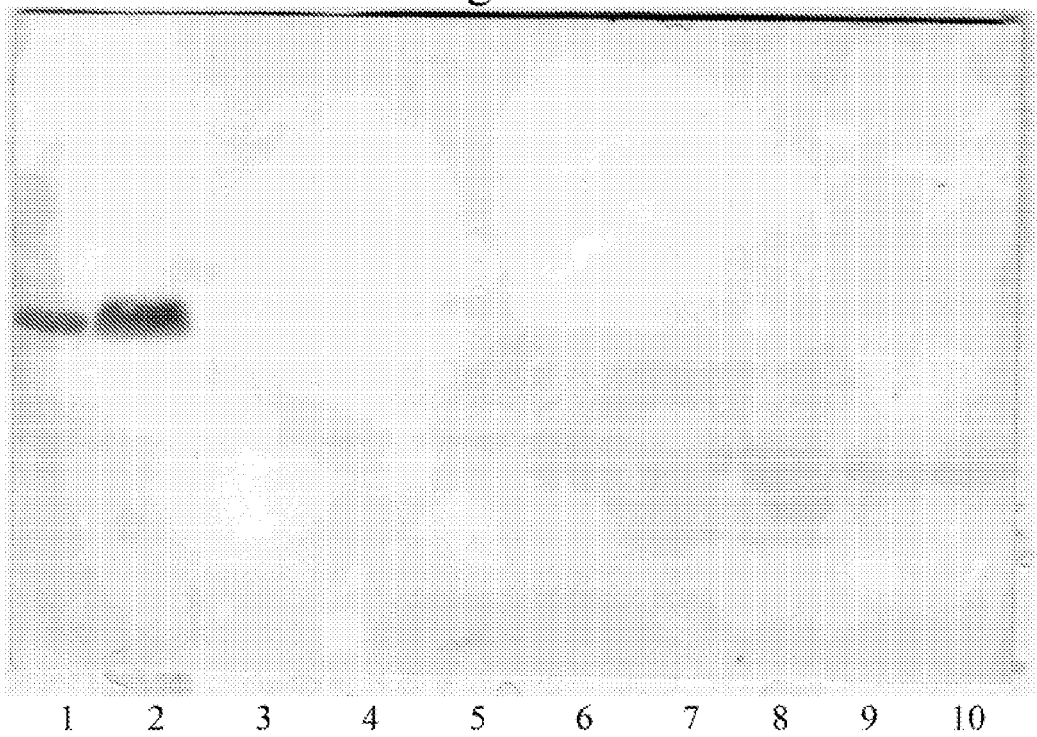
Figure 11E:
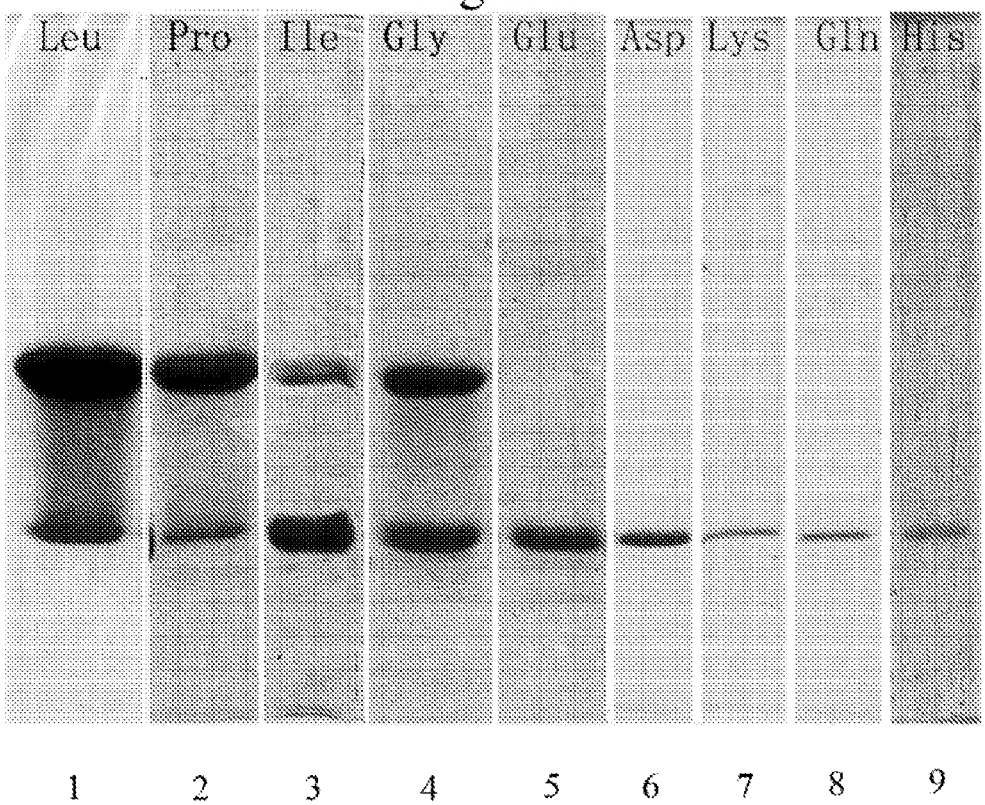

There was probably another reason that steric hindrance effect was generated when 8C11 and 8H3 bound NE2 simultaneously, thus the binding of antibodies recognizing the other epitopes adjacent to the two epitopes with their antigens. To find out the impact of such steric hindrance effect on blocking effects of MAbs 8C11 and 8H3, the Fab fragments of these two MAbs was excised by papain digestion to reduce markedly the steric hindrance effect, then the similar blocking experiment is performed. The result was shown in FIG. 9. The blocking effects of these Fab fragments were almost identical to that of the whole antibodies, which indicated that the blocking effects of MAbs 8C11 and 8H3 on the HEV-infected sera were epitope-specific. The evidently blocking effect of 8C11 and 8H3 against HEV-infected sera indicated that these two epitopes were the most important immuno-dominant epitopes within NE2 domain during HEV infection and their corresponding antibodies persisted for long time as main antibodies.

TABLE 12

The blocking effect of anti-NE2 MAbs against the sera at different phase of infected monkeys

| Sera | | Blocking rate (%) | | | | | | | | |
|---|---|---|---|---|---|---|---|---|---|---|
| | | 1F6 | 2C9 | 7E8 | 8C11 | 8H3 | 13D8 | 15B2 | 16D7 | 8C11 + 8H3 |
| F4 | 3 w | — | — | — | 98.4 | — | 98.4 | — | — | 98.4 |
| | 4.5 w | — | — | — | 91.4 | — | 83.0 | — | — | 97.7 |
| | 18 w | — | — | — | 77.8 | — | 70.8 | — | — | 90.9 |
| | 52 w | — | — | — | 50.7 | — | 61.0 | — | — | 87.5 |
| F6 | 4 w | 51.9 | — | — | 97.6 | — | 96.9 | — | — | 98.3 |
| | 6 w | — | — | — | 69.1 | — | 70.9 | — | — | 98.4 |
| | 13 w | — | — | — | 82.0 | — | 77.7 | — | — | 96.0 |
| F15 | 4 w | — | 51.5 | — | 84.8 | — | 73.2 | — | — | 83.3 |
| | 6 w | — | — | — | 74.9 | — | 67.8 | — | — | 97.9 |
| | 10 w | — | — | — | 68.1 | — | 66.5 | — | — | 93.0 |
| | 16 w | — | — | — | 70.9 | — | 68.9 | — | — | 94.0 |

—, blocking rate was below 50%.

5. The Isolation and Expression of Variable Region Genes of Heavy and Light Chains of Said Monoclonal Antibodies in the Present Invention Example 15

The Isolation of Variable Region Genes of Heavy and Light Chains of Monoclonal Antibody 13D8

$10^7$ hybridroma cells of 13D8 mouse origin were cultured to semi-confluent, suspended and then transferred into a new 4 ml centrifuge tube. The cells were collected by spinning at 1500 rpm for 3 min. The pellet was resuspended in 100 μl sterile PBS (pH7.45) and transferred into a new 1.5 ml centrifuge tube. 800 μl Trizol (Roche, Germany) was added to the tube. The solution was thoroughly mixed by gently inversion and allowed to stand for 10 min. The tube was vigorously shake for 15 seconds after adding 0.2 ml chloroform, and allowed to stand for 10 min, then centrifuged at 12000 rpm for 15 min at 4° C. The upper aqueous phase was transferred to a new 1.5 ml centrifuge tube follow by adding an equal volume of isopropanol. The tube was mixed by several inversions and stood for 10 min, then centrifuged at 12000 rpm for 10 min at 4° C. The supernatant was discarded. The pellet was washed by adding 600 ul of 75% ethanol. The tube was centrifuged at 12000 rpm for 5 min at 4° C. The supernatant was discarded. The pellet was dried under vacuum for 5 min at 60° C., then dissolved in 70 ul of DEPC $H_2O$. The solution was added with 1 ul reverse transcription primer Oligo(dT)$_{(12-18)}$ (Progega), 1 μl dNTP (Shenggong, Shanghai), then incubated in water bath at 72° C. for 10 min. The tube was immediately placed on ice for 5 min, added with 20 ul 5×RT buffer, 2 μl AMV (10 u/μl, Pormega) and 1 μl Rnasin (40 u/μl, Promega), then mixed. The cDNA was synthesized by reverse transcription at 42° C.

The antibody genes were isolated by the method of polymerase chain reaction (PCR) with Ig-Prime kits (Novagen) and another designed downstream primer MKCR1 (synthesized by Bioasia, Shanghai). The above synthesized 13D8 cDNA was used as template.

The light chain gene was isolated with seven sets of upstream primers of MuIgkV$_L$5'-A to G for Kappa chain and downstream primer MKCR1(5'-TCT AGA ATT AAC ACT CAT TCC TGT TGA A-3' (SEQ ID NO: 44)). Gradient PCR amplification was carried out from 47 to 56° C. with primer pairs composed of primer MKCR1 and each of the seven upstream primers. As a result, a single DNA fragment about 700 bp was amplified with primer pair of MuIgkV$_L$5'-G3 (5'-ATG GT(C/T) CT(C/T) AT(A/C/G) TT(A/G) CTG CTG CTA TGG-3' (SEQ ID NO: 45))/MKCR1 under the following PCR condition: 94° C. for 5 min followed by thirty-five cycles of 94° C. for 40 s, 53° C. for 1 min, 72° C. for 50 s and a final 72° C. for 15 min. The fragment was recovered and cloned into pMD 18-T vector and then sequenced (Bioasia, Shanghai). The sequence was identified as 13D8 light chain sequence after BLAST alignment. The variable region was set forth in SEQ ID NO:5, and its deduced amino acid sequence was in SEQ ID NO:6.

The variable region gene of the heavy chain was isolated using six sets of upstream primers of MuIgGVH5'-A to F for IgG and downstream primer MV$_H$R(5'-CCC AAG CTT CCA GGG (A/G)CC A(A/G)(G/T) GGA TA(A/G) AC(A/G/C/T) G(A/G)T GG-3' (SEQ ID NO: 46)). Gradient PCR amplification was carried out from 47 to 56° C. with primer pairs composed of primer MV$_H$R and each of the six upstream primers. As a result, a single DNA fragment about 400 bp was amplified with primer pair of MuIgGV$_H$5'-C2 (5'-CGA CAT GG(A/C/G) TTG G(C/G)T GTG GA(A/C) CTT GC(C/T) ATT CCT-3' (SEQ ID NO: 47))/MuIgGVH3'-2 under condition below: 94° C. for 5 min followed by thirty-five cycles of 94° C. for 40 s, 53° C. for 1 min, 72° C. for 40 s and a final 72° C. for 15 min. The fragment was recovered and cloned into pMD 18-T vector and then sequenced (Bioasia, Shanghai). The sequence was identified as variable region sequence of 13D8 heavy chain after BLAST alignment (SEQ ID NO:7) and its deduced amino acid sequence was in SEQ ID NO:8.

Example 16

Cloning, Expression, Purification and Activity Determination of 13D8 Single Chain Antibody The variable regions of 13D8 heavy and light chain were linked to form DNA fragment of single chain antibody by the short peptide linker of (GGGGS)$_3$. The DNA fragment of variable region of 13D8 heavy chain was amplified with primer pair of 13D8HF1(5'-gAA TTC gAT gTA CAA CTT CAg g-3' (SEQ ID NO: 48))/13D8HR1(5'-gCT ACC ACC CCC TCC AgA TCC gCC ACC TCC TgA AgA TAC ggT gAC CgT ggT gCC -3' (SEQ ID NO: 49)), and the DNA fragment of variable region of 13D8 light chain was amplified with primer pair of 13D8KF1(5'-A TCT ggA ggg ggT ggT AgC ggT ggA ggC ggg AgT gAC ATC CAg ATg ACT CAg-3' (SEQ ID NO: 50))/13D8KR1(5'-gTC gAC CCG TTT GAT TTC CAG C-3' (SEQ ID NO: 51)). These two fragments were respectively recovered and assembled into full length fragment of single chain antibody in a new PCR system with such two fragments as primers and template for each other. The few obtained full length fragment of single chain antibody was used as template to further amplify with primer pair 13D8HF1/13D8KR1. The recovered single chain antibody fragment was cloned into pMD 18-T vector. The single chain antibody fragment was recovered by digestion with EcoR I/Sal I from the resulted plasmid, then cloned into prokaryotic expression vector pTO-T7 digested with the same enzymes. The *E. coli* strain ER256 was transformed with the resulted recombinant plasmid pTO-T7-13D8, separate colony were picked and grown in 500 ml LB medium (with 100 ug/ml Kan). Incubations were carried out in a shaker overnight at 37° C. When the OD600 of the bacteria culture medium reached about 0.8, IPTG was added to a final concentration of 0.2 mmol/L for inducing, and the incubation was continued at 30° C. for 6 hours prior to harvesting bacteria and the bacteria were disrupted by sonication. After centrifugated at 15,000 rpm for 10 min, the precipitate was dissolved in the same volume of 20 mmol/L Tris-HCl (pH 7.6) as the supernatant. Equal volume of supernatant and precipitate solution were performed SDS-PAGE. The concentrations of stacking gels and resolving gels were 5% and 12% respectively. It was observed that the expressed protein mainly existed in the form of unsoluble inclusion body. The precipitate from sonication was washed twice with 2% Triton followed by being dissolved in 2M, 4M and 8M urea respectively and 12% SDS-PAGE for each of the dissolved solution was performed. The single chain antibody was found mainly dissolved in 8M urea. The single chain antibody dissolved in 8M urea was renatured by dialyzing against 1× PBS gradually. The pellet was discarded by centrifugation at 12000 rpm for 10 min. The activity of the obtained single chain antibody solution was assayed.

The activity of the preliminary purified 13D8 single chain antibody was detected by competition ELISA. The 96-well ELISA plate was coated with purified NE2 diluted in 1:40000 and blocked with BSA. 50 ul of above single chain antibody solution and 50 ul of HRP-labeled 13D8 monoclonal antibody in 1:500 dilution were added to the sample wells to be detected. 50 ul of 1× PBS solution and 50 ul of HRP-labeled 13D8 monoclonal antibody in 1:500 dilution were added into the wells as negative control. 50 ul of unlabeled 13D8 monoclonal antibody and 50 ul of HRP-labeled 13D8 monoclonal antibody in 1:500 dilution were added into the wells as positive control. Assays were carried out in triplicate. After mixing the plate was incubated at 37° C. for one hour, then added chromatogen A and B. Color was developed at 37° C. for 15 min. The reaction was stopped and the absorbance was measured in a microplate reader. As a result, the mean value of negative control was 2.955, and the mean value of positive control was 0.731, the mean value of the sample wells to be detected was 0.624. The results showed that the preliminary purified 13D8 single chain antibody has high activity.

Example 17

Isolation of Variable Region Gene of Light Chain and Fd Fragment of Heavy Chain of Monoclonal Antibody 8C11

Total RNA was extracted from $1 \times 10^7$ semi-confluent mouse origin hybridroma cells of 8C11 by the same method mentioned above, and the cDNA was synthesized by reverse transcription. Similarly, the antibody variable region genes were isolated by PCR with Ig-Prime kits (Novagen) and two other designed downstream primers MFdR1 and MFdR2 (Bioasia, Shanghai), and with above synthesized 8C11 cDNA as template.

The light chain variable region gene was isolated with seven sets of upstream primers of MuIgkV$_L$5'-A to G for Kappa chain and 3' primer MuIgkV$_L$3'-1(5'-CCC AAG CTT ACT GGA TGG TGG GAA GAT GGA-3' (SEQ ID NO: 52)). Gradient PCR amplification was performed from 47 to 56° C. with primer pairs composed of one downstream primer and each of the seven upstream primers. As a result, a single DNA fragment about 400 bp was amplified with primer pair of MuIgkV$_L$5'-G3/MuIgkV$_L$3'-1 under the following condition: 94° C. for 5 min followed by thirty-five cycles of 94° C. for 35 s, 53° C. for 1 min, 72° C. for 40 s and a final 72° C. for 15 min. The fragment was recovered and cloned into pMD 18-T vector and sequenced (Bioasia, Shanghai). The sequence was identified as 8C11 light chain variable region gene after BLAST alignment. The sequence was set forth in SEQ ID NO:9, and its deduced amino acid sequence was in SEQ ID NO:10.

The Fd fragment of the heavy chain gene was isolated using six sets of upstream primers of MuIgGV$_H$5'-A to F for IgG and downstream primer MFdR1(5'-ACT AGT ACA ATC CCT GGG CAC AAT-3' (SEQ ID NO: 53)) and MFdR2(5'-ACT AGT CTT GGG TAT TCT AGG CTC-3' (SEQ ID NO: 54)). Gradient PCR amplification was carried out from 47 to 56° C. with primer pairs composed of downstream primer MFdR1/MFdR2 and each of the six 5' primers. As a result, a single DNA fragment about 700 bp was amplified with primer pair of MuIgV$_H$5'-D1(5'-CGA CAT GAG G(A/G)C CCC TGC TCA G(A/T)T T(C/T)T TGG (A/TC/G)(A/T)T CTT-3' (SEQ ID NO: 55))/MFdR1 under the following condition: 94° C. for 5 min followed by thirty-five cycles of 94° C. for 40 s, 57° C. for 50 s, 72° C. for 50 s and a final 72° C. for 15 min. The fragment was recovered and cloned into pMD 18-T vector and sequenced (Bioasia, Shanghai). The sequence was identified as Fd fragment of 8C11 heavy chain after BLAST alignment and the part of the variable region sequence was set forth in SEQ ID NO: 11 and its deduced amino acid sequence was in SEQ ID NO:12.

Example 18

Cloning, Expression, Purification and Activity Determination of 8C11 Single Chain Antibody The variable regions of 8C11 heavy and light chain were linked to form DNA fragment of single chain antibody by the short peptide linker of (GGGGS)$_3$. The DNA fragment of variable region of 8C11 heavy chain was amplified with primer pair of 8c11HF1 (5'-ggA TCC CAT ATg CAg gTT ACT CTg AAA gAg-3' (SEQ ID NO: 56))/8c11HR1(5'-gCT ACC ACC CCC TCC AgA TCC gCC ACC TCC TgA ggA gAC ggC gAC TgA-3' (SEQ ID NO: 57)), and the DNA fragment of variable region of 8C11 light chain was amplified with primer pair of 8c11KF1(5'-A TCT ggA ggg ggT ggT AgC ggT ggA ggC ggg AgT gAC ATC CAg ATg ACT Cag-3' (SEQ ID NO: 58))/8c11KR1(5'-gTC gAC CCg TTT gAT TTC CAg CTT gg-3' (SEQ ID NO: 59)). These two fragments were recovered and assembled into full length fragment of single chain antibody in a new PCR system with the same fragments as primers and template for each other. The few obtained full length fragment of single chain antibody was further amplified with primer pair 8C11HF1/8C11KR1. The fragment of single chain antibody was recovered and cloned into pMD 18-T vector. The single chain antibody fragment was digested from the resulted plasmid with BamHI/Sal I and recovered, then cloned into prokaryotic expression vector pTO-T7 digested with the same enzymes. E. coli strain ER2566 was used to express single chain antibody with the similar process mentioned above. The expressed protein was found in the form of unsoluble inclusion body. The sonication precipitate was purified through the same process described above. The single chain antibody mainly dissolved in 8M urea. The single chain antibody dissolved in 8M urea was renatured by being dialyzed against 1× PBS gradually. The pellet was discarded by centrifugation at 12000 rpm for 10 min. The activity of the obtained single chain antibody was detected.

A competition ELISA was used to detect the activity of the preliminary purified 8C11 single chain antibody. The 96-well ELISA plate was coated with purified NE2 diluted in 1:160000 and blocked with BSA. 50 ul of above single chain antibody solution and 50 ul of HRP-labeled 8C11 monoclonal antibody in 1:1000 dilution were added to the sample wells to be detected. 50 ul of 1× PBS solution and 50 ul of HRP-labeled 8C11 monoclonal antibody in 1:1000 dilution was added the wells used as negative control and 50 ul unlabeled 8C11 monoclonal antibody and 50 ul of HRP-labeled 8C11 monoclonal antibody in 1:1000 dilution was added the wells used as positive control. Assays were carried out in triplicate. After mixing the plate was incubated at 37° C. for one hour, then added chromatogen A and B. Color was developed at 37° C. for 15 min. The reaction was stopped and the absorbance was measured in a microplate reader. As a result, the mean value of negative control was 1.852, and the mean value of positive control was 0.541, the mean value of the sample wells to be detected was 0.162. The results demonstrated that the preliminary purified 8C11 single chain antibody has high activity.

Example 19

Isolation of Monoclonal Antibody 8H3 Fab Gene (Light Chain and Fd Fragment of Heavy Chain)

Total RNA was extracted from $1 \times 10^7$ semi-confluent mouse origin hybridoma cells of 8C11 by the same method mentioned above, and the cDNA was synthesized by reverse transcription. Similarly, the antibody variable region genes were isolated by PCR with Ig-Prime kits (Novagen) and two other designed downstream primers MFdR1 and MFdR2 (Bioasia, Shanghai), and with above synthesized 8C11 cDNA as template.

The light chain gene was isolated with seven sets of upstream primers of MuIgkV$_L$5'-A to G for Kappa chain and downstream primer MKCR1. As a result, a single DNA fragment about 700 bp was amplified with primer pair of MuIgkV$_L$5'-G2(5'-CGA CAT GGT (C/T)CT (C/T)AT (A/C/G)TC CTT GCT GTT CTG G-3' (SEQ ID NO: 60))/MKCR1 under the following condition: 94° C. for 5 min followed by thirty-five cycles of 94° C. for 40 s, 56° C. for 35 s, 72° C. for 50 s and a final 72° C. for 15 min. The fragment was recovered and cloned into pMD 18-T vector and sequenced (Bioasia, Shanghai). The sequence was identified as 8H3 light chain sequence after BLAST alignment. The sequence of the variable region was set forth in SEQ ID NO:13, and its deduced amino acid sequence was in SEQ ID NO: 14.

The Fd fragment of the heavy chain gene was isolated using six sets of upstream primers of MuIgGV$_H$5'-A to F for IgG and downstream primer MFdR1 and MFdR2. As a result, a single DNA fragment about 700 bp was amplified with primer pair of MuIgV$_H$5'-C1(5'-CGA CAT GGC TGT C(C/T)T (A/G)G(C/G/T) GCT G(C/T)T C(C/T)T CTG-3' (SEQ ID NO: 61))/MFdR1 under the following condition: 94° C. for 5 min followed by thirty-five cycles of 94° C. for 40 s, 50° C. for 1 min, 72° C. for 50 s and a final 72° C. for 15 min. The fragment was recovered and cloned into pMD 18-T vector and sequenced (Bioasia, Shanghai). The sequence was identified as Fd fragment of 8H3 heavy chain after BLAST alignment and the part of the variable region sequence was set forth in SEQ ID NO:15 and its deduced amino acid sequence was in SEQ ID NO:16.

Example 20

Isolation of Monoclonal Antibody 16D7 Fab Gene (Light Chain and Fd Fragment of Heavy Chain)

Total RNA was extracted from 1×10$^7$ semi-confluent mouse origin hybridoma cells of 8H3 by the same method mentioned above, and the cDNA was synthesized by reverse transcription. Similarly, the Fab fragment of the antibody gene was isolated by PCR with Ig-Prime kits (Novagen) and three downstream primers of MFdR1, MFdR2 and MKCR1 (Bioasia, Shanghai), and with above synthesized 8H3 cDNA as template.

The light chain gene was isolated with seven sets of upstream primers of MuIgkV$_L$5'-A to G for Kappa chain and downstream primer MKCR1. As a result, a single DNA fragment about 700 bp was amplified with primer pair of MuIgkVL5'-F4(5'-CGA CAT GAA GTT GCC TGT TAG GCT GTT GGT GCT-3' (SEQ ID NO: 62))/MKCR1 under the following condition: 94° C. for 5 min followed by thirty-five cycles of 94° C. for 40 s, 57° C. for 35 s, 72° C. for 50 s and a final 72° C. for 15 min. The fragment was recovered and cloned into pMD 18-T vector and sequenced (Bioasia, Shanghai). The sequence was identified as 16D7 light chain sequence after BLAST alignment and the part of the variable region sequence was set forth in SEQ ID NO:17, and its deduced amino acid sequence was in SEQ ID NO: 18.

Gradient PCR amplification was carried out from 47 to 56° C. with primer pairs composed of downstream primer MFdR1/MFdR2 and each of the six upstream primers. As a result, a single DNA fragment about 700 bp was amplified with primer pair of MuIgV$_H$5'-E2 (5'-CGA CAT GG(A/G) ATG GA(C/G) C(G/T)(G/T) (A/T/C/G)(A/G)T CTT T(A/C)T CT-3' (SEQ ID NO: 63))/MFdR1 under the following condition 94° C. for 5 min followed by thirty-five cycles of 94° C. for 40 s, 54° C. for 1 min, 72° C. for 50 s and a final 72° C. for 15 min. The fragment was recovered and cloned into pMD 18-T vector and sequenced (Bioasia, Shanghai). The sequence was identified as Fd fragment of 16D7 heavy chain after BLAST alignment and the part of the variable region sequence was set forth in SEQ ID NO:19 and its deduced amino acid sequence was in SEQ ID NO:20.

Example 21

The Expression and Activity Assay of 8C11 Human-mouse Chimeric Antibody in CHO Cells The variable regions of the light and heavy chain of 8C11 mouse antibody gene were respectively fused with the constant regions of light and heavy chain of human antibody gene. After expressed in CHO cells, the whole human-mouse chimeric antibody can be assembled and secreted into the supernatant of the cell culture. The expression vectors used therein were two types of plasmids of mammalian expression vector pcDNA3.1-Hyg (hygromycin as selective marker) and pcDNA3.1-Neo (neomycin as selective marker).

Four primers were synthesized. The constant region gene of human kappa light chain was amplified by PCR with hKCF (5'-CTC gAg ACT gTg gCT gCA CCA TC-3' (SEQ ID NO: 64))/hKCR(5'-ggA TCC TCT AgA TTA ACA CTC TCC CCT gTT g-3' (SEQ ID NO: 65)) as primer pair and plasmid pAG4622 as template, and cloned into pMD18-T vector. The fragment cut off and recovered from the resulted plasmid with Xho I/Xba I was cloned into pcDNA3.1-Neo vector digested with the same enzymes to generate plasmid pcDNA3.1-Ak. The constant region gene of human gamma 1 heavy chain was amplified by PCR with hHCF(5'-CTC gAg gCA AgC TTC AAg ggC C-3' (SEQ ID NO: 66))/hHCR(5'-ggA TCC TCT AgA TTA TTT ACC Cgg AgA CAg g-3' (SEQ ID NO: 67)) as primer pair and plasmid pAH4604 as template, and cloned into pMD18-T vector. The fragment cut off and recovered from the resulted plasmid with Xho I/Xba I was cloned into pcDNA3.1-Hyg vector digested with the same enzymes to generate plasmid pcDNA3.1-AH.

The variable region of 8C11 light chain with signal peptide was amplified by PCR with 8C11hVkF(5'-gAA TTC ATG AGT GTG CCC ACT CAG GTC CTG GGG TTG CTG CTG CTG TGG CTT ACA GAT GCC AGA TGT GAC ATC CAG ATG ACT CAG-3' (SEQ ID NO: 68))/8C11hVkR(5'-CTC gAg CCg TTT gAT TTC CAg CTT gg-3' (SEQ ID NO: 69)) as primer pair and pMD18-T vector containing 8C11 light chain gene obtained from example 17 as template. This DNA fragment was cloned into pMD18-T vector and further cut off from the resulted plasmid with EcoR I/Xho I, then cloned into the same sites of plasmid pcDNA3.1-Ak to generate plasmid pcDNA3.1-Ak8C expressing human-mouse chimeric light chain.

The variable region of 8C11 heavy chain with signal peptide was amplified by PCR with 8C11hVhF(5'-gAA TTC AgA TCT ATG GGC AGG CTT ACT TCT TCA TTC CTG CTA CTG ATT GTC CCT GCA TAT GTC CTG TCC CAG GTT ACT CTG AAA GAG TC-3' (SEQ ID NO: 70))/8C11hVhR(5'-CTC gAg TGA GGA GAC GGC GAC TG-3' (SEQ ID NO: 71)) as primer pair and pMD18-T vector containing 8C11 heavy chain Fd gene obtained from example 17 as template. This DNA fragment was cloned into pMD18-T vector and further cut off from the resulted plasmid with Bgl II/Xho I, then cloned into plasmid pcDNA3.1-AH digested with BamH I/XhoI to generate plasmid pcDNA3.1-AH8C expressing human-mouse chimeric heavy chain.

These two plasmids pcDNA3.1-Ak8C and pcDNA3.1-AH8C were co-transfected into mammalian CHO cells by liposome mediated transfection. The liposome was Lipofectamine™ Reagent from Invitrogen. The transfected cells were cultured in 24-well plate for 2 days and then transferred to 6-well plate with less then 100 cells per well. Hygromycin and neomycin were simultaneously added to culture medium for selection. Two weeks latter, culture supernatant and partial cells were collected. The cells were disrupted by repeatedly freezing and thawing for 4 times, and the cell supernatant was collected by centrifuging. Indirect ELISA was used to detect the activity of supernatant with the untransfected CHO cells by same treatment as negative control.

The 96-well ELISA plate was coated with antigen NE2 and blocked with BSA. 100 ul of sample was added in triplicate, as well as the negative control. The plate was incubated at 37° C. for one hour. After washing, each well was added with 100 ul of HRP-labeled goat anti-human IgG antibody in 1:5000 dilution. The plate was incubated at 37° C. for half an hour. After washing, the chromatogen A and chromatogen B were added and color was developed at 37° C. for 15 min. The reaction was stopped and the absorbance was measured by a microplate reader. The results showed that the mean value of culture supernatant of cells as negative control was 0.093, while the mean value of culture supernatant of the cells expressing 8C11 human-mouse chimeric antibody was 2.346. The mean value of supernatant of the disrupted cells as negative control was 0.132, while the mean value of supernatant of the disrupted cells expressing 8C11 human-mouse chimeric antibody was 3.534.

The above results demonstrated that 8C11 human-mouse chimeric antibody expressed by CHO cells can be correctly assembled within cells and secreted out of the cells with high activity.

6. Identification of a Recombinant Polypeptide HEV ORF2 Having Epitopes Recognized by a Monoclonal Antibody, and Preparation of the Polypeptides or Polypeptide Analogs Having the Antigenic Determinant Property (esp. Having the Property of Assembling into Virus-like Particles) According to the Present Invention, Example 22

Interaction of NE2-like Recombinant Polypeptides HEV ORF2 and Monoclonal Antibodies The HEV ORF2 polypeptides (listed in Table 13) were cloned into pTO-T7 vector, expressed and purified according to methods of Example 1. The expressed recombinant HEV ORF2 polypeptides were detected by ELISA using HRP-labeled monoclonal antibody according to methods of example 2.

10 µl (1 mg/ml) of each of the purified polypeptides was dotted repeatedly and slowly on the nitrocellulose membrane and air-dried. After blocking with 5% skim milk for 1.5 hours at room temperature, the monoclonal antibodies (the cell supernatant secreted by monoclonal B lymphocytes at 1:100 dilution with 5% skim milk) were added, and kept for reacting at room temperature for 1 hour. Then the membrane was washed 3 times (with 5 mins interval) using TNT (10 mM Tris.Cl, pH8.0, 150 mM NaCl, 0.05% Tween20). The HRP-labeled Goat anti-mouse IgG (produced by JINGMEI Biological Company, diluted at 1:1000 with 5% skim milk) was added, and reacted at room temperature for 1 hour. After washing 3 times (with 5 mins interval) with TNT, NBT/BCIP ($C_{40}H_{30}N_{10}O_6Cl_2/C_8H_6BrClNO_4P.C_7H_9N$) was added to develop color. The developed dots were scanned with UVI gel imagining system and converted into the values of grey degree, which is divided into five positive grades as ++++, +++, ++, +, +/− and negative grade as −. The results were listed in Table 13, which showed that the polypeptide 148C (459-603PPR) and 208N (394-601) were reactive with monoclonal antibodies 8C11, 8H3 and 13D8. Thus the epitope region recognized by monoclonal antibodies 8C11, 8H3 and 13D8 were speculated to locate in the overlapping region 459-601 of above-mentioned two polypeptides. To locate the epitope region recognized by monoclonal antibody 16D7, other polypeptides 97C (AA564-AA660), 161 (AA499-AA660) and 170P (AA345-AA515) were tested for activities with monoclonal antibody 16D7. The results showed that 97C was not reactive with 16D7, while 161 and 170P was reactive with 16D7. This result indicated that the epitope region recognized by 16D7 might locate in AA499-515 of HEV ORF2. The polypeptides, with excellent antigenicities with monoclonal antibody 8C11, 8H3 and 13D8, were mostly present as dimer on SDS-PAGE, which suggested that formation of a dimer favors the proper folding and/or complete exposure of epitopes for the three monoclonal antibodies.

TABLE 13 interactions of NE2-like recombinant polypeptide HEV ORF2 and monoclonal antibodies

| peptide | N-terminal | C-terminal | Momomer percent | Dimer percent | ELISA | | | | Dot blotting | | |
|---|---|---|---|---|---|---|---|---|---|---|---|
| | | | | | 8C11 | 8H3 | 13D8 | 16D7 | 8C11 | 8H3 | 13D8 |
| NE2* | 394 | 603 | 10% | 90% | ++++ | + | ++++ | ++++ | ++++ | ++ | +++ |
| 193C* | 414 | 603 | 5% | 95% | ++++ | + | +++ | ++++ | ++ | ++ | ++ |
| 178C* | 429 | 603 | 100% | 0% | +++ | − | +++ | ++++ | ++ | ++ | ++ |
| 168C* | 439 | 603 | 100% | 0% | ++++ | − | ++++ | ++ | +/− | +/− | +/− |
| 158C* | 449 | 603 | 60% | 40% | +++ | + | ++++ | ++ | + | +/− | +/− |
| 148C* | 459 | 603 | 100% | 0% | +++ | + | +++ | ++ | +/− | +/− | +/− |
| 138C* | 469 | 603 | 100% | 0% | − | − | − | ++ | +/− | +/− | +/− |

TABLE 13-continued

| | interactions of NE2-like recombinant polypeptide HEV ORF2 and monoclonal antibodies | | | | | | | | | | |
|---|---|---|---|---|---|---|---|---|---|---|---|
| | N- | C- | Momomer | Dimer | ELISA | | | | Dot blotting | | |
| peptide | terminal | terminal | percent | percent | 8C11 | 8H3 | 13D8 | 16D7 | 8C11 | 8H3 | 13D8 |
| NE2I | 394 | 606 | 5% | 95% | ++++ | +/− | +++ | ++++ | +++ | ++ | +++ |
| 217I | 390 | 606 | 85% | 15% | +++ | +/− | ++ | +++ | + | + | + |
| 193I | 414 | 606 | 100% | 0% | +++ | +/− | +++ | ++++ | +++ | ++ | +++ |
| 178I | 429 | 606 | 60% | 40% | +++ | +/− | +++ | +++ | ++ | ++ | ++ |
| NE2D | 394 | 603 | 80% | 20% | +++ | +/− | +++ | +++ | + | + | + |
| 217D | 390 | 603 | 20% | 80% | +++ | +/− | +++ | +++ | + | + | + |
| 193D | 414 | 603 | 100% | 0% | +++ | +/− | +++ | +++ | + | + | + |
| 178D | 429 | 603 | 100% | 0% | ++ | − | ++ | +++ | + | + | + |
| 266N | 394 | 660 | 20% | 80% | +++ | + | +++ | +++ | ++++ | ++ | +++ |
| 235N | 394 | 628 | 10% | 90% | +++ | + | +++ | +++ | +++ | + | +++ |
| 225N | 394 | 618 | 4% | 96% | +++ | + | +++ | +++ | ++++ | + | +++ |
| 209N | 394 | 602 | 25% | 75% | ++ | +/− | +++ | +++ | ++++ | + | +++ |
| 208N | 394 | 601 | 100% | 0% | ++ | − | ++ | +++ | ++ | + | ++ |
| 207N | 394 | 600 | 100% | 0% | − | − | − | +++ | ++ | + | + |
| 203N | 394 | 596 | 100% | 0% | − | − | − | +++ | ++ | + | + |
| 193N | 394 | 586 | 100% | 0% | − | − | − | +++ | ++ | + | + |
| 176N | 394 | 569 | 100% | 0% | − | − | − | +++ | + | +/− | + |
| 205 | 414 | 618 | 10% | 90% | +++ | + | +++ | +++ | +++ | ++ | ++ |
| 189 | 414 | 602 | 2% | 98% | ++ | +/− | + | +++ | ++ | ++ | ++ |
| 188 | 414 | 601 | 4% | 94% | + | +/− | + | +++ | ++ | ++ | ++ |
| 173 | 414 | 586 | 100% | 0% | − | − | − | +++ | ++ | + | ++ |
| 201 | 459 | 660 | 1% | 99% | +++ | + | +++ | + | ++++ | ++ | ++++ |
| 222 | 439 | 660 | 10% | 90% | +++ | + | +++ | ++ | ++++ | ++ | ++++ |
| 232 | 429 | 660 | 10% | 90% | +++ | + | ++ | +++ | ++++ | ++++ | ++++ |
| 247 | 414 | 660 | 10% | 90% | +++ | + | +++ | +++ | ++++ | +++ | ++++ |
| N160 | 459 | 618 | 100 | 0 | ++ | − | ++ | + | ++ | − | ++ |
| 170 | 459 | 628 | 100 | 0 | +++ | − | +++ | ++ | ++++ | ++ | ++++ |
| 150 | 469 | 618 | 100 | 0 | − | − | − | ++ | − | − | − |
| 134 | 469 | 602 | 100 | 0 | − | − | − | ++ | − | − | − |

The symbol * means that -P-P-R was added to the C-terminal of the polypeptide sequence.

Interactions of polypeptides and monoclonal antibodies can be ranked from − to ++++ by calculating the P/N ratio, i.e. the ratio of OD value of sample well to OD value of negative control well (if the OD value of negative control well is less than 0.05, then 0.05 is designated to the negative OD value). So the ranks is defined as following: − (i.e. negative), P/N<3; +/−, 3<P/N6; +, 6<P/N<10; ++, 10<P/N<30; +++, 30<P/N<50; ++++, P/N>50.

Example 23

Expression of Mutants Derived from Mutations on NE2 Polypeptide's Dimerization Region and their Antigenicities Against Monoclonal Antibodies The NE2 was recognized more strongly in its dimeric form than the monomer form by monoclonal antibody 8C11, 8H3 and 13D8. The dimer can be completely dissociated into monomers with 8 mol/L urea treatment, and then the antigenicities against monoclonal antibody 8C11, 8H3 and 13D8 were significantly reduced. This phenomena suggested that the proper folding and/or complete exposure of epitope on NE2 recognized by monoclonal antibody 8C11, 8H3 and 13D8 was closely correlated with the homo-dimerization of NE2 polypeptide, and such homo-dimerization may depend on hydrophobic interaction of monomers.

The mutants, derived from NE2 by truncating the C-terminal to AA600, were not able to dimerizing, and had significantly reduced antigenicities against monoclonal antibody 8C11, 8H3 and 13D8. This indicated that the region located near AA600 play a critical role in dimerization of NE2 and analogs thereof. To verify this speculation, a serial of site-directed mutation were introduced in the AA600 region.

The NE2 polypeptide underwent site-directed mutation by PCR and cloning techniques, and the key site for dimerization was identified by observing the presence of dimerization. Firstly, Leu on AA601 was substituted with Ile, Pro, Glu, Gly, Asp, His, Lys, Gln, and Cys, respectively. The methods are described in detail as follows:

To get a AA601-mutated C-terminal, polymerase chain reaction (PCR) was performed with NE2 as a template, 601LIFP (a primer of which Leu mutated to Ile) as upstream primer, and HERP as downstream primer. And a secondary PCR was performed with NE2 as a template, HEFP as upstream primer, and the recovered mutated C-terminal fragment as downstream primer. The amplified full length NE2 mutant was named as 601LI, which was then linked into the vector pMD18-T, and then digested with BamH I/Hind III, identifying a positive clone pMD 18-T-601LI. This clone was digested with NdeI and EcoRI to obtain the interested 601LI gene, which was then cloned into NdeI/EcoRI-digested pTO-T7. The clone identified as having correct insertion was pTO-T7-601LI, and the expressed protein was 601LI.

Similarly, other mutant 601LP, 601LE, 601LG, 601LD, 601LH, 601LK, 601LQ and 601LC were obtained. The properties of the mutated proteins were shown in FIG. 10.

Through SDS-PAGE, polypeptides 601LI, 601LP, 601LG, and 601LC were found to form dimers, but polypeptides 601LE, 601LD, 601LH, 601LK and 601KQ were present as monomers (Table 14 and FIG. 11). The results showed that, the polypeptides of which AA601 was nonpolar amino acid can form dimers and have good antigenicities against monoclonal antibody 8C11, 8H3 and 13D8; and the polypeptides of which AA601 was polar amino acid failed in dimerizing and have reduced antigenicities against monoclonal antibody 8C11, 8H3 and 13D8. Seven continuous nonpolar amino acids were found to be located at AA597-AA603 (including AA601), which were speculated to play a key role in dimerization of NE2 polypeptide. To verify this speculation, the amino acids located at AA596-AA603 of NE2 were substituted with nonpolar amino acid E individually, resulting in the mutants 596SE, 597AE, 598VE, 599AE, 600VE, 602AE and 603PE. Of these mutants, 596SE, 600VE and 603PE could form dimers, while 597AE, 598VE, 599AE and 602AE were present in monomers (Table 14). The dimerized mutants kept strong antigenicities against monoclonal antibody 8C11, 8H3 and 13D8, whereas the mutants present in monomers have obviously reduced antigenicities. Except the substitution of V by A at AA600, the substitutions of nonpolar amino acids by polar amino acids in AA597-AA602 region all inhibited the dimerization and thus reduced the antigenicities against 8C11, 8H3 and 13D8. In addition, the mutation to AA596(S) (outside of AA597-AA602 region) had no effect on dimerization and antigenicity.

These results strongly suggested that the nonpolar region AA597-AA603 of NE2 and analogs thereof plays a key role not only in dimerization, but also in proper folding and/or exposure of their epitopes recognized by monoclonal antibody 8C11, 8H3 and 13D8.

PCR was performed to get polynucleotide sequence encoding polypeptide 239 (AA368-AA603PPR) with pTO-T7-NE2 as a template. The primers were as follows:

```
390FP:
5'-CAT ATG TCG GCG GGT GGT CAG CTG (SEQ ID NO: 72)
TTC TAC TCT CGC-3'

380FP:
5'-CAT ATG CTA GGC GGT CTA CCC ACA (SEQ ID NO: 73)
GAA TTG ATT TCG TCG GCG GGT GGT C-
3'

368FP:
5'-CAT ATG ATA GCG CTT ACC CTG TTT (SEQ ID NO: 74)
AAC CTT GCT GAC ACC CTG CTA GGC
GGT CTA CCC A-3'

EHERP:
5'-GAA TTC ACC ACC ATG ATA GCG CTT (SEQ ID NO: 75)
ACC CTG TTT-3'
```

The first polymerase chain reaction (PCR) was performed with pTO-T7-NE2 as template, together with the following two primers: forward primers 390FP, in which Nde I restriction site was introduced to 5'; and reversed primer EHERP, in which EcoR I site was introduced to 5'. The reaction condition was as follwing: 94° C. 5 min; then 30 cycles of: 94° C. 50 sec, 57° C. 50 sec and 72° C. 1 min; extension at 72° C. for 10 min. A specific DNA fragment about 810 bp was obtained, i.e. the DNA encoding AA390-AA603PPR polypeptide. This PCR product was further linked into the vector pMD18-T, and the positive clone pMD 18-T-390F inserted with interest gene was then identified by digestion with BamH I/Hind III. The secondary PCR was performed with pMD 18-T-390F as template, together with forward primer 380FP (of which a NdeI site was introduced to 5') and reversed primer EHERP. The resultant fragment was about 840 bp in length, which encoded a polypeptide located on AA380-AA660 of HEV ORF2. Similarly, the PCR product was linked to vector pMD 18-T, and the positive clone pMD 18-T-380F was identified by digestion with BamH I/Hind III. The similar predure was repeated. Thereby the gene 239 (AA368-603PPR) was obtained by PCR with forward primer 368FP and reverse

TABLE 14 dimerizations and antigenicities against monoclonal antibodies of polypeptides resulted from site-directed mutation on NE2 dimerizing region

| | | WB | | | | ELISA | | | | |
|---|---|---|---|---|---|---|---|---|---|---|
| polypeptide | dimerization | 8C11 | 8H3 | 13D8 | 16D7 | 8C11 | 8H3 | 13D8 | 16D7 | 8C11 increases 8H3's reactivity |
| NE2 | Yes | +++ | +++ | ++++ | ++++ | ++++++ | | ++++ | ++++ | ×10 |
| 601LI | Yes | +++ | +++ | ++++ | ++++ | ++++++ | | ++++ | ++++ | ×10 |
| 601LP | Yes | +++ | +++ | ++++ | ++++ | +++ | ++ | +++ | ++++ | ×10 |
| 601LG | Yes | +++ | +++ | ++++ | ++++ | ++++++ | | ++++ | ++++ | ×10 |
| 601LC | Yes | +++ | +++ | ++++ | ++++ | +++ | ++ | +++ | ++++ | ×10 |
| 601LE | No | + | ± | + | +++ | ± | ± | ± | ++++ | ×1 |
| 601LD | No | + | ± | + | +++ | ± | ± | ± | ++++ | ×1 |
| 601LH | No | + | ± | + | +++ | ± | ± | ± | ++++ | ×1 |
| 601LK | No | + | ± | + | +++ | ± | ± | ± | ++++ | ×1 |
| 601LQ | No | + | ± | + | +++ | ± | ± | ± | ++++ | ×1 |
| 596SE | Yes | | | | | +++ | ++ | +++ | ++++ | ×1 |
| 597AE | No | + | + | + | ++++ | + | ± | ± | ++++ | ×1 |
| 598VE | No | + | + | ++ | ++++ | + | ± | + | ++++ | ×1 |
| 599AE | No | + | + | + | ++++ | + | ± | ± | ++++ | ×1 |
| 600VE | Yes | +++ | +++ | ++++ | ++++ | ++++++ | | ++++ | ++++ | ×5 |
| 602AE | No | + | + | + | ++++ | + | ± | ± | ++++ | ×1 |
| 603PE | Yes | | | | | +++ | ++ | +++ | ++++ | ×5 |

Example 24

Clone Construction of Polypeptide 239

According to the MALDI-TOF-MS analysis of polypeptide NE2 described in Example 1, this polypeptide can spontaneously form several kinds of homopolymers in solution. To some extent, the polymerization procedure of polypeptide NE2 might mimic self-assemble of HEV capsid, and the dimers might present the basic structural units of HEV particles.

To express VLPs of HEV in *E. coli*, N-terminal of NE2 of pTO-T7-NE2 was extended to AA368 by means of primer-extension synthesis, resulting in clone pTO-T7-239. pTO-T7-239 could express a recombinant polypeptide with amino acid sequence of SEQ ID No: 21.

primer EHERP. The amplified gene 239 was linked to the vector pMD18-T, and the positive clone pMD 18-T-239 was then identified by digestion with BamH I/Hind III. The pMD 18-T-239 was digested with Nde I and EcoR I to obtain gene 239 of interest, which was then cloned into NdeI/EcoRI-digested pTO-T7. The positive clone pTO-T7-239 with correct insertion was identified.

Example 25

Expression and Purification of Polypeptide 239

E. coli ER2566 was transformed with pTO-T7-239, and incubated in a tube until OD of the culture reached about 1.0. Then the bacterium was used as a seed for future fermentation. 100 uL of the bacterium was added into 500 mL LB culture medium. After incubating at 37° C. for about 9 hours, 300 uL of 0.5M IPTG was added to induce the expression of 239. The mixture was incubated for another 4 hours. It was found that the expressed polypeptide 239 was present as inclusion body. Then the inclusion body was washed as followings:

The culture medium of E. coli was centrifuged at 8,500 rpm for 10 minutes, and the pellet was collected. The pellet obtained from 1,000 mL culture was re-suspended in 50 mL lysis buffer, and the cells were sonicated in ultrasonic instrument. The sonicated mixture was centrifuged, and the pellet was then re-suspended in 50 mL of 2% Triton, which was then shaken for 1 hour. The mixture was centrifuged again, and the pellet was re-suspended in 50 mL Buffer I solution, which was then sonicated for 5 min. The mixture was centrifuged. Then the pellet was re-suspended in 50 mL of 2% Triton, and shaken for 1 hour. After that, the mixture was centrifuged, and the pellet was re-suspended in 50 mL of Buffer I. After that the mixture was centrifuged. The pellet was re-suspended in 30 mL buffer I containing 2M Urea, sonicated for 1 min and agitated for 30 min. The mixture was centrifuged, and the supernatant was collected. The pellet was re-suspended in 30 mL Buffer I containing 4M Urea, sonicated for 1 min and agitated for 30 min. Then the mixture was centrifuged, and the supernatant was collected. The pellet was re-suspended in 20 mL Buffer I containing 8M Urea, sonicated for 1 min and agitated for 30 min. The mixture was then centrifuged, and the supernatant was collected. At last, the polypeptide 239 was found to be mainly dissolved in Buffer I containing 4M urea, which was further purified by isoelectro-focusing technique.

The systems used in the above method were as follows: pI8 IsoPrime Multi-chambered Electrofocusing unit (Amershan Pharmacia company); Immobilized pH membranes: pH5.10 (T %: 10%, C %: 8%), pH5.20 (T %: 5%, C %: 8%), pH5.25 (T %: 5%, C %: 8%), pH5.30 (T %: 5%, C %: 8%), pH5.35 (T %: 5%, C %: 8%), pH5.40 (T %: 10%, C %: 8%); reservoir solution: 4 mol/L urea in ultra-purified $H_2O$; Sample: a denatured solution (300 ml, 3.0 mg/mL) containing recombinant polypeptide dissolved in 4 mol/ml Urea; Sampled chamber was at pH5.25-pH5.30; Electrofocusing parameter: 200V 2 hr, 500V 2 hr, 800V 2 hr, 3000V 60 hr. The purified polypeptide was located between pH5.25 and pH5.30, with 300 ml in volume and 2.5 mg/ml in concentration. The purity was 95% as shown on silver-stained SDS-PAGE. The thus obtained polypeptide 293 was further purified by HPLC HIC (hydrophobic interaction chromatography), described as followings.

Instrument: Beckman System Gold Nouveau 125NMP/166NMP HPLC; Column: TSK Phenyl-5PW 21.5 mm×15 cm; Buffer: 0.5 mol/mL ammonium sulfate, 4 mol/L urea and 20 mmol/L phosphate buffer (pH7.2) ; Eluting buffer: 4 mol/mL urea, 20 mmol/mL phosphate buffer (pH7.2); Flow rate: 4 mL/min; Eluting mode: 0.5-0 mol/mL ammonium sulfate in continuous graduation for 120 min; Detection wavelength: 280 nm; Sample: 360 ml polypeptide 239 purified by isoelectrofocus at concentration 2 mg/ml; Collection: after 105-120 min on chromatography, 60 mL high-purified polypeptide 239 was obtained with concentration as 4 mg/mL, and the purity was more than 98% as shown on silver-stained SDS-PAGE.

Renaturation of Recombinant Polypeptide 239 Using Tangential Flow Device

Instrument: Tangential Flow Device system (PALL company); Cutoff MW of membrane: 30 kD; Running pressure: 5 psi; Flow rate: 500 mL/min; Tangential flow rate: 15 mL/min; Sample: 60 mL polypeptide 239 with concentration as 4 mg/mL, high-purified by HPLC HIC; Renaturation buffer: 1200 mL PBS (pH7.45); Post-treatment of renaturalized sample: 12,000 rpm centrifugation at 4° C. for 10 min, resulting in 60 mL renaturalized polypeptide with concentration as 3.9 mg/ml.

Example 26

Characterization of Virus-like Particles Self-assembled from Polypeptide 239

Figure 12A:
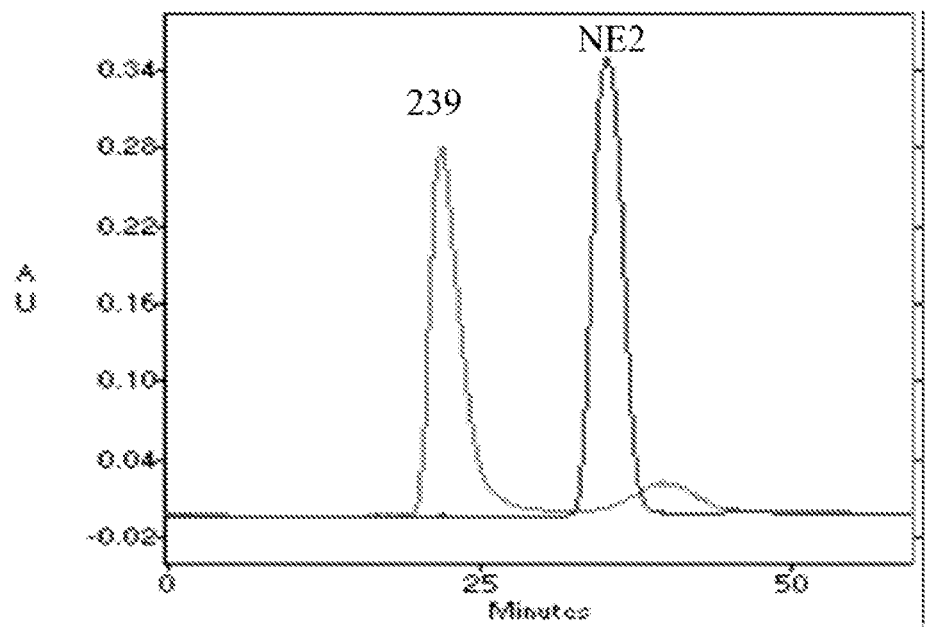
FIG. 12 shows the transmission electron microscopy of recombinant polypeptide 239.

Size Exclusion HPLC: sample 239 in 4M Urea/Buffer I was dialyzed against PBS, then loaded into TSK GEL SW3000 (21.5 mm×60 cm) column on Beckman System Gold Nouveau 125NMP/166NMP HPLC instrument. The result showed that the retention time of polypeptide 239 was 22.3 min (retention volume: 89.0 mL), which is equal to the upper limit of TSK GSW3000. This indicated that the molecular weight of polypeptide 239 was more than 500 kD. The retention time of NE2 was 35.6 min (retention volume: 148.3 mL), which indicated that polypeptide 239 forms particles in solutions (FIG. 12A).

Observation of VLPs Using Transmission Electron Microscopy (TEM)

Figure 12B:
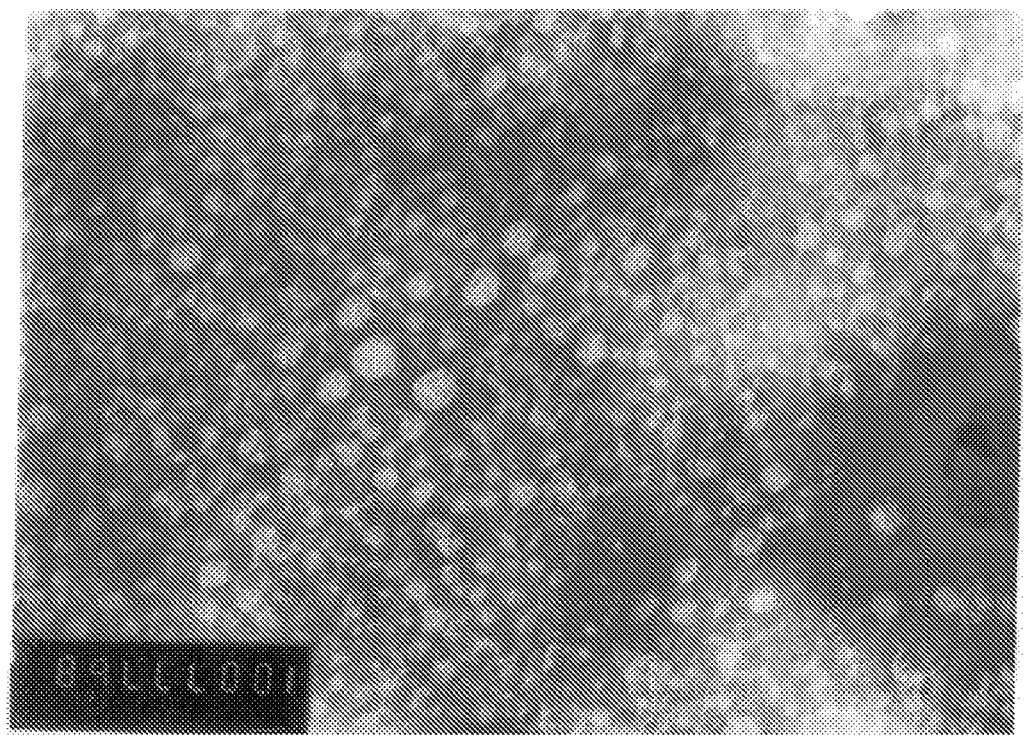

The renaturalized polypeptide 239 was adsorbed to carbon-coated grids, stained with 2% phosphotungstic acid (pH7.0), and examined by JEM-100CX II electron microscopy at about ×100,000 magnification. The photo of FIG. 12B showed many visible virus-like particles.

Observation of VLPs Using Atomic Force Microscopy (AFM)

Figure 13:
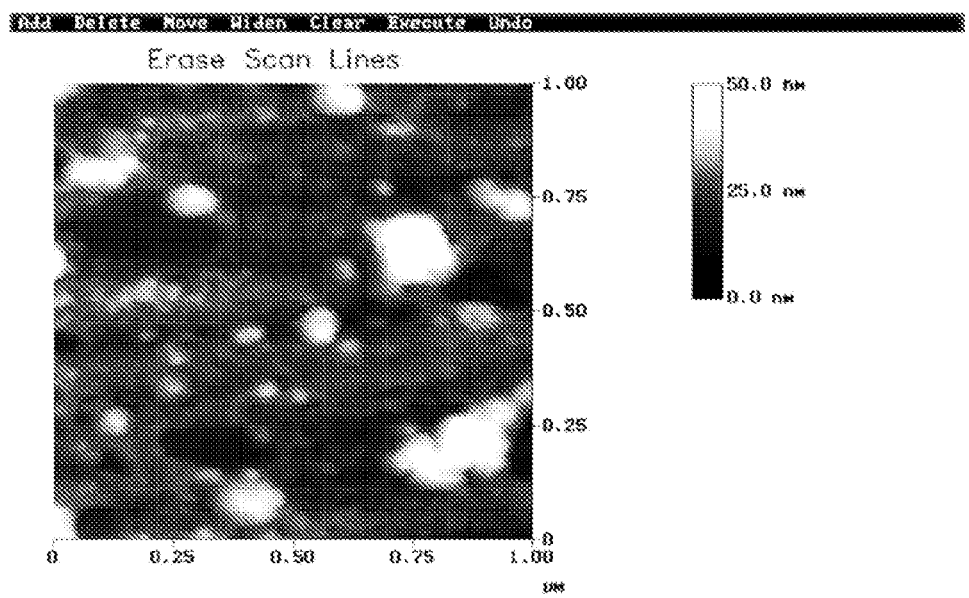
FIG. 13 shows the atomic force microscopy of recombinant polypeptides 239.

The analysis was performed on Nano IIIA atomic force microscopy (DI Company, USA), with a probe having 1 nm resolving power. The renaturalized polypeptide 239 was diluted in PBS (pH7.45) at 1:10, coated on surface of polystyrene, and then analyzed by AFM with a scanning area of 1 $mm^2$. The photo of FIG. 13 showed many visible virus-like particles.

Analysis of VLPs Using Dynamic Light Scattering

Figure 14:
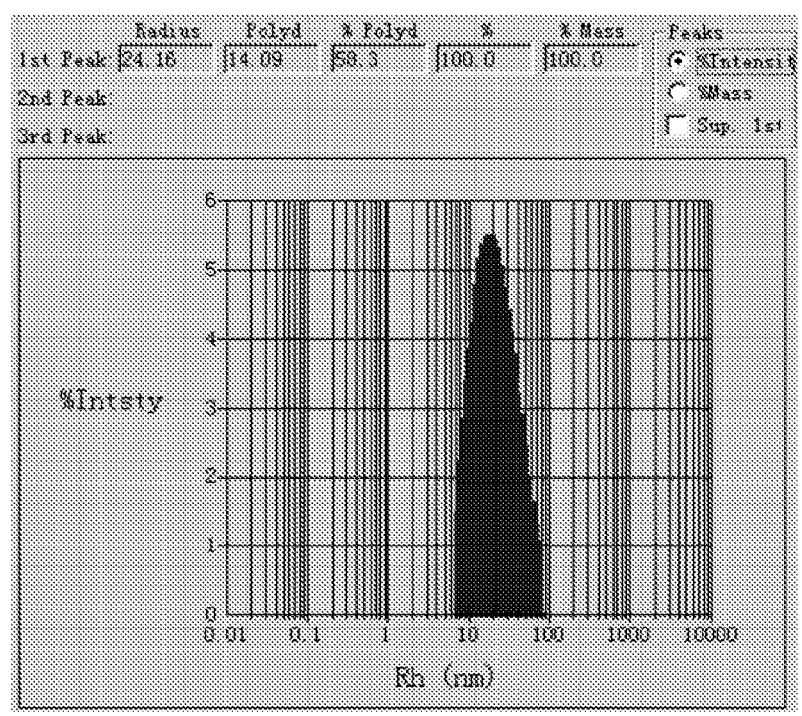
FIG. 14 shows dynamic light scattering result of recombinant polypeptides 239.

The analysis was performed on DynaPro MS/X Dynamic Light Scattering Instrument (containing a thermo controller), and the algorithm employed was Regulation algorithm. The polypeptide 239 was centrifuged (20,000 g) at 4° C. for 15 min, and then analyzed. The result showed that the hydrated molecular dynamic radius of polypeptide 239 was 24.16 nm (FIG. 14).

Example 27

The Antigenicity of Recombinant Polypeptide 239

The Antigenicity of Recombinant Polypeptide 239 Against Anti-HEV Monoclonal Antibody According to methods of Example 4, the purified polypeptide 239 was Western blotted with monoclonal antibodies. The results were similar to that of polypeptide NE2, i.e., monoclonal antibodies 1F6, 2C9, 7E8, 8C11, 8H3 and 13D8 were more strongly interacted with multimers of 239 than with monomers of NE2; on the contrary, monoclonal antibodies 15B2 and 16D7 interacted equally with multimers of 239 and monomers of NE2. After boiled, NE2 all disassociated into monomers, and still had unchanged antigenicities against monoclonal antibodies 15B2 and 16D7, but had significantly reduced antigenicities against monoclonal antibodies 1F6, 2C9, 7E8, 8C11, 8H3 and 13D8. These results suggested that the epitopes of 239 recognized by monoclonal antibodies 15B2 and 16D7 are linear epitopes; while the epitopes recognized by monoclonal antibodies 1F6, 2C9, 7E8, 8C11, 8H3 and 13D8 are conformation-dependent epitopes. These conformation-dependent epitopes were well-exposed in dimmer forms, but not in monomers.

Figure 15:
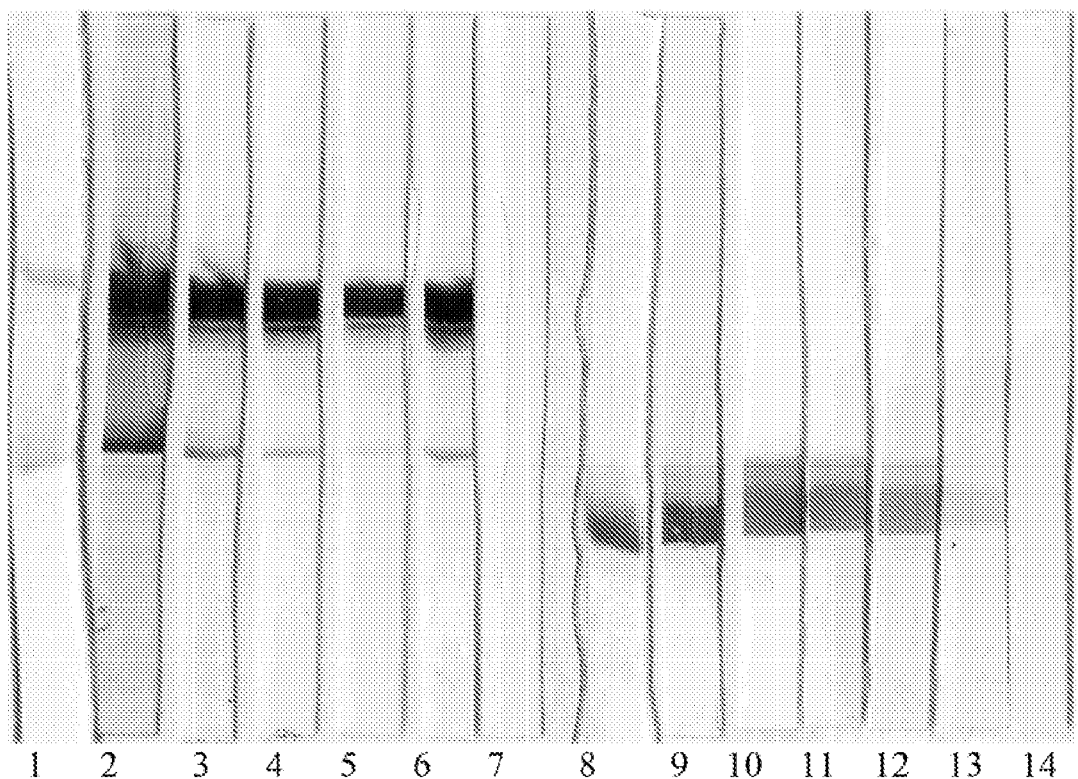
FIG. 15 shows Western blotting of recombinant polypeptides 239 by serum from patient of acute HEV infection. Lanes 1~7 are unboiled polypeptide 239, lane 8~14 are boiled polypeptide 239. Lane 1 and 8 are the result of SDS-PAGE, lanes 2/9, lanes 3/10, lanes 4/11, lanes 5/12, lanes 6/13 are five sera from patient in acute phase of HEV infections, lanes 7/14 are normal sera.

The Antigenicities of Polypeptide 239 Against Acute-phase Serum and Convalescent Serum of HEV Patients According to methods of Example 4, the purified polypeptide 239 was Western blotted with 5 samples of acute-phase sera of HEV patients, 5 samples of convalescent sera and 2 samples of normal human sera. The results (FIG. 15) showed that polypeptide 239 have obvious activity with acute-phase sera, furthermore, the dimer form's activitiy is stronger than that of monomer form; the dimer also showed high activity with 3 samples of convalescent sera from HEV patients; however, both forms of polypeptide 239 show no reaction to normal human sera.

Example 28

E. coli Expressed Particulate Polypeptide of HEV ORF2

A serial of N-terminal extension mutants of NE2 were cloned into pTO-T7 vector by primer-extention synthesis. Among them, the ratio of monomer to dimer, as well as the polimerization were compared on SDS-PAGE. In addition, according to the method of example 25, the particle formation was determined with size-exclusion HPLC in terms of their retention time.

The results (Table 15) indicated that the polypeptide 239 (AA368-603), resulted from N-terminal extension of NE2 to AA368, can self-assemble into particles, while the other N-terminal extension mutants, i.e. 217 (AA390-603), 227 (AA380-603), as well as NE2, all fail in self-assemble. So the region AA368-380 is related to the self-assemble of particles. Further extensions were performed to produce polypeptides 369, 370, 371, 372, 378, and 379. Among them, only 237C (AA370-603) was found to self-assemble into particles. To a further extension to AA345, the mutant still can self-assemble into particles.

TABLE 15 polymerizations of N-terminal extension mutants of NE2

| polypeptide | Location on HEV ORF2 | Monomer:Dimer | multimer | Particle |
|---|---|---|---|---|
| 227 | 380-603PPR | 60:40 | No | No |
| 228 | 379-603PPR | 60:40 | No | No |
| 229 | 378-603PPR | 40:60 | No | No |
| 235 | 372-603PPR | 60:40 | No | No |
| 236 | 371-603PPR | 90:10 | Yes | No |
| 237 | 370-603PPR | 90:10 | Yes | Yes |
| 238 | 369-603PPR | 90:10 | No | No |
| 239 | 368-603PPR | 50:50 | No | Yes |
| 240 | 367-603PPR | 90:10 | No | Yes (unstable) |
| 241 | 366-603PPR | 85:15 | No | Yes (unstable) |
| 242 | 365-603PPR | 80:20 | No | Yes (unstable) |
| 243 | 364-603PPR | 80:20 | No | Yes |
| 245 | 362-603PPR | 80:20 | No | Yes (unstable) |
| 251 | 356-603PPR | 30:70 | No | Yes |
| 262 | 345-603PPR | 60:40 | No | Yes |

The site-directed mutations on Leu of AA368, AA370, AA372, AA375, and AA395 all have adverse effect on the stability of particles (Table 16), which indicated that the structure near AA368 is important to the formation of stable particle.

TABLE 16

Particle assemble of HEV ORF2 polypeptide resulted from site-directed mutation on Leu located in AA368–395 region

| polypeptide | Location on HEV ORF2 | particle | Note |
|---|---|---|---|
| 370LI | 370-603PPR | unstable | 370Leu mutated to Ile |
| 370LA | 370-603PPR | Extremely unstable | 370Leu mutated to Ala |
| 370LE | 370-603PPR | no | 370Leu mutated to Glu |
| 370LQ | 370-603PPR | Extremely unstable | 370Leu mutated to Gln |
| 370LF | 370-603PPR | unstable | 370Leu mutated to Phe |
| 368LA | 368-603PPR | unstable | 368Leu mutated to Ala |
| 372LE | 368-603PPR | No | 372Leu mutated to Glu |
| 375LE | 368-603PPR | No | 375Leu mutated to Glu |
| 395LE | 368-603PPR | No | 395Leu mutated to Glu |

Another serial of C-terminal mutants of particulate polypeptides, i.e. 292, 208, 209, 242P, 202P, 172P and 170P (Table 17), were found to self-assemble into particles; and the polypeptides, of which C-terminal located upstream of AA603, can not form dimers. The results showed that formation of dimer may be not related to the assemble of particle, and the two mechanism might be modulated by different domains.

TABLE 17

Polymerization of C-terminal mutants of particulate polypeptides

| polypeptide | Location on HEV ORF2 | Length | Monomer:Dimer | multimer | Particle |
|---|---|---|---|---|---|
| 292 | 368-660 | 292 | 80:20 | No | Yes |
| 208 | 368-601 | 234 | 100:0 | No | Yes |
| 209 | 368-602 | 235 | 70:30 | No | Yes |
| 242P | 345-586 | 242 | 100:0 | No | Yes |
| 202P | 368-570 | 202 | 100:0 | No | Yes |
| 172P | 368-540 | 172 | 100:0 | No | Yes |
| 170P | 345-515 | 170 | 100:0 | No | Yes |

Example 29

The Antigenicities Against Monoclonal Antibodies of E. coli Expressed HEV ORF2 Polypeptides, which was Able to Self-assembling into Virus-like Particles

TABLE 18

| The antigenicities of particulate polypeptides against monoclonal antibodies (ELISA) | | | | | | | | |
|---|---|---|---|---|---|---|---|---|
| Polypeptide | Location on HEV ORF2 | 2C9 | 8C11 | 8H3 | 13D8 | 16D7 | 8C11 increases 8H3's reactivity | Sequence ID |
| 208 | AA368-601 | ± | ++++ | ± | +++ | ++++ | ×20 | SEQ ID No: 22 |
| 209 | AA368-602 | ± | + | ± | + | +++ | ×3 | |
| 239 | AA368-603PPR | +++ | ++++ | ++ | ++++ | ++++ | ×10 | SEQ ID No: 21 |
| 243 | AA364-603PPR | +++ | ++++ | + | ++++ | ++++ | ×10 | SEQ ID No: 23 |
| 251 | AA356-603PPR | +++ | ++++ | ++ | +++ | ++++ | ×10 | SEQ ID No: 24 |
| 262 | AA345-603PPR | +++ | ++++ | + | +++ | ++++ | ×10 | SEQ ID No: 25 |
| 292 | AA368-660PPR | ± | ++++ | ± | +++ | +++ | ×4 | SEQ ID No: 26 |

7. Selection of Peptides Mimicing the Epitope Identified by Monoclonal Antibody

Example 30

Selection of Peptides Mimicing the Epitope Identified by Monoclonal Antibody

The 7-peptide phage display library (New England BioLabs company) is used to screen 7-peptide which can be recognized by monoclonal antibody 8C11, 8H3, 13D8 or 16D7. The screening procedure was carried out as described in the phage display library user manual. Briefly, the mAb (100 μg/mL, in 20 mM PB pH7.5) was coated on 96-well microtiter plates (150 μL/well), and incubated at 37° C. over night. Pour off the coating solution. The plates were washed with PBST one time, dried, then incubate with the blocking buffer (0.1M $NaHCO_3$ pH8.6, 5 mg/mL BSA) for 2 hours at 37° C. Pour off the blocking solution. The plates were washed with PBST for 6 times, and dried. Separately, $2\times10^{11}$ phages were diluted into PBST (0.1% Tween-20) to 100 μL final volume. The diluted phage solution was then transferred into the coated 96-well microtiter plate (100 μL/well), and allowed to stand for 1 hour at room temperature. Pour off the phage solution, and firmly slap to remove residual solution. The wells were washed with PBST (0.1% Tween-20) for 10 times, and slapped to remove residual solution. The bound phages were eluted by incubating with 100 μL 0.2M Glycine-HCl (pH 2.2, containing 1 mg/mL BSA) for 10 min at room temperature. The solution was then piped into a microcentrifuge tube and neutralized with 1 mol/L Tris-HCl (pH 9.1). 1 μL solution was taken to titer the phage. The rest solution was added to 20 mL ER2738 culture at early stage of growing phase, and incubated at 37° C. with shaking for 4.5 h. The culture was transferred to a 50 mL centrifuge tube and spun 10 min at 10,000 g. 80% of the upper supernatant was collected and ⅙ volume of PEG/NaCl (20% PEG-8000, 2.5M NaCl) was added, standing at 4° C. over night. The mixture was then spun 15 min (10,000 g) at 4° C. The pellet was re-suspended in 1 mL PBS, and spun at 4° C. for 5 min. The supernatant was drawn and added ⅙ volume of PEG/NaCl solution, standing at 4° C. for 1 h. The mixture was then spun (10000 rpm) at 4° C. for 15 min. The supernatant was poured off, and the pellet was suspend in 200 μL PBS, and stored at 4° C. Repeat the above procedure for another cycle of screening.

The ER2738 host, which was cultured overnight, was diluted at 1:100 in LB culture medium. Dispense the diluted culture into tubes (1 mL/tube). 10 clones, which were blue plaques on LB/IPTG/Xgal culture plate after 3 rounds of screening, were selected and transferred to a tube containing the above diluted culture, and cultured for 4.5 hours at 37° C. Transfer the cultures to 1.5 mL microcentrifuge tubes. The single-stranded DNA were extracted according to the manual instruction for M13 mini Kit (from Shanghai Huashun Biotech Ltd), and then sequenced by Shanghai Boya Ltd, and the sequence result of 7-peptide inserted was listed in table 19.

TABLE 19

| Sequence of the 7-peptide binding with monoclonal antibody | | | |
|---|---|---|---|
| Monoclonal antibody | 7-peptide sequence | Clone numbers | SEQ ID NO |
| 8C11 | H A I Y P R H | 1 | SEQ ID NO: 76 |
| | H P T L L R I | 5 | SEQ ID No: 27 |

TABLE 19-continued Sequence of the 7-peptide binding with monoclonal antibody

| Monoclonal antibody | 7-peptide sequence | Clone numbers | SEQ ID NO |
|---|---|---|---|
|  | H W G M W S Y | 1 | SEQ ID NO: 77 |
|  | P V Q M P W L | 1 | SEQ ID NO: 78 |
|  | I T N D F K Q | 1 | SEQ ID NO: 79 |
|  | S L P T L T L | 1 | SEQ ID NO: 80 |
| 8H3 | S T L F M N F | 1 | SEQ ID NO: 81 |
|  | A L W G P T S | 2 | SEQ ID No: 28 |
|  | S A H V L S T | 1 | SEQ ID NO: 82 |
|  | S P P N V R T | 1 | SEQ ID NO: 83 |
|  | S I L P Y P Y | 3 | SEQ ID No: 29 |
|  | S P K M P I L | 1 | SEQ ID NO: 84 |
|  | F S Y L P S H | 1 | SEQ ID NO: 85 |
| 13D8 | V S W N S L V | 1 | SEQ ID NO: 86 |
|  | Y Q D S A K T | 2 | SEQ ID NO: 87 |
|  | T Y L P W P A | 1 | SEQ ID NO: 88 |
|  | N H W A S P R | 1 | SEQ ID NO: 89 |
|  | S S Y E W F I | 1 | SEQ ID NO: 90 |
|  | S A P S S K N | 1 | SEQ ID NO: 91 |
|  | I N Q K P T L | 1 | SEQ ID NO: 92 |
|  | S S M F F Y R | 1 | SEQ ID NO: 93 |
|  | S L V T G I L | 1 | SEQ ID NO: 94 |
| 16D7 | T N L R L D S | 1 | SEQ ID NO: 95 |
|  | Y Q D S A K T | 3 | SEQ ID NO: 96 |
|  | M L W G P S D | 1 | SEQ ID NO: 97 |
|  | Q P A T W N T | 1 | SEQ ID NO: 98 |
|  | G G W G P F A | 1 | SEQ ID NO: 99 |
|  | A L W G P T S | 1 | SEQ ID NO: 100 |

Example 31

Expression of the Peptide Mimicing the Epitope Recognized by 8H3 and 8C11

Separating and Cloning of HBc Gene

The specific primers BvCF and BvCR were designed (Table 20). With the plasmid pT-HBc constructed by our team (GenBank No. AF233235) as a template, PCR was used to amplify the full-length gene of HBc. The amplified fragment of about 550 bp was cloned into plasmid pMD 18-T to obtain a recombinant plasmid pT-C183. The sequencing result of the inserted fragment in plasmid pT-C183 showed that it was the full-length HBV core gene, which was 549 bp in length and encoded 183 amino acids.

TABLE 20

Primers for HBV gene cloning

| Primer | Nucleotide Sequence (5'→3') | |
|---|---|---|
| BvCF | GGA TCC CAT ATG GAC ATT GAC CCA | (SEQ ID NO: 101) |
| Bv149R | GAA TTC TTA AAC AAC AGT AGT TTC CGG | (SEQ ID NO: 102) |
| Bv80F | GT GGT ACT GGA TCC GGT GGT GGA GGT TCA GGA GGA GGT GGT TCC AGG GAA TTA GTA GTC | (SEQ ID NO: 103) |
| Bv78R | CC GGA TCC AGT ACC ACC ACC TCC AGA ACC ACC TCC ACC ATC TTC CAA ATT ACT TCC | (SEQ ID NO: 104) |
| 149MutRP | GAA TTC TTA AAC AAC AGT AGT TT | (SEQ ID NO: 105) |
| 8C11AFP | GGA TCC CAT CCT ACT CTT TTG CGT ATT GGT GGT GGA GGT TCA GG | (SEQ ID NO: 106) |
| 8H3AFP | GGA TCC TCT ATT CTG CCG TAT CCT TAT GGT GGT GGA GGT TCA GG | (SEQ ID NO: 107) |

Construction of Plasmid pC149-mut

Amino acid residues 79 and 80 at HBc MIR section were replaced with linker by site-directed mutation method to construct mutant plasmid pC149-mut for HBc expression.

With pT-C183 as template and Bv80F/Bv149R and Bv78R/BvCF as primer pairs (table 20), 3' terminal and 5' terminal sequences of HBc were amplified, and the production C80-149 and C1-78 were recovered. The two fragments were mixed in a new PCR reaction (Bv149R and BvCF as primers) to amplify mutant full-length HBc gene (named C149-mut). The product was cloned into T vector to obtain a recombinant plasmid pT-C149-mut. As described for pC143 and pC-149, the C149-mut fragment was subcloned into expression vector pTO-T7 to obtain the mutant plasmid pC149-mut for HBc expression. The BamHI restriction site with linkers at both sides was added into the sequence of pC149-mut. The amino acid sequence of C149-mut is C1–78+G4SG4T+GS+G4SG4+C81–149.

Construction of Mimic Peptides Expression Plasmids Based on Mutant HBc Plasmid

According to the sequencing result of 7-peptides, two long primers (8C11AFP and 8H3AFP of table 20) were designed to insert the 7-peptide gene between the linker and the BamH I site. The 3' primer was designed according to the sequence near EcoR I site on pC149-mut (149MutRP in table 20). DNA fragments comprising the 7-peptide DNA sequences were amplified by PCR, and cloned into pMD-18T vector to obtain plasmids pT-8C11 and pT-8H3. These two plasmids and pC149-mut vector were digested by BamH I and EcoR I. The vectors and the target fragments were recovered, and the vector and the fragment were linked together to obtain two recombinant expression plasmids pC149-mut-8C11 and pC149-mut-8H3. The amino acid sequences of expressed proteins were set forth as SEQ ID NO:30 (C149-mut-8C11) and SEQ ID NO:31 (C149-mut-8H3).

Expression of Plasmid Containing Mimic Peptide

E. coli strains ER2566, which were transformed with the recombinant plasmid pC149-mut-8C11 or pC149-mut-8H3, were cultured in 2 ml of LB liquid medium (containing Kan). Incubations were carried out in a shaker at 37° C. When the OD600 of the culture medium reached about 0.6, IPTG was added to a final concentration of 0.5 mmol/L, and the incubation was continued for 4 hours at 37° C. 1 mL of cell culture was transferred to a 1.5 mL tube, and spun at 12000 rpm for 30 sec, and dried upside down. The cells were re-suspended in 60 μL $H_2O$, then added with 30 μL of SDS-PAGE loading buffer (3×). The mixture was bathed in boiled water for 10 minutes, and spun at 12000 rpm for 10 min. 10 μL of the supernatant was used for SDS-PAGE analysis.

Testing the Immunological Activity of Mimic Peptide

3 μl of lysate supernantant of the above expressed polypeptides was dotted on the nitrocellulose membrane. 0.5% blocking solution containing skim milk was added at 0.1 mL/cm$^2$ and shaken for 2 hours at room temperature. Then monoclonal antibody 8C11 or 8H3 diluted at 1:100 with 5% skim milk was added at 0.1 mL/cm$^2$. The reaction was shaken at room temperature for 1 hour. Then the membrane was washed 3 times with TNT (each for 10 mins). The AP-labeled Goat anti-mouse IgG (diluted in 1:10000 with 0.5% skim milk) was added at 0.1 mL/cm$^2$, and reacted at room temperature for 1 hour. After washed 3 times with TNT (each for 10 mins), NBT/BCIP was added to develop color. Finally, PBS was added to stop the reaction. The result showed that C149-mut-8C11 and C149-mut-8H3 obviously reacted with corresponding monoclonal antibody.

8. The Diagnosis Kit Based on the Polypeptide Containing the Epitope of this Present Invention Recognized by the MAb and the Prophylaxis Application of this Polypeptide Example 32

Method for Labeling Polypeptide NE2 with Horseradish Peroxidase (HRP)

The following procedure was based on 20 mg of NE2: dissolve 40 mg of HRP (Biozyme R/Z>3) in 2 ml of acetate buffer (0.2M, pH5.6); add 2 ml of 0.06M $NaIO_4$ solution; the resulting solution was kept for 20 minutes at room temperature; add 2 ml solution of 0.16M ethylene glycol-10% NaCl, allow it to stand for 20 minutes at room temperature; dialyze the solution against 0.001M pH4.0 acetate buffer overnight; add 0.8 ml of 2M pH9.6 carbonate buffer and 20 mg NE2 antigen, and let it react for 2 hours at 4° C. with stirring; add 0.4 ml of freshly prepared $NaBH_4$ solution (5 mg/ml); allow it to stand for 2 hours at 4° C. with stirring; add drop wise 9.2 ml of saturated $(NH_4)_2SO_4$ solution; stir it for 30 minutes at 4° C., then centrifuge at 3500 rpm for 20 minutes at 4° C.; discard the supernatant, and dissolve the pellet in 2 ml of 0.02M pH7.4 phosphate buffer, then dialyze the solution against 0.02M pH7.4 phosphate buffer for 24 hours; add 2 ml of glycerol, then mix and store it at –20° C.

Example 33

The Diagnostic Kit for Detecting Anti-HEV IgG Antibodies and its Preparation and Manipulation The preparation procedure of the diagnostic kit containing the recombinant polypeptide NE2 of this invention is as followings: prepare and purify 1 mg/ml of recombinant polypeptide NE2 as described in example 1; dilute it with 20 mM pH7.4 PBS buffer at 1:500 and coat the 96-well microtiter plate at 100 uL/well at 37° C. for 2 hours followed by incubated at 4° C. overnight; then wash the plate once with PBS-Tween washing buffer (8.0 g NaCl, 0.2 g $KH_2PO_4$, 2.9 g $Na_2HPO_4.12H_2O$, 0.2 g KCl and 0.5 ml Tween-20, add deionized water to 1 L, and adjust pH to 7.4), and dry with upside down; add 200 ul of blocking solution (2% sucrose in PBS, 0.2% Casein, 2% Gelatin) per well, and incubate for 2 hours at 37° C.; blot the well dry and seal it in vacuum, then store it at 4° C.

The assay procedure of this kit is as followings: add 100 ul of sample dilution (20 mM pH7.2 PBS) to each well, then add 10 ul of serum, and incubate for 30 minutes at 37° C.; wash the microplate five times (with 20 sec interval) with PBS-Tween washing solution on the TECAN washing machine; blot to dry and add HRP-labeled secondary antibody (goat anti-human IgG) at appropriate dilution, then incubate for 30 minutes at 37° C.; wash it five times (with 20 sec interval) again and blot to dry; add a drop of chromatogen A and chromatogen B (chromatogen A: 13.42 g of $Na_2HPO_4.12H_2O$, 4.2 g of citric acid and 0.3 g $H_2O_2$, adding deionized water to 700 ml; chromatogen B: 0.2 g of TMB, 20 ml of DMF, adding deionized water to 700 ml), and incubate for 10 minutes at 37° C.; terminate the reaction with a drop of stoppting solution (2M $H_2SO_4$), and measure the absorbance for each well at 450 nm (the reference wavelength 620 nm) on the TECAN reader (Sunrise Remote/Touch Screen). the Cut-Off value is considered as OD value for the negative control plus 0.16. If the OD value is greater than the cut-off value, the result is regarded as positive, while if the OD value is less than the Cut-Off value, the result is negative.

Example 34

The μ-chain Capture ELISA Kit (E2-IgM) for Detecting Anti-HEV IgM Antibodies and its Preparation and Manipulation The preparation procedure of said kit is as followings: dilute NE2-HRP to 1:1000 as described in example 32; add 100 ul of goat anti-human μ-chain (DAKO) (1:1000, in 0.05M CB) to each well; incubate for 2 hours at 37° C., then overnight at 4° C.; wash the microplate once with PBST washing buffer (pH7.4); block each well with 200 ul blocking buffer by incubating for 2 hours at 37° C.; blot the blocked well to dry and seal it in vacuum, then store it at 4° C.

The assay procedure of this kit is as followings: add 100 ul of sample dilution (20 mM pH7.2 PBS) to each well, and add 10 ul of serum to be tested, then incubate for 30 minutes at 37° C.; wash the microplate five times with PBST washing solution; blot to dry and add 100 ul of working NE2-HRP (1:1000, prepared as in example 32), then incubate for 30 minutes at 37° C.; wash it five times again with PBST and blot to dry; add chromatogen, and incubate for 10 minutes at 37° C.; stop the reaction with a drop of stop solution, and read $OD_{450/620\ nm}$ value. The Cut-Off value is considered as the OD value for negative control plus 0.26. If the OD value is less than the Cut-Off value, the specimen is considered non-reactive, otherwise, reactive.

Example 35

The Sandwich ELISA Kit Intended for the Detection of HEV Antigen and its Preparation and Manipulation The preparation procedure of said kit is as followings: dilute the purified MAb 8C11 of this present invention to 50 ng/ml with 20 mM PBS (pH7.2), and add 100 ul of the dilution to each well; incubate overnight at 37° C.; then wash the microplate once with PBST; block each well with 200 ul 20% fetal bovine sera (FBS) by incubating for 2 hours at 37° C.

The assay procedure of this kit is as followings: add 50 ul of serum or 20% suspension of stool specimens prepared with FBS, then add 50 ul 8C11-HRP diluted with 20% FBS; gently mix it and incubate for 60 minutes at 37° C.; wash the microplate five times with PBST and blot to dry; add chromatogen A and chromatogen B each 50 ul, and incubate for 15 minutes at 37° C.; terminate the reaction with 50 ul of stopping solution, and measure the $OD_{450\ nm/620\ nm}$ for each well (PBST, chromatogen A and chromatogen B are purchased from Beijing Wantai biological pharmacy enterprise Co., Ltd). The Cut-Off value is considered as the OD value for the negative control plus 0.12. If the OD value is less than the Cut-Off value, the specimen is considered non-reactive, otherwise, reactive.

Example 36

The Example for Diagnosing the Sera with the E2-IgG ELISA Kit and the E2-IgM ELISA Kit of this Present Invention Detecting the E2-IgM and E2-IgG in Five Hepatitis E Patients' Sera and Forty Negative Sera Five hepatitis E patients' sera and forty negative sera were tested for the E2-IgM and E2-IgG. All of the OD values of five HE patients' sera were above 1.0 and all of negative OD values were below 0.1.

Dynamic Change of Different Anti-HEV Antibodies in the Rhesus Monkey Serum Following Infection with HEV As described in Table 20, 86 rhesus monkeys were challenged by a suspension of HEV-positive feces, and feces virus excretion was detected in 98.4% of infected rhesus monkeys. Response rate for GL-IgG (the IgG antibodies can be detected by the GENELABS DIAGNOSTICS HEV IgG ELISA) was 70.9%. GL-IgG seroconversion occurred between 3 weeks and 14 weeks after infection (the median was 5 weeks), and was 0.5~5 weeks (the mean was about 3 weeks) later than onset of hepatitis in over half animals. GL-IgG persisted from 1 week to over 69 weeks in different monkeys (less than 17 weeks in 75% monkeys). GL-IgG was not detected through the experiment in 25 monkeys, of which 11 monkeys had obviously abnormal ALT and the symptoms of acute hepatitis. E2-IgM seroconversion occurred in 85 monkeys (response rate was 98.8%) between 1 week and 8 weeks after infection (the median was 4 weeks), and occurred in 75% monkeys within 5 weeks after challenge. The persisting time was generally about 8 weeks. E2-IgM changed to negative between 3 weeks and 4 weeks after serum ALT level become normal. One monkey was negative always for E2-IgM, and the feces virus excretion was not detected, except that ALT was detected abnormal at week fourth. But its E2-IgG turned positive at 3rd week after infection and persisted over 20 weeks, while GL-IgG was not detected throughout the experiment. Response rate for E2-IgG was 100%. E2-IgG seroconversion occurred within 4.5 weeks after infection and its seroreversion didn't occur in any monkey within 84 weeks.

TABLE 20

Rates, mean time of onset and mean time of persistence of monkeys' responses to HEV infection.

| | Response rate | Onset (week) | | | persistence (week) | | |
|---|---|---|---|---|---|---|---|
| | | The earliest | The last | 75% onset | The longest | The shortest | The median |
| Virus excretion | 63/64 | 0.5 | 5.5 | 1 | 16.5 | 3 | 5 |
| viraemia | 12/12 | 1 | 4 | 1.5 | 11.5 | 1 | 4 |
| ALT | 54/79 | 1 | 8 | 4 | 9 | 1 | 2 |
| E2-IgM | 85/86 | 1 | 8 | 4.5 | >18 | 1 | 6 |
| E2-IgG | 86/86 | 1 | 8 | 4.5 | >81 | >20 | 17 |
| GL-IgG | 61/86 | 3 | 14 | 8 | >69 | 1 | 11 |

Figure 16:
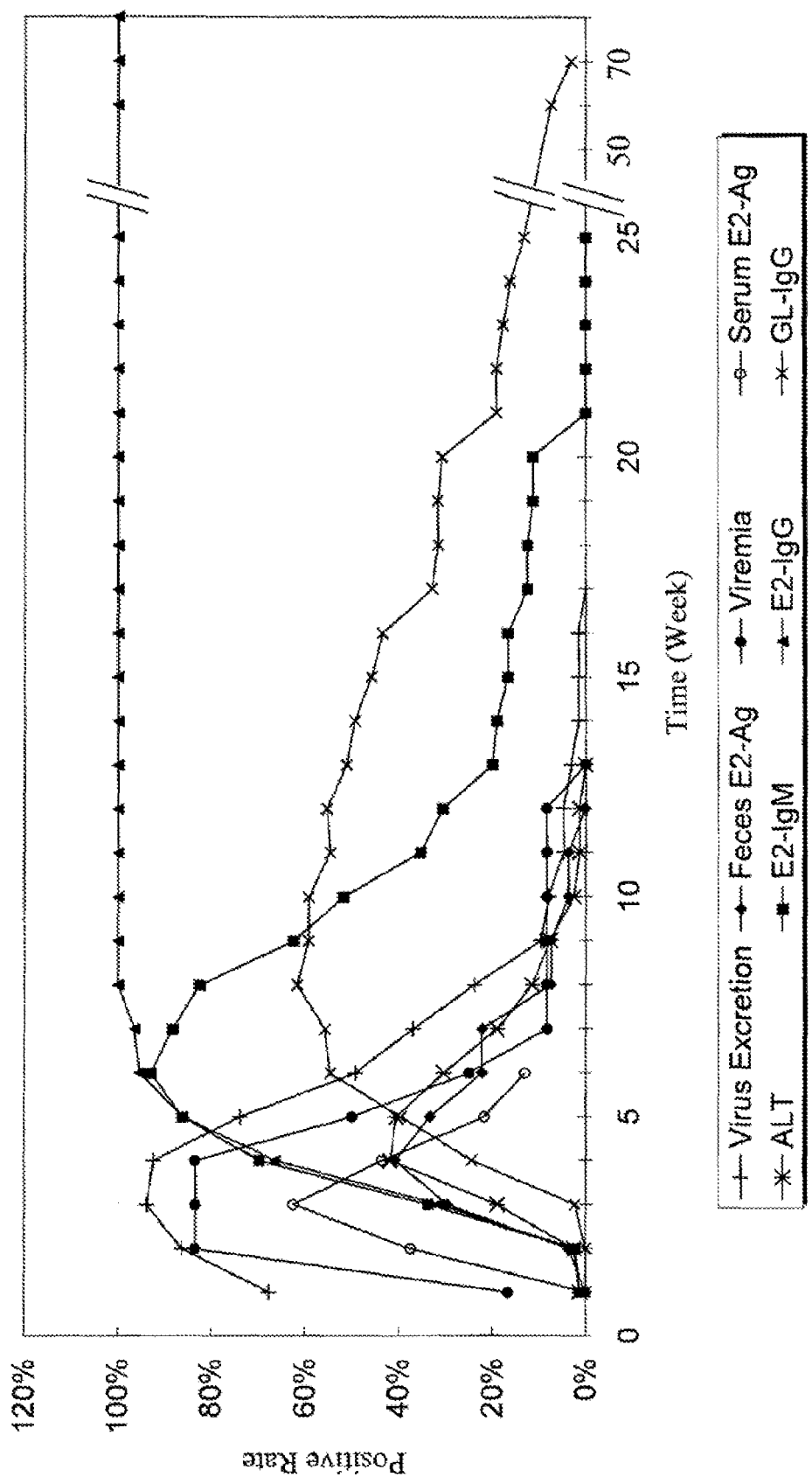
FIG. 16 the dynamic course of various parameters of monkey HEV infection.

Typically as in FIG. 16, virus excretion began on week 0.5 after infection, followed by viraemia. After E2-IgM and E2-IgG were first detected almost at the same time at week 3, serum ALT level rose, followed by seroconversion of GL-IgG. Then viraemia vanished rapidly, and serum ALT level returned normal in succession, and virus excretion was negative. About 3~4 weeks later, E2-IgM turned negative. Whereas level of GL-IgG declined slowly after having reached its respective peak value, E2-IgG was sustained at high level for the duration of the experiment, that is, after 70 weeks, the response rate remains 100%.

Figure 17:
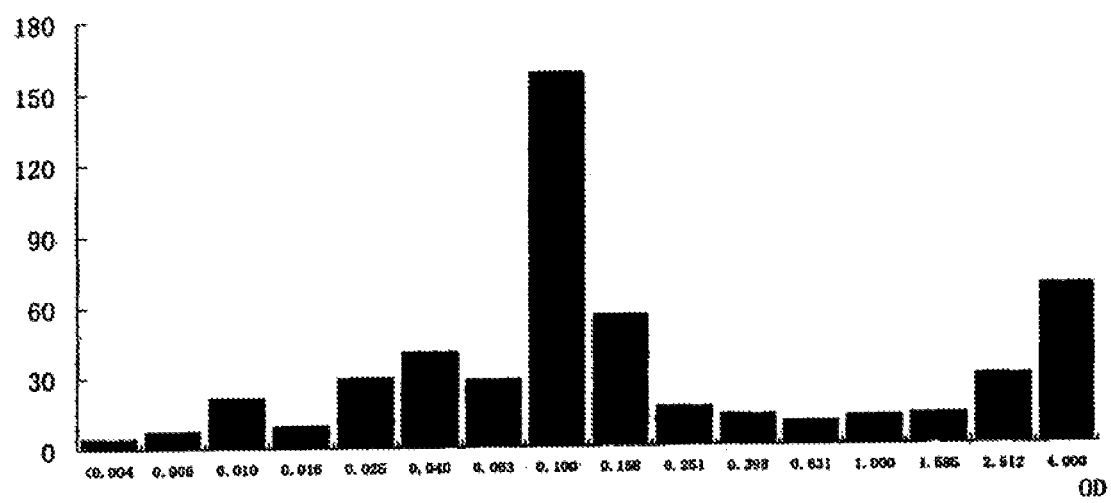
FIG. 17 shows the OD frequency distribution of anti-HEV-IgM capture reagents with NE2 as antigen for sera of 510 cases of clinic acute hepatitis infection.
Figure 18:
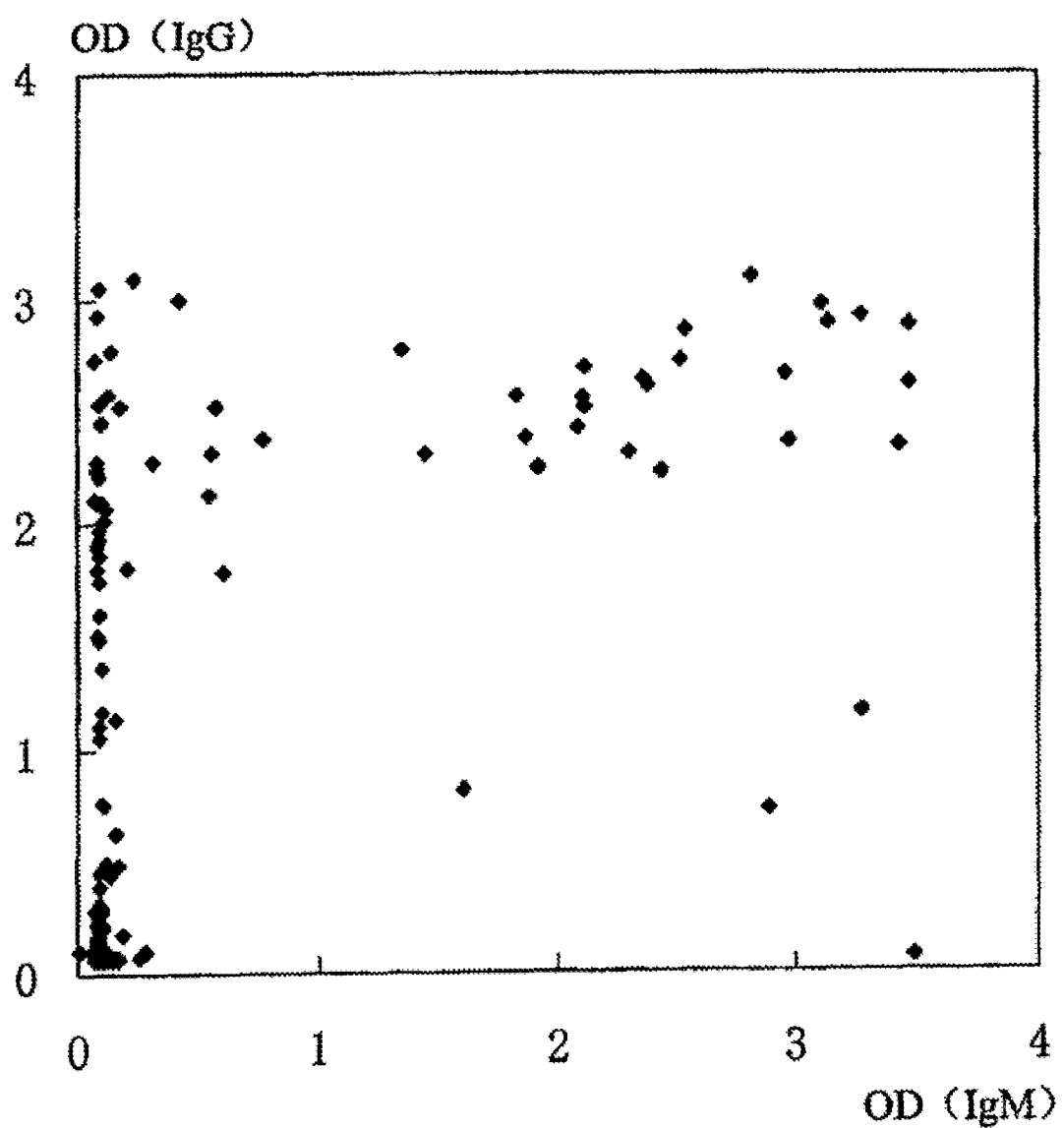
FIG. 18 shows the relationship between E2-IgM and E2-IgG OD values in sera of 200 cases of clinic acute hepatitis infection.

The Detection of IgM Antibodies to HEV in the Clinical Specimens of Acute Hepatitis Patients with the E2-IgM ELISA kit of this Present Invention Tested with E2-IgM ELISA kit, most of 928 normal serum specimens had the OD values below 0.15 with mean OD of 0.012. except that only two specimens had OD values higher than 0.2 (one is 0.203, the other is 0.333). The OD values of 510 serum specimens from clinical acute hepatitis patients varied from 0.001 to 4, respectively corresponding to the upper limit and lower limit of the microplate reader. For the OD values distributed nearly in exponential curve, their logarithmic distribution was analyzed after multiplying 1000 (FIG. 17). There were two peaks at two sides of the OD values of 0.398~0.631. The left peak had a approximate normal school with the logarithmic mean of 0.077, probably representing IgM-negative hepatitis patients; the right peak (OD>0.398) contained 131 specimens, 109 of which had the OD values higher than 1.0, probably representing IgM-positive HEV patients. If the cutoff for E2-IgM was set as 0.4, of 200 clinical hepatitis serum specimens, positive specimens of E2-IgM had higher OD values of E2-IgG, whereas most negative specimens had E2-IgG negative and the OD values of E2-IgG in the other specimens varied from low to high (FIG. 18).

Figure 19:
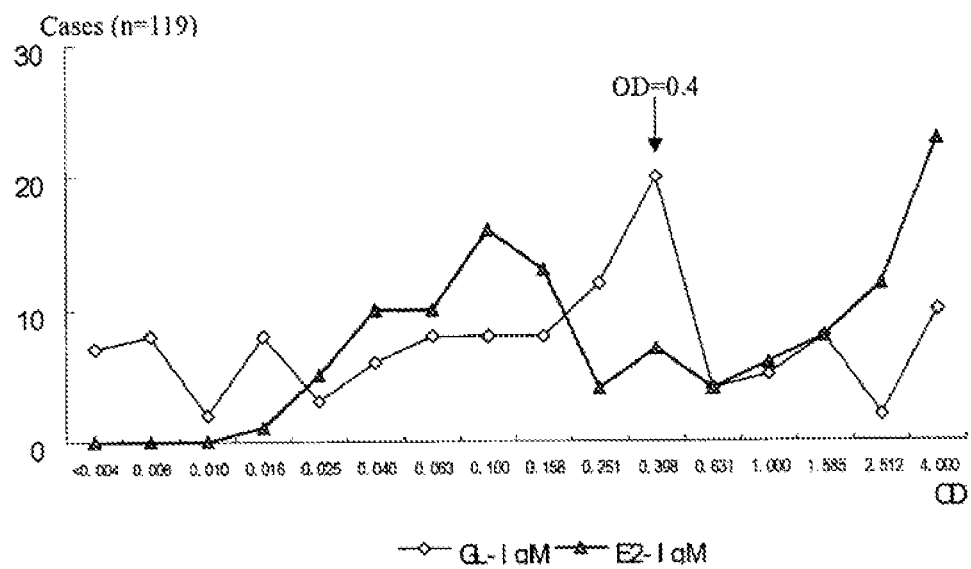
FIG. 19 shows the OD value frequency distribution of E2-IgM and GL-IgM for sera of 119 cases of non-HAV, non-HCV acute hepatitis infection.

To compare the distribution of OD values, E2-IgM kit and GL-IgM kit (GENELABS DIAGNOSTCS HEV IgM ELISA) were used to test 119 serum specimens of non-A~C hepatitis patients. The distribution of OD values for E2-IgM formed two clear peaks at two sides of the OD value of 0.4 as described above, whereas the distribution of the OD values for GL-IgM was irregular (FIG. 19). If the cut-off value was set as 0.4, the response rate for E2-IgM was 47.9% (57/119), whereas the response rate for GL-IgM was 24.4% (29/119).

In 29 GL-IgM positive specimens, E2-IgM was all reactive. However, none of the E2-IgM OD values of 30 serum specimens, which showes positive HAV-IgM, positive HBc-IgM or positive HCV-IgG, exceeded 0.2.

Figure 20:
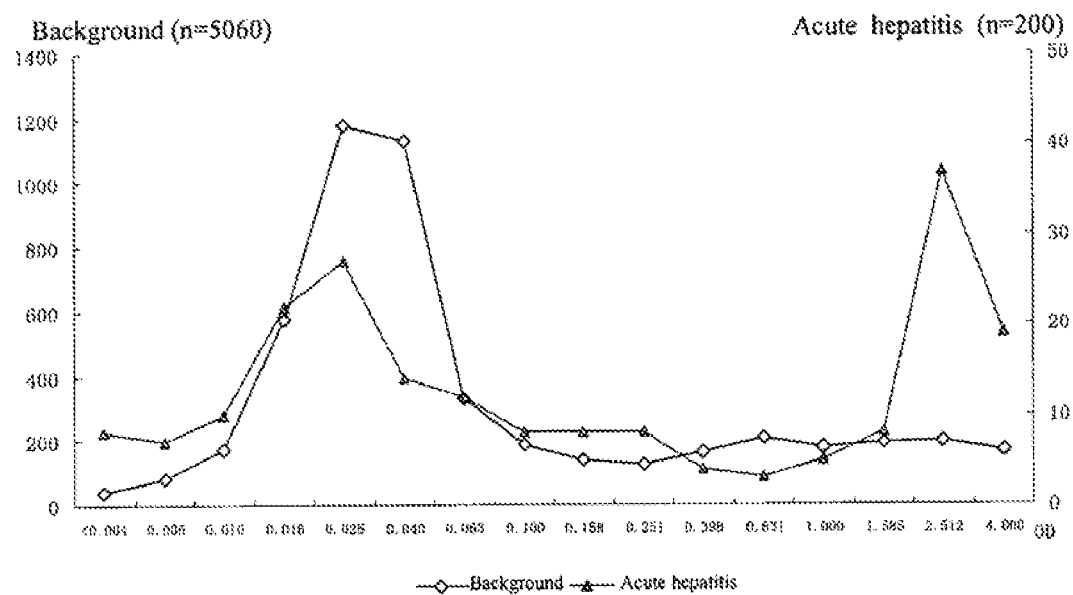
FIG. 20 shows the OD value frequency distribution for normal and acute hepatitis sera detected by the indirect ELISA kits with anti-HEV IgG.

The Detection of IgG Antibodies to HEV in the Clinical Specimens of Acute Hepatitis Patients and Normal Serum Specimens with the E2-IgG ELISA Kit of this Present Invention As described in Example 33, 5060 normal serum specimens and 200 clinical serum specimens from acute hepatitis patients were tested with the E2-IgG ELISA kit, and the OD values were analyzed with logarithmic frequency distribution (FIG. 20). As normal serum specimens were described, there was a peak similar to normal school around the OD value of 0.025. But when OD value came to above 0.2, the line extended slopely to the OD value of 4.0. With logarithmic frequency distribution analysis, of the specimens which OD values were less than 0.251, the mean of log(OD) was 1.333 (OD was 0.022) and the SD was 0.362. The cut-off OD with 95% specificity was 0.111 (x=2.042), meanwhile, the cut-off OD with 99% specificity was 0.185 (x=2.266). The OD values less than cut-off OD was distributed as an approximate normal school, and the most specimens represented by then might be negative for E2-IgG; the specimens, which OD values were higher than cut-off OD, might be positive for E2-IgG with different titers. With this cut-off OD, the response rate of the specimens was 22.2%.

Figure 21:
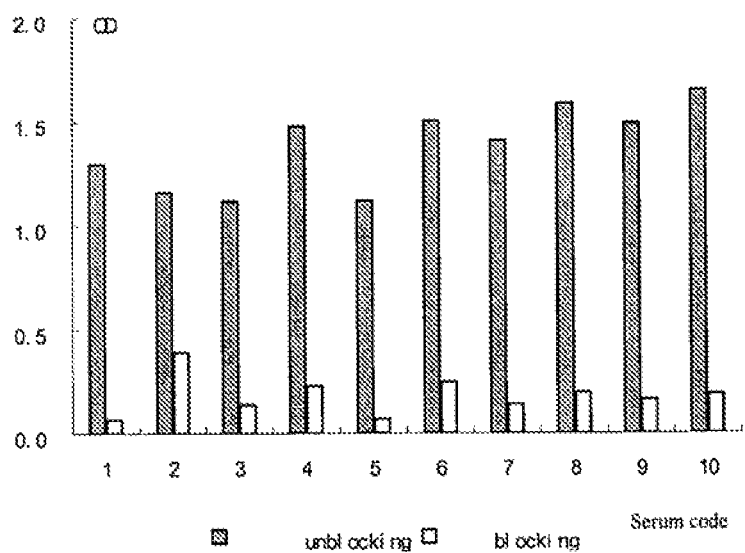
FIG. 21 shows the blocking E2-IgM positive serum by anti-HEV monoclonal antibody 8C11 and 8H3.

As 200 clinical serum specimens of acute hepatitis patients were described, there were two distinct peaks at either side of the cut-off OD. The left peak was similar to that of normal serum specimens, and the right peak was formed between OD value of 1.6~4.0 (peak at OD 2.5). It suggested that there were two groups in the acute hepatitis patients. One was similar to normal people (whose OD value was less than 0.2) and the other had higher OD value of E2-IgG, most of which were positive of E2-IgM (FIG. 21). The latter probably represented acute HEV patients.

Example 37

The Therapeutic Agent Comprising Anti-HEV MAb of the Present Invention, its Preparation and Blocking of E2-IgM Positive Serum or/and E2-IgG Positive Serum In the pre-coated NE2 microplate described as above, adding 100 ul of mixture of MAb 8C 11 and MAb 8H3 (each was diluted at the rate of 1:1000) to one well and adding 100 ul of diluent to another well at same time as control; incubating at 37° C. for 2 hours, and then up-side-down to dry the well; adding 100 ul of doubly serially diluted serum, and incubating at 37° C. for 30 minutes; washing the plate five times with PEST, then add pre-diluted 100 ul of anti-human IgM-HRP working dilution or anti-human IgG-HRP working dilution (provided by Beijing Wantai Biotech company) followed by incubating for 30 minutes at 37° C.; washing it five times again and dry up-side-down; adding chromatogen and incubating for 10 minutes at 37° C.; and then stopping reaction with 50 ul of 2M $H_2SO_4$, and determining the absorbance $OD_{450/620}$ nm for each well. Selecting the dilution rate at which the control OD value was 1.0~2.0 to calculate the blocking rate by the formula:

blocking rate=(control OD−blocked OD)/control OD*100%, and the MAbs can block the serum successfully if the blocking rate was above 50%.

In the pre-coated NE2 microplate described as above, adding 100 μl of mixture of MAb 8C11 and MAb 8H3 (diluted at the ratio of 1:1000) to one well, adding 100 μl of mixture of Fab segment of MAb 8C11 and Fab segment of MAb 8H3 (diluted at the ratio of 1:1000) to another well and adding 100 ul of diluent to the third well at the same time as control; incubating for 2 hours at 37° C., and dry up-side-down; adding 100 ul of serum of serial dilution at the rate of 1:2, and incubating for 30 minutes at 37° C.; washing the plate five times with PEST and dry up-side-down, then add 100 μl of anti-human IgM-HRP or anti-human IgG-HRP diluted to working concentration followed by incubating for 30 minutes at 37° C.; washing it five times and dry up-side-down; adding chromatogen and incubating for 10 minutes at 37° C.; stopping the reaction with 50 ul of 2M $H_2SO_4$, and determining the absorbance $O_{450/620\ nm}$ for each well.

To verify the specificity of E2-IgM ELISA, two MAbs that directly captures HEV, 8C11 and 8H3, were used to block E2-IgM in 10 E2-IgM positive serum specimens. The result manifested that the MAbs could block markedly the reaction between sera and E2 antigen with blocking rate in the range of 66.4%~94.8% (the mean block rate is 86.6% (86.6%±7.9%)) (see, FIG. 21). As for 10 E2-IgG positive serum specimens, the reactions between sera and E2 antigen have all been blocked with the blocking rates varied from 55% to 96%, the mean block rate of 75.7%.

Figure 22:
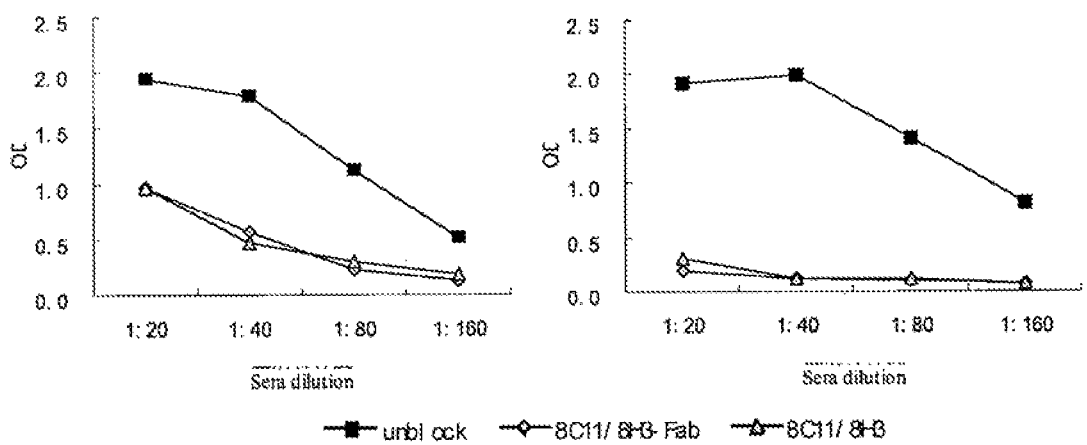
FIG. 22 shows the blocking of E2-IgG by anti-HEV monoclonal antibody 8C11, 8H3 or their Fab fragment.

To estimate the impact of steric hindrance effect of monoclonal antibody on the blocking test, the Fab segment of the two MAbs were used to block two serum specimens simultaneously. As illustrated in FIG. 22, the effect of blocking of Fab segment substantially consisted with its whole antibody, which indicated that the blocking effect of the MAbs against positive sera was epitope specificity.

Example 38

Double Antigen Sandwich ELISA (DS-ELISA)

The NE2 microplate was prepared as described above in example 33. The assay procedure was as followings: adding 50 ul of diluted NE2-HRP to per well after adding 50 ul of serum specimen; gently tapping the plate to homogenize the reagents and incubating for 30 minutes at 37° C.; washing it 6 times and dry up-side-down; then adding chromatogen (TMB substrate, supplied by Beijing Wantai biological pharmacy enterprise Co., Ltd). After incubating for 10 minutes at 37° C., stopping the reaction with 50 ul of 2M $H_2SO_4$; then measuring the absorbance for each well at 450 nm with the reference wavelength 620 nm. Calculating the Cut-Off value by adding 0.12 to the mean absorbance of negative control. If its absorbance value is less than the Cut-Off value, the specimen is considered non-reactive, otherwise, reactive.

Figure 23:
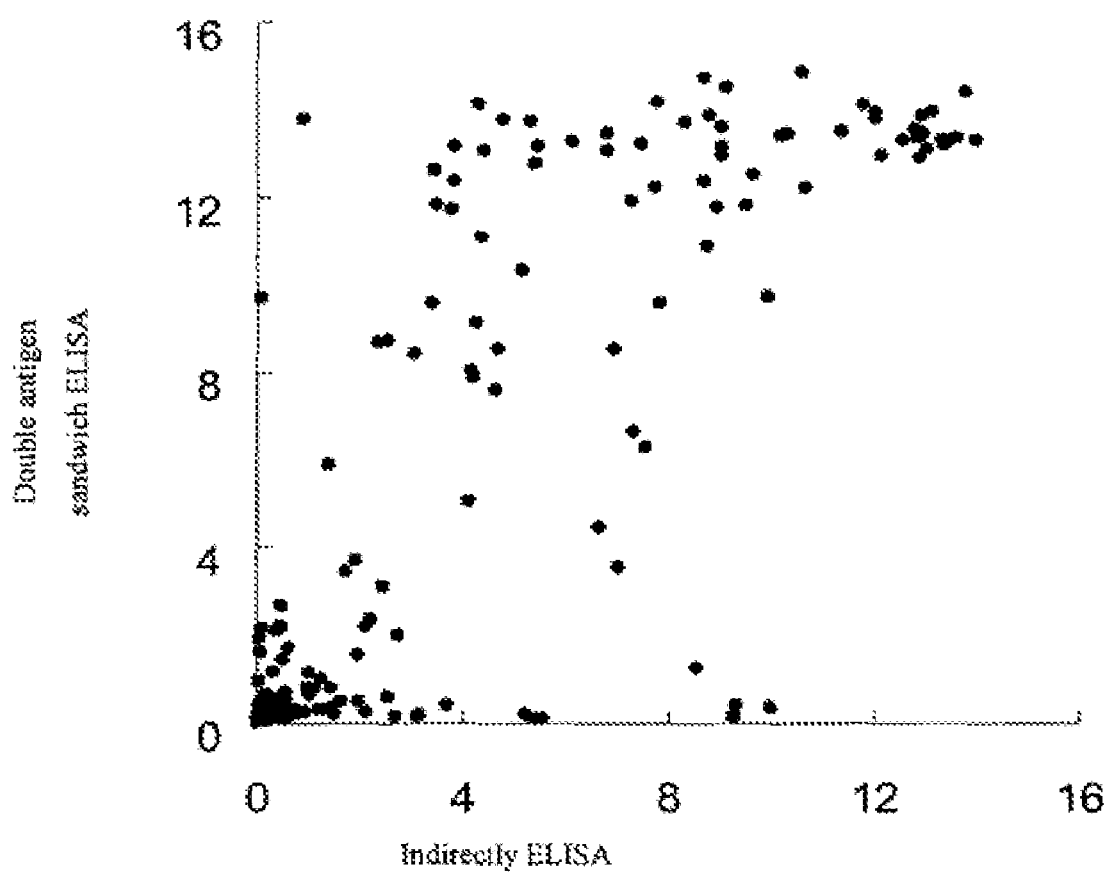
FIG. 23 shows the consistency of s/co results detected in two antibody sandwich and indirect ELISA for sera of 400 blood-donors.

The serum specimens of 400 volunteer blood donors were tested by DS-ELISA and E2-IgG ELISA and the result manifested that the two ELISA consisted with each other perfectly. As the ratio of sample/cut-off of positive specimens was mentioned, the DS-ELISA was higher than the E2-IgG ELISA (SEE, FIG. 23).

Anti-HEV antibodies were screened in the sera of cows, sheep, goats and pigs collected from XinJiang and the sera of hens from ShangHai by DS-ELISA. As described in table 21, anti-HEV antibodies could be detected from those species of animals without exception, and the positive rate in pigs was up to 79.9%.

TABLE 21

The positive rate of anti-HEV antibodies in different animals screened by DS-ELISA

| Animal | Detected number | Reactive number | Response rate(%) |
|---|---|---|---|
| Cows | 202 | 13 | 6.4 |
| Sheep | 24 | 3 | 12.5 |
| Goats | 30 | 2 | 6.7 |
| Pigs | 443 | 353 | 79.7 |
| Hens | 173 | 3 | 1.7 |

Example 39

Vaccine Comprising the Antigenic Determinants of Peptide 239, its Preparation and its Immunogenicity Vaccinated animal: 6 BAL B/c mice and 6 Kunming white mice, at 4-6 weeks old Preparation of vaccine: A desired amount of original aluminum adjuvant from the Lanzhou Biological Product Institute of China, was adjusted with 1N NaOH till to occurrence of precipitate. After mixing completely, 1×PBS was added to double the volume. Then centrifugation was performed at 10,000 rpm for 1 min, and the supernatant was discarded. The precipitate was resuspended in 1×PBS to double the volume, and centrifuged at 10,000 rpm for 1 min and the supernatant was discarded. Such process was repeated several times until the pH reached 7-7.4. Finally, the precipitate was resuspended with equal volume of 1×PBS, and the solution was sterilized and stored at 4° C., and used as 9×store solution. The purified polypeptide 239 were mixed with the preceding aluminum adjuvant to a final concentration as 5 µg/100 µl, at 4° C., overnight. The vaccine without adjuvant was prepared with only polypeptide 239 with 5 µg/100 µl concentration. The dose was designed as 5 µg/mouse.

Vaccinating program: The animals were grouped to adjuvant vaccine and non-adjuvant vaccine group. Each group had 3 BAL B/c mice (Coded B1~B3, B4~B6) and Kunming white mice (Coded K1~K3, K4~K6), intramuscularly vaccinated according to the immunizing schedule of 0, 10 days. The presence of anti-HEV antibodies in weekly collected sera was detected with an ELISA kit by HEV-NE2 polypeptide coated plate.

Results (see Table 22): The non-adjuvant and aluminum adjuvant 239 vaccine all had excellent immunogenicity. Especially, only one vaccination of non-adjuvant vaccine will make one of three mice to elicit anti-HEV antibodies. After two vaccinations, the anti-HEV antibody tilter of several mice can reach above $1:10^5$.

TABLE 22

Immunogenicity of mice inoculated with polypeptide 239 vaccine

| Groups | Seroconvertion | Peak of Seroconvertion | Tilters at peak |
|---|---|---|---|
| Non-adjuvant | | | |
| B1 | 10 day | 5 week | $1:10^5$ |
| B2 | 2 week | 4 week | $1:10^4$ |
| B3 | 2 week | 6 week | $1:10^5$ |
| K1 | 2 week | 4 week | $1:10^4$ |
| K2 | 2 week | 4 week | $1:10^3$ |
| K3 | 3 week | 6 week | $1:10^3$ |
| aluminum adjuvant | | | |
| B4 | 2 week | 5 week | $1:10^5$ |
| B5 | 2 week | 4 week | $1:10^4$ |
| B6 | 2 week | 4 week | $1:10^4$ |
| K4 | 3 week | 4 week | $1:10^3$ |
| K5 | 10 day | 4 week | $1:10^5$ |
| K6 | 2 week | 4 week | $1:10^3$ |

Example 40

The Immuno-protectivity of the Polypeptide 239

Preparation of the Vaccine Containing the Polypeptide 239 with Aluminum Adjuvant A desired amount of the original aluminum adjuvant from the Lanzhou Biological Product Institute of China, was adjusted with 1N NaOH till occurrence of precipitate. After mixing completely, 1×PBS was added to reach the double volume. Then centrifuge was performed at 10,000 rpm for 1 min, and the supernatant was discarded. The precipitate was resuspended with 1×PBS to the double volume, and centrifuged at 10,000 rpm for 1 min and the supernatant was discarded. Such process was repeated several times until the pH reached 7-7.4. Finally, the precipitate was resuspended with equal volume of 1×PBS, and the solution was sterilized and stored at 4° C., and used as 9×store solution. The polypeptide 239 produced as above-mentioned and purified by HPLC (the concentration of the protein is 1.0 mg/ml) was diluted with PBS, and the ⅑ volume of aluminum adjuvant was added to reach a desired final concentration of the polypeptide 239 (10 ug/ml), and mixed overnight at 4° C. The mixture was divided into 1.2 ml per ampoule, and the ampoules were stored darkly at 4° C. Before usage the ampoule must be mixed.

Immunizing Scheme

Six healthy rhesus monkeys with normal ALT and negative HEV were selected and divided into two groups, 3 monkeys per group. The monkeys of immunization group were vaccinated three times by intradeltoidal injection with 10 ug of the aluminum adjuvant containing polypeptide 239 vaccine on day 0, day 10 and day 58, respectively. The control was not immunized.

Challenging with HEV

Those monkeys in two groups were challenged on 86th day after the first immunization (on $28^{th}$ day after the last immunization) with 0.25 ml of 20% fecal suspension of HEV XM strain per monkey ($2*10^5$ PCR titers per monkey).

Collecting of Specimens

Serum samples were taken before and once weekly for at least 10 weeks after infection and then once biweekly thereafter. Serum ALT was determined with fresh serum on the day of sample collection.

Stool specimens were collected every other day for 10 days and then twice weekly for up to 86 days. If the virus RNA was undetectable continuously after onset, the virus excretion was considered to reverse.

Detection of HEV Markers

Anti-HEV IgG antibodies: detecting the anti-HEV IgG of monkeys' sera with two methods Method 1 was E2-IgG ELISA, which assay procedure was described in Example 31. In method 2, the GL-IgG was detected with the GENELABS DIAGNOSTICS HEV IgG ELISA kit. Recombined polypeptide of HEV ORF2 and ORF3 was used in this kit, which mimicked epitopes of C domain of HEV ORF2 (AA604~AA660) and HEV ORF3 that does not overlap with the main epitope of NE2.

Virus excretion: detecting the HEV RNA in the stool by the method as described in Example 11.

Anti-HEV IgM antibodies: detecting the anti-HEV IgM of monkeys' sera by the method as described in example 32.

Results:

As described in table 22, of all three control monkeys, the virus excretion, E2-IgM, E2-IgG and GL-IgG were detected in a week after challenge, which manifested that HEV infected those monkeys and replicated successfully. In two of three immunized monkeys, virus excretion, E2-IgM and GL-IgG were undetectable always, but in the other monkey, virus excretion began on week 3 after challenge and E2-IgM and GL-IgG conversed on week 7 after challenge. Immunized monkeys could avoid infection from HEV or lighten the symptom sharply, which manifested that polypeptide 239 had effective immuno-protectivity.

Example 41

The Double Antigens Sandwich ELISA (DS-ELISA) Kit for Detecting Total Anti-HEV Antibodies in Biological Specimens, its Preparation and its Assay Procedure The DS-ELISA kit consists of the pre-coated microwells with recombined polypeptide NE2, the working NE2-HRP solution diluted with the enzyme diluent (20 mM pH7.2 PB, 5% casein and 10% NBS) and some non-biological active materials (such as 20×PBST, chromatogen A, chromatogen B and stop solution etc.) purchased from Beijing Wantai biological pharmacy enterprise Co., Ltd.

The assay procedure of this kit is as follow: adding 50 ul of diluted NE2-HRP to each well after adding 50 ul of serum specimen; gently tapping the plate to homogenize the reagents and incubating for 60 minutes at 37° C.; washing it 6 times and dry up-side-down; then adding each 50 ul of chromatogen A and chromatogen B; after incubating for 15 minutes at 37° C., stopping the reaction with 50 ul of 2M $H_2SO_4$; then determining the absorbance for each well at 450 nm with the reference wavelength 620 nm.

Anti-HEV antibodies were screened in the sera of cows, sheep, goats and pigs collected from XinJiang and the sera of hens from ShangHai by DS-ELISA. As described in table 23, anti-HEV antibodies could be detected form those species of animals without exception, and the positive rate in pigs was up to 79.9%.

TABLE 23

The positive rate of anti-HEV antibodies in different animals screened by DS-ELISA

| Animal | Detected number | Reactive number | Response rate(%) |
| --- | --- | --- | --- |
| Cows | 202 | 13 | 6.4 |
| Sheep | 24 | 3 | 12.5 |
| Goats | 30 | 2 | 6.7 |
| Pigs | 443 | 353 | 79.7 |
| Hens | 173 | 3 | 1.7 |

TABLE 22 the immuno-protectivity of recombined HEV VLPs formed by polypeptide 239

| Groups | The titer of E2-IgG before challenge | The persistence of virus excretion (weeks) | The onset of E2-IgM (weeks) | The persistence of GL-IgG (weeks) | The onset of E2-IgG (weeks) |
| --- | --- | --- | --- | --- | --- |
| Immunization | | | | | |
| HY10 | 1:5120 | Non | Undetected | Non | — |
| HY11 | 1:5120 | 3-7 | 7 | 7-10 | — |
| HY12 | 1:10240 | Non | Undetected | Non | — |
| Control | | | | | |
| HY13 | <1:10 | 1-5.5 | 3 | 3-7 | 4 |
| HY14 | <1:10 | 0.5-6.5 | 3 | 4-16 | 3 |
| HY15 | <1:10 | 1-5.5 | 3 | 5-10 | 3 |

What is claimed is:

1. An antibody or fragment thereof comprising a heavy chain variable region and light chain variable region,
    wherein the sequences of the heavy chain variable region and the light chain variable region are
    (a) the amino acid sequences of SEQ ID NOS: 12 and 10, respectively, of monoclonal antibody 8C11,
    (b) the amino acid sequences of SEQ ID NOS: 8 and 6, respectively, of monoclonal antibody 13D8, or
    (c) the amino acid sequences of SEQ ID NOS: 16 and 14, respectively, of monoclonal antibody 8H3,
    and wherein the antibody or the fragment thereof binds to the native conformation of a polypeptide sequence encoded by hepatitis E virus (HEV) ORF2, but has decreased or no binding to the denatured polypeptide sequence encoded by hepatitis E virus (HEV) ORF2.

2. The antibody or fragment thereof of claim 1, wherein the polypeptide sequence encoded by hepatitis B virus (HEV) ORF2 is SEQ ID NO: 1.

3. The antibody of claim 1, wherein the antibody is monoclonal antibody 8C11, monoclonal antibody 13D8, or monoclonal antibody 8H3.

4. The fragment of claim 1, wherein the fragment is a Fab fragment.

5. The fragment of claim 1, wherein the fragment is a single chain antibody.

6. The antibody of claim 1, wherein the antibody is a humanized antibody.

7. A diagnostic kit for detecting a hepatitis E virus infection comprising a diagnostic effective amount of the antibody or fragment thereof of claim 1.

8. The diagnostic kit of claim 7, wherein the diagnostic effective amount of the antibody or fragment thereof is 100 ng-1000 ng.

9. A humanized antibody comprising complementary determining regions (CDRs) of a heavy chain variable region and a light chain variable region, wherein the sequences of CDRs of the heavy and light chain variable regions are the CDRs of
    (a) the amino acid sequences of SEQ ID NOS: 12 and 10, respectively, of monoclonal antibody 8C11,
    (b) the amino acid sequences of SEQ ID NOS: 8 and 6, respectively, of monoclonal antibody 13D8 or
    (c) the amino acid sequences of SEQ ID NOS: 16 and 14, respectively, of monoclonal antibody 8H3,
    and wherein the antibody binds to the native conformation of a polypeptide sequence encoded by hepatitis E virus (HEV) ORF2, but has decreased or no binding to the denatured polypeptide sequence encoded by hepatitis B virus (HEV) ORF2.

10. An antibody or fragment thereof comprising complementary determining regions (CDRs) of a heavy chain variable region and a light chain variable region, wherein the sequences of CDRs of the heavy and light chain variable regions are the CDRs of
    (a) the amino acid sequences of SEQ ID NOS: 12 and 10, respectively, of monoclonal antibody 8C11,
    (b) the amino acid sequences of SEQ ID NOS: 8 and 6, respectively, of monoclonal antibody 13D8 or
    (c) the amino acid sequences of SEQ ID NOS: 16 and 14, respectively, of monoclonal antibody 8H3,
    and wherein the antibody binds to the native conformation of a polypeptide sequence encoded by hepatitis E virus (HEV) ORF2, but has decreased or no binding to the denatured polypeptide sequence encoded by hepatitis B virus (HEV) ORF2.

* * * * *

SEQUENCE LISTING

<160> NUMBER OF SEQ ID NOS: 107

<210> SEQ ID NO 1
<211> LENGTH: 660
<212> TYPE: PRT
<213> ORGANISM: Hepatitis E virus

<400> SEQUENCE: 1

```
Met Arg Pro Arg Pro Ile Leu Leu Leu Leu Met Phe Leu Pro Met
1               5                   10                  15

Leu Pro Ala Pro Pro Gly Gln Pro Ser Gly Arg Arg Gly Arg
            20                  25                  30

Arg Ser Gly Gly Ser Gly Gly Gly Phe Trp Gly Asp Arg Val Asp Ser
            35                  40                  45

Gln Pro Phe Ala Ile Pro Tyr Ile His Pro Thr Asn Pro Phe Ala Pro
        50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Ala
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu Tyr Phe Thr Ser Thr Asn Gly Val Gly Glu Ile Gly Arg Gly Ile
```

```
                355                 360                 365
Ala Leu Thr Leu Phe Asn Leu Ala Asp Thr Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
                420                 425                 430

Leu Gly Glu Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
                500                 505                 510

Ser Leu Asp Trp Thr Lys Val Thr Leu Asp Gly Arg Pro Leu Ser Thr
            515                 520                 525

Ile Gln Gln Tyr Ser Lys Thr Phe Phe Val Leu Pro Leu Arg Gly Lys
530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
                580                 585                 590

Val Ser Ile Ser Ala Val Ala Val Leu Ala Pro His Ser Val Leu Ala
            595                 600                 605

Leu Leu Glu Asp Thr Met Asp Tyr Pro Ala Arg Ala His Thr Phe Asp
610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 2
<211> LENGTH: 1990
<212> TYPE: DNA
<213> ORGANISM: Hepatitis E virus

<400> SEQUENCE: 2
atgcgccctc ggcctatttt gctgttgctc ctcatgtttc tgcctatgct gcccgcgcca      60
ccgcccggtc agccgtctgg ccgccgtcgt gggcggcgca gcggcggttc cggcggtggt     120
ttctggggtg accgggttga ttctcagccc ttcgcaatcc cctatattca tccaaccaac     180
cccttcgccc ccgatgtcac cgctgcggcc ggggctggac tcgtgttcg ccaacccgcc     240 cgaccactcg gctccgcttg gcgtgaccag gccagcgcc cgccgttgc ctcacgtcgt     300 agacctacca cagctggggc cgcgccgcta accgcggtcg ctccggccca tgacacccg     360
```

```
ccagtgcctg atgttgactc ccgcggcgcc atcctgcgcc ggcagtataa cctatcaaca    420
tctccccta cttcttccgt ggccaccggt acaaacttgg ttctatacgc cgctcctctt     480
agcccacttc taccccctcca ggacggcacc aatactcata taatggccac agaagcttct   540
aattatgccc agtaccgggt tgctcgtgcc acaattcgct accgcccgct ggtccccaac    600
gctgttggtg gctacgccat ctccatctcg ttctggccac agaccaccac caccccgacg    660
tccgttgaca tgaattcaat aacctcgacg gatgttcgta ttttagtcca gcccggcata    720
gcctccgagc ttgttatccc aagtgagcgc ctacactacc gtaaccaagg ttggcgctct    780
gttgagacct ccggggtggc ggaggaggag gccacctctg tcttgttat gctctgcata     840
catggctcac ctgtaaattc ttatactaat acaccttata ccggtgccct cgggctgttg    900
gactttgccc tcgaacttga gttccgcaac ctcaccccg gtaataccaa cacgcgggtc     960
tcccgttact ccagcactgc ccgtcaccgc cttcgtcgcg gtgcagatgg gactgccgag   1020
cttaccacca cggctgctac ccgcttcatg aaggacctct attttactag tactaatggt   1080
gtcggtgaga tcggccgtgg gatagcgctt accctgttta accttgctga caccctgctt   1140
ggcggtctac cgacagaatt gatttcgtcg gctggtggcc agctgttcta ctctcgtccc   1200
gtcgtctcag ccaatggcga gccgactgtt aagctttata catctgtaga gaatgctcag   1260
caggataagg gtattgcaat cccgcatgac atcgacctcg gggagtctcg tgtagttatt   1320
caggattatg acaaccaaca tgagcaggac cgaccgacac cttccccagc ccatcgcgc    1380
cctttttctg tcctccgagc taatgatgtg ctttggcttt ctctcaccgc tgccgagtat   1440
gaccagtcca cttacggctc ttcgaccggc ccagtctatg tctctgactc tgtgaccttg   1500
gttaatgttg cgaccggcgc gcaggccgtt gcccggtcac tcgactggac caaggtcaca   1560
cttgatggtc gccccctttc caccatccag cagtattcaa agaccttctt tgtcctgccg   1620
ctccgcggta agctctccctt tgggaggca ggtactacta agccgggta ccccttataat    1680
tataacacca ctgctagtga ccaactgctc gttgagaatg ccgctgggca tcgggttgct   1740
atttccactt acaccactag cctgggtgct ggtcccgtct ctatttccgc ggttgctgtt   1800
ttagcccccc actccgcgct agcattgctt gaggatacca tggactaccc tgcccgcgcc   1860
catactttcg atgacttctg cccggagtgc cgccccttg gcctccaggg ctgtgctttt    1920
cagtctactg tcgctgagct tcagcgcctt aagatgaagg tgggtaaaac tcgggagtta   1980
tagtttattt                                                          1990
```

<210> SEQ ID NO 3
<211> LENGTH: 1989
<212> TYPE: DNA
<213> ORGANISM: Artificial sequence
<220> FEATURE:
<223> OTHER INFORMATION: sequence encoding polypeptide NE2

<400> SEQUENCE: 3

```
atgcgccctc ggcctatttt gctgttgctc tcatgtttc tgcctatgct gcccgcgcca     60
ccgcccggtc agccgtctgg ccgccgtcgt gggcggcgca gcggcggttc cggcggtggt    120
ttctggggtg accgggttga ttctcagccc ttcgcaatcc cctatattca tccaaccaac    180
cccttcgccc ccgatgtcac cgctgcggcc ggggctggac ctcgtgttcg ccaacccgcc    240
cgaccactcg gctccgcttg gcgtgaccag gcccagcgcc ccgccgttgc ctcacgtcgt    300
agacctacca cagctggggc cgcgccgcta accgcggtcg ctccggccca tgacaccccg   360
ccagtgcctg atgttgactc ccgcggcgcc atcctgcgcc ggcagtataa cctatcaaca    420
```

-continued

| | |
|---|---|
| tctcccctta cttcttccgt ggccaccggt acaaacttgg ttctatacgc cgctcctctt | 480 |
| agcccacttc taccccctcca ggacggcacc aatactcata taatggccac agaagcttct | 540 |
| aattatgccc agtaccgggt tgctcgtgcc acaattcgct accgcccgct ggtccccaac | 600 |
| gctgttggtg gctacgccat ctccatctcg ttctggccac agaccaccac caccccgacg | 660 |
| tccgttgaca tgaattcaat aacctcgacg gatgttcgta ttttagtcca gcccggcata | 720 |
| gcctccgagc ttgttatccc aagtgagcgc ctacactacc gtaaccaagg ttggcgctct | 780 |
| gttgagacct ccggggtggc ggaggaggag gccacctctg tcttgttat gctctgcata | 840 |
| catggctcac ctgtaaattc ttatactaat acaccttata ccggtgccct cgggctgttg | 900 |
| gactttgccc tcgaacttga gttccgcaac ctcaccccccg gtaataccaa acgcgggtc | 960 |
| tcccgttact ccagcactgc ccgtcaccgc cttcgtcgcg gtgcagatgg gactgccgag | 1020 |
| cttaccacca cggctgctac ccgcttcatg aaggacctct attttactag tactaatggt | 1080 |
| gtcggtgaga tcggccgtgg gatagcgctt accctgttta accttgctga caccctgctt | 1140 |
| ggcggtctac cgacagaatt gatttcgtcg gctggtggcc agctgttcta ctctcgtccc | 1200 |
| gtcgtctcag ccaatggcga gccgactgtt aagctttata catctgtaga gaatgctcag | 1260 |
| caggataagg gtattgcaat cccgcatgac atcgacctcg gggagtctcg tgtagttatt | 1320 |
| caggattatg acaaccaaca tgagcaggac cgaccgacac cttccccagc ccatcgcgc | 1380 |
| ccttttctg tcctccgagc taatgatgtg ctttggcttt ctctcaccgc tgccgagtat | 1440 |
| gaccagtcca cttacggctc ttcgaccggc ccagtctatg tctctgactc tgtgaccttg | 1500 |
| gttaatgttg cgaccggcgc gcaggccgtt gcccggtcac tcgactggac caaggtcaca | 1560 |
| cttgatggtc gccccctttc caccatccag cagtattcaa agaccttctt tgtcctgccg | 1620 |
| ctccgcggta agctctcctt tgggaggca ggtactacta agccgggta cccttataat | 1680 |
| tataacacca ctgctagtga ccaactgctc gttgagaatg ccgctgggca tcgggttgct | 1740 |
| atttccactt acaccactag cctgggtgct ggtcccgtct ctatttccgc ggttgctgtt | 1800 |
| ttagcccccc ctccgcgcta gcattgcttg aggataccat ggactaccct gcccgcgccc | 1860 |
| atactttcga tgacttctgc ccggagtgcc gccccttgg cctccagggc tgtgcttttc | 1920 |
| agtctactgt cgctgagctt cagcgcctta agatgaaggt gggtaaaact cgggagttat | 1980 |
| agtttattt | 1989 |

<210> SEQ ID NO 4
<211> LENGTH: 214
<212> TYPE: PRT
<213> ORGANISM: Artificial
<220> FEATURE:
<223> OTHER INFORMATION: synthetic peptide

<400> SEQUENCE: 4

Met Gln Leu Phe Tyr Ser Arg Pro Val Val Ser Ala Asn Gly Glu Pro
1               5                   10                  15

Thr Val Lys Leu Tyr Thr Ser Val Glu Asn Ala Gln Gln Asp Lys Gly
            20                  25                  30

Ile Ala Ile Pro His Asp Ile Asp Leu Gly Glu Ser Arg Val Val Ile
        35                  40                  45

Gln Asp Tyr Asp Asn Gln His Glu Gln Asp Arg Pro Thr Pro Ser Pro
    50                  55                  60

Ala Pro Ser Arg Pro Phe Ser Val Leu Arg Ala Asn Asp Val Leu Trp
65                  70                  75                  80

Leu Ser Leu Thr Ala Ala Glu Tyr Asp Gln Ser Thr Tyr Gly Ser Ser
                85                  90                  95

Thr Gly Pro Val Tyr Val Ser Asp Ser Val Thr Leu Val Asn Val Ala
            100                 105                 110

Thr Gly Ala Gln Ala Val Ala Arg Ser Leu Asp Trp Thr Lys Val Thr
        115                 120                 125

Leu Asp Gly Arg Pro Leu Ser Thr Ile Gln Gln His Ser Lys Thr Phe
    130                 135                 140

Phe Val Leu Pro Leu Arg Gly Lys Leu Ser Phe Trp Glu Ala Gly Thr
145                 150                 155                 160

Thr Lys Ala Gly Tyr Pro Tyr Asn Tyr Asn Thr Thr Ala Ser Asp Gln
                165                 170                 175

Leu Leu Val Glu Asn Ala Ala Gly His Arg Val Ala Ile Ser Thr Tyr
            180                 185                 190

Thr Thr Ser Leu Gly Ala Gly Pro Val Ser Ile Ser Ala Val Ala Val
        195                 200                 205

Leu Ala Pro Pro Pro Arg
    210

<210> SEQ ID NO 5
<211> LENGTH: 324
<212> TYPE: DNA
<213> ORGANISM: Balb/C mouse

<400> SEQUENCE: 5
gacatccaga tgactcagtc tccagcctcc ctatctgtat ctgtgggaga aactgtcacc    60
atcacatgtc gagcaagtga gaatatttac agtaatttag catggtatca gcagaaacag   120
ggaaaatctc ctcagctcct ggtctatgct gcaacaaact tagcagatgg tgtgccatca   180
aggttcagtg gcagtggatc aggcacacag tattccctca agatcagcag cctgcagtct   240
gaagattttg ggagttatta ctgtcaacat ttttgggggtt ctccgtggac gttcggtgga   300
ggcaccaagc tggaaatcaa acgg                                           324

<210> SEQ ID NO 6
<211> LENGTH: 108
<212> TYPE: PRT
<213> ORGANISM: Balb/C mouse

<400> SEQUENCE: 6

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Ser Ser Leu Gln Ser
65                  70                  75                  80

Glu Asp Phe Gly Ser Tyr Tyr Cys Gln His Phe Trp Gly Ser Pro Trp
                85                  90                  95

Thr Phe Gly Gly Gly Thr Lys Leu Glu Ile Lys Arg
            100                 105

<210> SEQ ID NO 7

<211> LENGTH: 351
<212> TYPE: DNA
<213> ORGANISM: Balb/C mouse

<400> SEQUENCE: 7

```
gatgtacaac ttcaggagtc aggacctggc ctcgtgaaac cttctcagtc tctgtctctc    60
tcctgctctg tcactggcta ctccatcacc agtggttatt actggaactg gatccggcag   120
tttccaggaa acaaactgga atggatgggc tacataggct acgacggtag caataagtac   180
aacccatctc tcaaaaatcg aatctccatc actcgtgaca catctaagaa ccagttttc    240
ctgaagttga cttctgtgac tactggggac acagctacat attactgtgt aagagatgtt   300
aagtactact ttgactactg gggtcaaggc accacggtca ccgtatcttc a            351
```

<210> SEQ ID NO 8
<211> LENGTH: 117
<212> TYPE: PRT
<213> ORGANISM: Balb/C mouse

<400> SEQUENCE: 8

```
Asp Val Gln Leu Gln Glu Ser Gly Pro Gly Leu Val Lys Pro Ser Gln
1               5                   10                  15

Ser Leu Ser Leu Ser Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Gly Tyr Asp Gly Ser Asn Lys Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Thr Ser Val Thr Thr Gly Asp Thr Ala Thr Tyr Tyr Cys
                85                  90                  95

Val Arg Asp Val Lys Tyr Tyr Phe Asp Tyr Trp Gly Gln Gly Thr Thr
            100                 105                 110

Val Thr Val Ser Ser
        115
```

<210> SEQ ID NO 9
<211> LENGTH: 324
<212> TYPE: DNA
<213> ORGANISM: Balb/C mouse

<400> SEQUENCE: 9

```
gacatccaga tgactcagtc tccagcctcc ctatctgtat ctgtgggaga aactgtcacc    60
atcacatgtc gagcaagtga gatttattac agtaatttag catggtatca gcagaaacag   120
ggaaaatctc ctcagctcct ggtctattct gcaacaaact agctgaagg tgtgccatca    180
aggttcagtg gcagtggatc aggcacacag tattccctca agatcaacag cctgcagtct   240
gaagatttg ggagttatta ctgtcaacat ttttggggta atccgtggac gttcggtgga    300
ggcaccaagc tggaaatcaa acgg                                          324
```

<210> SEQ ID NO 10
<211> LENGTH: 108
<212> TYPE: PRT
<213> ORGANISM: Balb/C mouse

<400> SEQUENCE: 10

```
Asp Ile Gln Met Thr Gln Ser Pro Ala Ser Leu Ser Val Ser Val Gly
```

```
                1               5                  10                 15
         Glu Thr Val Thr Ile Thr Cys Arg Ala Ser Glu Ile Ile Tyr Ser Asn
                         20                  25                  30

Leu Ala Trp Tyr Gln Gln Lys Gln Gly Lys Ser Pro Gln Leu Leu Val
                         35                  40                  45

Tyr Ser Ala Thr Asn Leu Ala Glu Gly Val Pro Ser Arg Phe Ser Gly
                         50                  55                  60

Ser Gly Ser Gly Thr Gln Tyr Ser Leu Lys Ile Asn Ser Leu Gln Ser
          65                  70                  75                  80

Glu Asp Phe Gly Ser Tyr Tyr Cys Gln His Phe Trp Gly Asn Pro Trp
                         85                  90                  95

Thr Phe Gly Gly Gly Thr Lys Leu Glu Ile Lys Arg
                         100                 105
```

<210> SEQ ID NO 11
<211> LENGTH: 372
<212> TYPE: DNA
<213> ORGANISM: Balb/C mouse

<400> SEQUENCE: 11

```
caggttactc tgaaagagtc tggccctggg atattgcagc cctcccagac cctcagtctg      60
acttgttctt tctctgggtt ttcactgagc acttctggta tgggtgtagg ctggattcgt     120
cagccatcag ggaagggtct ggagtggctg gcacacattt ggtgggatga tgtcaagcgc     180
tatagcccag ccctgaagag ccgactgact atctccaagg ataccttcag cagccagcta     240
ttcctcaaga tcgccagtgt ggacactgca gatactgcca catactactg tgctcgaatc     300
aagagtgtga ttacgacggg ggactatgct ttggactact ggggtcaagg aacctcagtc     360
gccgtctcct ca                                                        372
```

<210> SEQ ID NO 12
<211> LENGTH: 124
<212> TYPE: PRT
<213> ORGANISM: Balb/C mouse

<400> SEQUENCE: 12

```
         Gln Val Thr Leu Lys Glu Ser Gly Pro Gly Ile Leu Gln Pro Ser Gln
          1               5                  10                 15

Thr Leu Ser Leu Thr Cys Ser Phe Ser Gly Phe Ser Leu Ser Thr Ser
                         20                  25                  30

Gly Met Gly Val Gly Trp Ile Arg Gln Pro Ser Gly Lys Gly Leu Glu
                         35                  40                  45

Trp Leu Ala His Ile Trp Trp Asp Asp Val Lys Arg Tyr Ser Pro Ala
                         50                  55                  60

Leu Lys Ser Arg Leu Thr Ile Ser Lys Asp Thr Ser Ser Ser Gln Leu
          65                  70                  75                  80

Phe Leu Lys Ile Ala Ser Val Asp Thr Ala Asp Thr Ala Thr Tyr Tyr
                         85                  90                  95

Cys Ala Arg Ile Lys Ser Val Ile Thr Thr Gly Asp Tyr Ala Leu Asp
                         100                 105                 110

Tyr Trp Gly Gln Gly Thr Ser Val Ala Val Ser Ser
                         115                 120
```

<210> SEQ ID NO 13
<211> LENGTH: 339
<212> TYPE: DNA
<213> ORGANISM: Balb/C mouse

<400> SEQUENCE: 13

```
aacattatga tgacacagtc gccatcatct ctggctgtgt ctgcaggaga aaaggtcact      60
atgagctgta agtccagtca aagtgtttta tacagttcaa atcagaagaa ctacttggcc     120
tggtaccagc agaaaccagg gcagtctcct aaactgctga tctactgggc atccgctagg    180
gaatctggtg tccctgatcg cttcacaggc agtggatccg ggacagattt tactcttacc    240
atcaacagtg tacaaactga agacctggca gtttattact gtcatcaata cctctcctcg    300
tacacgttcg gaggggggac caagctggaa ataaaacgg                             339
```

<210> SEQ ID NO 14
<211> LENGTH: 113
<212> TYPE: PRT
<213> ORGANISM: Balb/C mouse

<400> SEQUENCE: 14

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Thr Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
            100                 105                 110

Arg

<210> SEQ ID NO 15
<211> LENGTH: 351
<212> TYPE: DNA
<213> ORGANISM: Balb/C mouse

<400> SEQUENCE: 15

```
caggtgcagc tgaaggagtc aggacctggc ctggtggcgc cctcacagag cctgtccatc      60
acatgcaccg tctcagggtt ctcattaatc ggctatggtg taaactgggt tcgccagcct    120
ccagaaaagg gtctggagtg gctgggaatg atatggggtg atggaagcac agactataat    180
tcagctctca aatccagact gagcatcacc aaggacaact ccaagagcca gttttctta     240 aaaatgaaca gtctgcaaac tgatgacaca gccaggtact actgtgccat ggggtacga     300 ccggaccctt ttgattactg gggccaaggg actctggtca ctgtctctgc a             351
```

<210> SEQ ID NO 16
<211> LENGTH: 117
<212> TYPE: PRT
<213> ORGANISM: Balb/C mouse

<400> SEQUENCE: 16

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Gly Tyr
            20                  25                  30

```
Gly Val Asn Trp Val Arg Gln Pro Pro Glu Lys Gly Leu Glu Trp Leu
            35                  40                  45
Gly Met Ile Trp Gly Asp Gly Ser Thr Asp Tyr Asn Ser Ala Leu Lys
        50                  55                  60
Ser Arg Leu Ser Ile Thr Lys Asp Asn Ser Lys Ser Gln Val Phe Leu
65                  70                  75                  80
Lys Met Asn Ser Leu Gln Thr Asp Asp Thr Ala Arg Tyr Tyr Cys Ala
                85                  90                  95
Met Gly Val Arg Pro Asp Pro Phe Asp Tyr Trp Gly Gln Gly Thr Leu
            100                 105                 110
Val Thr Val Ser Ala
        115

<210> SEQ ID NO 17
<211> LENGTH: 339
<212> TYPE: DNA
<213> ORGANISM: Balb/C mouse

<400> SEQUENCE: 17
gatgttgtga tgacccagac tccactgtct ttgtcggtta ccattggaca accagcctct      60
atctcttgca gtcaagtca  gagcctctta tatcgtaatg aaagatata  tttgaattgg     120 ttacaacaga ggcctggcca ggctccaaag cacctaatgt ctcaggtgtc caaactggac     180
cctggcatcc ctgacaggtt cagtggcagt ggatcagaaa cagattttac acttaaaatc     240
agcagagtgg aggctgaaga tttgggagtt tattactgct tgcaaggtac acattacccg     300
tacacgtttg gaggggggac caagctggaa ataaaacgg                            339

<210> SEQ ID NO 18
<211> LENGTH: 113
<212> TYPE: PRT
<213> ORGANISM: Balb/C mouse

<400> SEQUENCE: 18

Asp Val Val Met Thr Gln Thr Pro Leu Ser Leu Ser Val Thr Ile Gly
1               5                   10                  15
Gln Pro Ala Ser Ile Ser Cys Lys Ser Ser Gln Ser Leu Leu Tyr Arg
            20                  25                  30
Asn Gly Lys Ile Tyr Leu Asn Trp Leu Gln Gln Arg Pro Gly Gln Ala
        35                  40                  45
Pro Lys His Leu Met Ser Gln Val Ser Lys Leu Asp Pro Gly Ile Pro
    50                  55                  60
Asp Arg Phe Ser Gly Ser Gly Ser Glu Thr Asp Phe Thr Leu Lys Ile
65                  70                  75                  80
Ser Arg Val Glu Ala Glu Asp Leu Gly Val Tyr Tyr Cys Leu Gln Gly
                85                  90                  95
Thr His Tyr Pro Tyr Thr Phe Gly Gly Gly Thr Lys Leu Glu Ile Lys
            100                 105                 110
Arg

<210> SEQ ID NO 19
<211> LENGTH: 348
<212> TYPE: DNA
<213> ORGANISM: Balb/C mouse

<400> SEQUENCE: 19
gaggtccagc tgcagcagtc tggacctgag ctggtaaagc ctggggcttc agtgaagatg      60
```

-continued

```
tcctgcaagg cttctggata taaattcact agctatgtta tgcactgggt gaagcagaag      120
cctgggcagg gccttgagtg gattggatat attaatcctt ccaatgataa tattaagtac      180
aatgagaagt tcaaaggcaa ggccatactg actttagaca atcctccag cacagcctac       240 atggcgttca gcagcctgac ctctgaggac tctgcggtct attactgtgc aaccttaact      300
ggggttgact actggggcca aggcaccact ctcacagtct cctcagcc                   348
```

```
<210> SEQ ID NO 20
<211> LENGTH: 116
<212> TYPE: PRT
<213> ORGANISM: Balb/C mouse

<400> SEQUENCE: 20
```

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Lys Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Ser Asn Asp Asn Ile Lys Tyr Asn Glu Lys Phe
    50                  55                  60

Lys Gly Lys Ala Ile Leu Thr Leu Asp Lys Ser Ser Ser Thr Ala Tyr
65                  70                  75                  80

Met Ala Phe Ser Ser Leu Thr Ser Glu Asp Ser Ala Val Tyr Tyr Cys
                85                  90                  95

Ala Thr Leu Thr Gly Val Asp Tyr Trp Gly Gln Gly Thr Thr Leu Thr
            100                 105                 110

Val Ser Ser Ala
        115

```
<210> SEQ ID NO 21
<211> LENGTH: 240
<212> TYPE: PRT
<213> ORGANISM: Artificial
<220> FEATURE:
<223> OTHER INFORMATION: synthetic peptide

<400> SEQUENCE: 21
```

Met Ile Ala Leu Thr Leu Phe Asn Leu Ala Asp Thr Leu Leu Gly Gly
1               5                   10                  15

Leu Pro Thr Glu Leu Ile Ser Ser Ala Gly Gly Gln Leu Phe Tyr Ser
            20                  25                  30

Arg Pro Val Val Ser Ala Asn Gly Glu Pro Thr Val Lys Leu Tyr Thr
        35                  40                  45

Ser Val Glu Asn Ala Gln Gln Asp Lys Gly Ile Ala Ile Pro His Asp
    50                  55                  60

Ile Asp Leu Gly Glu Ser Arg Val Val Ile Gln Tyr Asp Asn Gln
65                  70                  75                  80

His Glu Gln Asp Arg Pro Thr Pro Ser Pro Ala Pro Ser Arg Pro Phe
                85                  90                  95

Ser Val Leu Arg Ala Asn Asp Val Leu Trp Leu Ser Leu Thr Ala Ala
            100                 105                 110

Glu Tyr Asp Gln Ser Thr Tyr Gly Ser Ser Thr Gly Pro Val Tyr Val
        115                 120                 125

Ser Asp Ser Val Thr Leu Val Asn Val Ala Thr Gly Ala Gln Ala Val
    130                 135                 140

```
Ala Arg Ser Leu Asp Trp Thr Lys Val Thr Leu Asp Gly Arg Pro Leu
145                 150                 155                 160

Ser Thr Ile Gln Gln His Ser Lys Thr Phe Phe Val Leu Pro Leu Arg
                165                 170                 175

Gly Lys Leu Ser Phe Trp Glu Ala Gly Thr Thr Lys Ala Gly Tyr Pro
            180                 185                 190

Tyr Asn Tyr Asn Thr Thr Ala Ser Asp Gln Leu Leu Val Glu Asn Ala
        195                 200                 205

Ala Gly His Arg Val Ala Ile Ser Thr Tyr Thr Thr Ser Leu Gly Ala
    210                 215                 220

Gly Pro Val Ser Ile Ser Ala Val Ala Val Leu Ala Pro Pro Pro Arg
225                 230                 235                 240

<210> SEQ ID NO 22
<211> LENGTH: 258
<212> TYPE: PRT
<213> ORGANISM: Artificial
<220> FEATURE:
<223> OTHER INFORMATION: synthetic peptide

<400> SEQUENCE: 22

Met Ala Ala Thr Arg Phe Met Lys Asp Leu Tyr Phe Thr Ser Thr Asn
1               5                   10                  15

Gly Val Gly Glu Ile Gly Arg Gly Ile Ala Leu Thr Leu Phe Asn Leu
            20                  25                  30

Ala Asp Thr Leu Leu Gly Gly Leu Pro Thr Glu Leu Ile Ser Ser Ala
        35                  40                  45

Gly Gly Gln Leu Phe Tyr Ser Arg Pro Val Val Ser Ala Asn Gly Glu
    50                  55                  60

Pro Thr Val Lys Leu Tyr Thr Ser Val Glu Asn Ala Gln Gln Asp Lys
65                  70                  75                  80

Gly Ile Ala Ile Pro His Asp Ile Asp Leu Gly Glu Ser Arg Val Val
                85                  90                  95

Ile Gln Asp Tyr Asp Asn Gln His Glu Gln Asp Arg Pro Thr Pro Ser
            100                 105                 110

Pro Ala Pro Ser Arg Pro Phe Ser Val Leu Arg Ala Asn Asp Val Leu
        115                 120                 125

Trp Leu Ser Leu Thr Ala Ala Glu Tyr Asp Gln Ser Thr Tyr Gly Ser
    130                 135                 140

Ser Thr Gly Pro Val Tyr Val Ser Asp Ser Val Thr Leu Val Asn Val
145                 150                 155                 160

Ala Thr Gly Ala Gln Ala Val Ala Arg Ser Leu Asp Trp Thr Lys Val
                165                 170                 175

Thr Leu Asp Gly Arg Pro Leu Ser Thr Ile Gln Gln His Ser Lys Thr
            180                 185                 190

Phe Phe Val Leu Pro Leu Arg Gly Lys Leu Ser Phe Trp Glu Ala Gly
        195                 200                 205

Thr Thr Lys Ala Gly Tyr Pro Tyr Asn Tyr Asn Thr Thr Ala Ser Asp
    210                 215                 220

Gln Leu Leu Val Glu Asn Ala Ala Gly His Arg Val Ala Ile Ser Thr
225                 230                 235                 240

Tyr Thr Thr Ser Leu Gly Ala Gly Pro Val Ser Ile Ser Ala Val Ala
                245                 250                 255

Val Leu
```

<210> SEQ ID NO 23
<211> LENGTH: 245
<212> TYPE: PRT
<213> ORGANISM: Artificial
<220> FEATURE:
<223> OTHER INFORMATION: synthetic peptide

<400> SEQUENCE: 23

```
Met Ile Gly Arg Gly Ile Ala Leu Thr Leu Phe Asn Leu Ala Asp Thr
1               5                   10                  15

Leu Leu Gly Gly Leu Pro Thr Glu Leu Ile Ser Ser Ala Gly Gly Gln
            20                  25                  30

Leu Phe Tyr Ser Arg Pro Val Val Ser Ala Asn Gly Glu Pro Thr Val
        35                  40                  45

Ala Lys Leu Tyr Thr Ser Val Glu Asn Ala Gln Gln Asp Lys Gly Ile
50                  55                  60

Ala Ile Pro His Asp Ile Asp Leu Gly Glu Ser Arg Val Val Ile Gln
65                  70                  75                  80

Asp Tyr Asp Asn Gln His Glu Gln Asp Arg Pro Thr Pro Ser Pro Ala
                85                  90                  95

Pro Ser Arg Pro Phe Ser Val Leu Arg Ala Asn Asp Val Leu Trp Leu
            100                 105                 110

Ser Leu Thr Ala Ala Glu Tyr Asp Gln Ser Thr Tyr Gly Ser Ser Thr
        115                 120                 125

Gly Pro Val Tyr Val Ser Asp Ser Val Thr Leu Val Asn Val Ala Thr
130                 135                 140

Gly Ala Gln Ala Val Ala Arg Ser Leu Asp Trp Thr Lys Val Thr Leu
145                 150                 155                 160

Asp Gly Arg Pro Leu Ser Thr Ile Gln Gln His Ser Lys Thr Phe Phe
                165                 170                 175

Val Leu Pro Leu Arg Gly Lys Leu Ser Phe Trp Glu Ala Gly Thr Thr
            180                 185                 190

Lys Ala Gly Tyr Pro Tyr Asn Tyr Asn Thr Thr Ala Ser Asp Gln Leu
        195                 200                 205

Leu Val Glu Asn Ala Ala Gly His Arg Val Ala Ile Ser Thr Tyr Thr
210                 215                 220

Thr Ser Leu Gly Ala Gly Pro Val Ser Ile Ser Ala Val Ala Val Leu
225                 230                 235                 240

Ala Pro Pro Pro Arg
            245
```

<210> SEQ ID NO 24
<211> LENGTH: 253
<212> TYPE: PRT
<213> ORGANISM: Artificial
<220> FEATURE:
<223> OTHER INFORMATION: synthetic peptide

<400> SEQUENCE: 24

```
Met Thr Ser Thr Asn Gly Val Gly Glu Ile Gly Arg Gly Ile Ala Leu
1               5                   10                  15

Thr Leu Phe Asn Leu Ala Asp Thr Leu Leu Gly Gly Leu Pro Thr Glu
            20                  25                  30

Leu Ile Ser Ser Ala Gly Gly Gln Leu Phe Tyr Ser Arg Pro Val Val
        35                  40                  45

Ser Ala Asn Gly Glu Pro Thr Val Lys Leu Tyr Thr Ser Val Glu Asn
50                  55                  60
```

```
Ala Gln Gln Asp Lys Gly Ile Ala Ile Pro His Asp Ile Asp Leu Gly
 65                  70                  75                  80

Glu Ser Arg Val Val Ile Gln Asp Tyr Asp Asn Gln His Glu Gln Asp
                 85                  90                  95

Arg Pro Thr Pro Ser Pro Ala Pro Ser Arg Pro Phe Ser Val Leu Arg
            100                 105                 110

Ala Asn Asp Val Leu Trp Leu Ser Leu Thr Ala Ala Glu Tyr Asp Gln
        115                 120                 125

Ser Thr Tyr Gly Ser Ser Thr Gly Pro Val Tyr Val Ser Asp Ser Val
130                 135                 140

Thr Leu Val Asn Val Ala Thr Gly Ala Gln Ala Val Ala Arg Ser Leu
145                 150                 155                 160

Asp Trp Thr Lys Val Thr Leu Asp Gly Arg Pro Leu Ser Thr Ile Gln
                165                 170                 175

Gln His Ser Lys Thr Phe Phe Val Leu Pro Leu Arg Gly Lys Leu Ser
            180                 185                 190

Phe Trp Glu Ala Gly Thr Thr Lys Ala Gly Tyr Pro Tyr Asn Tyr Asn
        195                 200                 205

Thr Thr Ala Ser Asp Gln Asn Leu Leu Val Glu Asn Ala Ala Gly His
210                 215                 220

Arg Val Ala Ile Ser Thr Tyr Thr Thr Ser Leu Gly Ala Gly Pro Val
225                 230                 235                 240

Ser Ile Ser Ala Val Ala Val Leu Ala Pro Pro Arg
                245                 250

<210> SEQ ID NO 25
<211> LENGTH: 263
<212> TYPE: PRT
<213> ORGANISM: Artificial
<220> FEATURE:
<223> OTHER INFORMATION: synthetic peptide

<400> SEQUENCE: 25

Met Ala Ala Thr Arg Phe Met Lys Asp Leu Tyr Phe Thr Ser Thr Asn
  1               5                  10                  15

Gly Val Gly Glu Ile Gly Arg Gly Ile Ala Leu Thr Leu Phe Asn Leu
                 20                  25                  30

Ala Asp Thr Leu Leu Gly Gly Leu Pro Thr Glu Leu Ile Ser Ser Ala
            35                  40                  45

Gly Gly Gln Leu Phe Tyr Ser Arg Pro Val Val Ser Ala Asn Gly Glu
        50                  55                  60

Pro Thr Val Lys Leu Tyr Thr Ser Val Glu Asn Ala Gln Gln Asp Lys
 65                  70                  75                  80

Gly Ile Ala Ile Pro His Asp Ile Asp Leu Gly Glu Ser Arg Val Val
                 85                  90                  95

Ile Gln Asp Tyr Asp Asn Gln His Glu Gln Asp Arg Pro Thr Pro Ser
            100                 105                 110

Pro Ala Pro Ser Arg Pro Phe Ser Val Leu Arg Ala Asn Asp Val Leu
        115                 120                 125

Trp Leu Ser Leu Thr Ala Ala Glu Tyr Asp Gln Ser Thr Tyr Gly Ser
130                 135                 140

Ser Thr Gly Pro Val Tyr Val Ser Asp Ser Val Thr Leu Val Asn Val
145                 150                 155                 160

Ala Thr Gly Ala Gln Ala Val Ala Arg Ser Leu Asp Trp Thr Lys Val
                165                 170                 175
```

Thr Leu Asp Gly Arg Pro Leu Ser Thr Ile Gln Gln His Ser Lys Thr
            180                 185                 190

Phe Phe Val Leu Pro Leu Arg Gly Lys Leu Ser Phe Trp Glu Ala Gly
        195                 200                 205

Thr Thr Lys Ala Gly Tyr Pro Tyr Asn Tyr Asn Thr Thr Ala Ser Asp
210                 215                 220

Gln Leu Leu Val Glu Asn Ala Ala Gly His Arg Val Ala Ile Ser Thr
225                 230                 235                 240

Tyr Thr Thr Ser Leu Gly Ala Gly Pro Val Ser Ile Ser Ala Val Ala
                245                 250                 255

Val Leu Ala Pro Pro Arg
            260

<210> SEQ ID NO 26
<211> LENGTH: 290
<212> TYPE: PRT
<213> ORGANISM: Artificial
<220> FEATURE:
<223> OTHER INFORMATION: synthetic peptide

<400> SEQUENCE: 26

Met Ile Ala Leu Thr Leu Phe Asn Leu Ala Asp Thr Leu Leu Gly Gly
1               5                   10                  15

Leu Pro Thr Glu Leu Ile Ser Ser Ala Gly Gly Gln Leu Phe Tyr Ser
            20                  25                  30

Arg Pro Val Val Ser Ala Asn Gly Glu Pro Thr Val Lys Leu Tyr Thr
        35                  40                  45

Ser Val Glu Asn Ala Gln Gln Asp Lys Gly Ile Ala Ile Pro His Asp
    50                  55                  60

Ile Asp Leu Gly Glu Ser Arg Val Val Ile Gln Asp Tyr Asp Asn Gln
65                  70                  75                  80

His Glu Gln Asp Arg Pro Thr Pro Ser Pro Ala Pro Ser Arg Pro Phe
                85                  90                  95

Ser Val Leu Arg Ala Asn Asp Val Leu Trp Leu Ser Leu Thr Ala Ala
            100                 105                 110

Glu Tyr Asp Gln Ser Thr Tyr Gly Ser Ser Thr Gly Pro Val Tyr Val
        115                 120                 125

Ser Asp Ser Val Thr Leu Val Asn Val Ala Thr Gly Ala Gln Ala Val
130                 135                 140

Ala Arg Ser Leu Asp Trp Thr Lys Val Thr Leu Asp Gly Arg Pro Leu
145                 150                 155                 160

Ser Thr Ile Gln Gln His Ser Lys Thr Phe Phe Val Leu Pro Leu Arg
                165                 170                 175

Gly Lys Leu Ser Phe Trp Glu Ala Gly Thr Thr Lys Ala Gly Tyr Pro
            180                 185                 190

Tyr Asn Tyr Asn Thr Thr Ala Ser Asp Gln Leu Leu Val Glu Asn Ala
        195                 200                 205

Ala Gly His Arg Val Ala Ile Ser Thr Tyr Thr Thr Ser Leu Gly Ala
    210                 215                 220

Gly Pro Val Ser Ile Ser Ala Val Ala Val Leu Ala Pro His Ser Val
225                 230                 235                 240

Ala Leu Leu Glu Asp Thr Met Asp Tyr Pro Ala Arg Ala His Thr Asp
                245                 250                 255

Asp Phe Cys Pro Glu Cys Arg Pro Leu Gly Leu Gln Gly Cys Phe Gln
            260                 265                 270

-continued

```
Ser Thr Val Ala Glu Leu Gln Arg Leu Lys Met Lys Val Lys Thr Arg
        275                 280                 285

Glu Leu
    290

<210> SEQ ID NO 27
<211> LENGTH: 7
<212> TYPE: PRT
<213> ORGANISM: Artificial
<220> FEATURE:
<223> OTHER INFORMATION: synthetic peptide

<400> SEQUENCE: 27

His Pro Thr Leu Leu Arg Ile
1               5

<210> SEQ ID NO 28
<211> LENGTH: 7
<212> TYPE: PRT
<213> ORGANISM: Artificial
<220> FEATURE:
<223> OTHER INFORMATION: synthetic peptide

<400> SEQUENCE: 28

Ala Leu Trp Gly Pro Thr Ser
1               5

<210> SEQ ID NO 29
<211> LENGTH: 7
<212> TYPE: PRT
<213> ORGANISM: Artificial
<220> FEATURE:
<223> OTHER INFORMATION: synthetic peptide

<400> SEQUENCE: 29

Ser Ile Leu Pro Tyr Pro Tyr
1               5

<210> SEQ ID NO 30
<211> LENGTH: 175
<212> TYPE: PRT
<213> ORGANISM: Artificial
<220> FEATURE:
<223> OTHER INFORMATION: synthetic peptide

<400> SEQUENCE: 30

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser His Pro Thr Leu Leu Arg
                85                  90                  95

Ile Gly Gly Gly Gly Ser Gly Gly Gly Ser Arg Glu Leu Val Val
            100                 105                 110

Ser Tyr Val Asn Val Asn Met Gly Leu Lys Ile Arg Gln Leu Leu Trp
        115                 120                 125
```

```
Phe His Ile Ser Cys Leu Thr Phe Gly Arg Glu Thr Val Leu Glu Tyr
        130                 135                 140

Leu Val Ser Phe Gly Val Trp Ile Arg Thr Pro Pro Ala Tyr Arg Pro
145                 150                 155                 160

Gln Asn Ala Pro Ile Leu Ser Thr Leu Pro Glu Thr Thr Val Val
                165                 170                 175

<210> SEQ ID NO 31
<211> LENGTH: 175
<212> TYPE: PRT
<213> ORGANISM: Artificial
<220> FEATURE:
<223> OTHER INFORMATION: synthetic peptide

<400> SEQUENCE: 31

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Ser Ile Leu Pro Tyr Pro
                85                  90                  95

Tyr Gly Gly Gly Gly Ser Gly Gly Gly Gly Ser Arg Glu Leu Val Val
            100                 105                 110

Ser Tyr Val Asn Val Asn Met Gly Leu Lys Ile Arg Gln Leu Leu Trp
        115                 120                 125

Phe His Ile Ser Cys Leu Thr Phe Gly Arg Glu Thr Val Leu Glu Tyr
    130                 135                 140

Leu Val Ser Phe Gly Val Trp Ile Arg Thr Pro Pro Ala Tyr Arg Pro
145                 150                 155                 160

Gln Asn Ala Pro Ile Leu Ser Thr Leu Pro Glu Thr Thr Val Val
                165                 170                 175

<210> SEQ ID NO 32
<211> LENGTH: 15
<212> TYPE: DNA
<213> ORGANISM: Artificial sequence
<220> FEATURE:
<223> OTHER INFORMATION: primer

<400> SEQUENCE: 32
atgcgccctc ggcca                                                    15

<210> SEQ ID NO 33
<211> LENGTH: 20
<212> TYPE: DNA
<213> ORGANISM: Artificial sequence
<220> FEATURE:
<223> OTHER INFORMATION: primer

<400> SEQUENCE: 33
aaataaacta taactcccga                                               20

<210> SEQ ID NO 34
```

```
<211> LENGTH: 30
<212> TYPE: DNA
<213> ORGANISM: Artificial sequence
<220> FEATURE:
<223> OTHER INFORMATION: primer

<400> SEQUENCE: 34
ggatccatat gcagctgttc tactctcgtc                                            30

<210> SEQ ID NO 35
<211> LENGTH: 26
<212> TYPE: DNA
<213> ORGANISM: Artificial sequence
<220> FEATURE:
<223> OTHER INFORMATION: primer

<400> SEQUENCE: 35
ctcgagaaat aaactataac tcccga                                                26

<210> SEQ ID NO 36
<211> LENGTH: 21
<212> TYPE: DNA
<213> ORGANISM: Artificial sequence
<220> FEATURE:
<223> OTHER INFORMATION: primer

<400> SEQUENCE: 36
ggctcaccgg agtgtttctt c                                                     21

<210> SEQ ID NO 37
<211> LENGTH: 22
<212> TYPE: DNA
<213> ORGANISM: Artificial sequence
<220> FEATURE:
<223> OTHER INFORMATION: primer

<400> SEQUENCE: 37
ctttgatgac accgtcttct cg                                                    22

<210> SEQ ID NO 38
<211> LENGTH: 21
<212> TYPE: DNA
<213> ORGANISM: Artificial sequence
<220> FEATURE:
<223> OTHER INFORMATION: primer

<400> SEQUENCE: 38
gccgcagcaa aggcatccat g                                                     21

<210> SEQ ID NO 39
<211> LENGTH: 22
<212> TYPE: DNA
<213> ORGANISM: Artificial sequence
<220> FEATURE:
<223> OTHER INFORMATION: primer

<400> SEQUENCE: 39
gtgtttcttc caaaaccctc gc                                                    22

<210> SEQ ID NO 40
<211> LENGTH: 21
<212> TYPE: DNA
<213> ORGANISM: Artificial sequence
<220> FEATURE:
<223> OTHER INFORMATION: primer

<400> SEQUENCE: 40
```
ggctcaccgg agtgtttctt c                                             21

<210> SEQ ID NO 41
<211> LENGTH: 22
<212> TYPE: DNA
<213> ORGANISM: Artificial sequence
<220> FEATURE:
<223> OTHER INFORMATION: primer

<400> SEQUENCE: 41
ctttgatgac accgtcttct cg                                            22

<210> SEQ ID NO 42
<211> LENGTH: 21
<212> TYPE: DNA
<213> ORGANISM: Artificial sequence
<220> FEATURE:
<223> OTHER INFORMATION: primer

<400> SEQUENCE: 42
gccgcagcaa aggcatccat g                                             21

<210> SEQ ID NO 43
<211> LENGTH: 22
<212> TYPE: DNA
<213> ORGANISM: Artificial sequence
<220> FEATURE:
<223> OTHER INFORMATION: primer

<400> SEQUENCE: 43
gtgtttcttc caaaccctc gc                                             22

<210> SEQ ID NO 44
<211> LENGTH: 28
<212> TYPE: DNA
<213> ORGANISM: Artificial sequence
<220> FEATURE:
<223> OTHER INFORMATION: primer

<400> SEQUENCE: 44
tctagaatta acactcattc ctgttgaa                                      28

<210> SEQ ID NO 45
<211> LENGTH: 27
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is c or t
<220> FEATURE:
<221> NAME/KEY: misc_feature
<222> LOCATION: (9)..(9)
<223> OTHER INFORMATION: n is c or t
<220> FEATURE:
<221> NAME/KEY: misc_feature
<222> LOCATION: (12)..(12)
<223> OTHER INFORMATION: n is a, c, or g
<220> FEATURE:
<221> NAME/KEY: misc_feature
<222> LOCATION: (15)..(15)
<223> OTHER INFORMATION: n is a or g

<400> SEQUENCE: 45
atggtnctna tnttnctgct gctatgg                                       27

```
<210> SEQ ID NO 46
<211> LENGTH: 35
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: n is a or g
<220> FEATURE:
<221> NAME/KEY: misc_feature
<222> LOCATION: (20)..(20)
<223> OTHER INFORMATION: n is a or g
<220> FEATURE:
<221> NAME/KEY: misc_feature
<222> LOCATION: (21)..(21)
<223> OTHER INFORMATION: n is g or t
<220> FEATURE:
<221> NAME/KEY: misc_feature
<222> LOCATION: (27)..(27)
<223> OTHER INFORMATION: n is a or g
<220> FEATURE:
<221> NAME/KEY: misc_feature
<222> LOCATION: (30)..(30)
<223> OTHER INFORMATION: n is a, c, t or g
<220> FEATURE:
<221> NAME/KEY: misc_feature
<222> LOCATION: (32)..(32)
<223> OTHER INFORMATION: n is a or g

<400> SEQUENCE: 46
cccaagcttc cagggnccan nggatanacn gntgg                               35

<210> SEQ ID NO 47
<211> LENGTH: 33
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, or g
<220> FEATURE:
<221> NAME/KEY: misc_feature
<222> LOCATION: (14)..(14)
<223> OTHER INFORMATION: n is c or g
<220> FEATURE:
<221> NAME/KEY: misc_feature
<222> LOCATION: (21)..(21)
<223> OTHER INFORMATION: n is a or c
<220> FEATURE:
<221> NAME/KEY: misc_feature
<222> LOCATION: (27)..(27)
<223> OTHER INFORMATION: n is c or t

<400> SEQUENCE: 47
cgacatggnt tggntgtgga ncttgcnatt cct                                 33

<210> SEQ ID NO 48
<211> LENGTH: 22
<212> TYPE: DNA
<213> ORGANISM: Artificial sequence
<220> FEATURE:
<223> OTHER INFORMATION: primer

<400> SEQUENCE: 48
gaattcgatg tacaacttca gg                                             22

<210> SEQ ID NO 49
<211> LENGTH: 54
```

```
<212> TYPE: DNA
<213> ORGANISM: Artificial sequence
<220> FEATURE:
<223> OTHER INFORMATION: primer

<400> SEQUENCE: 49
gctaccaccc cctccagatc cgccacctcc tgaagatacg gtgaccgtgg tgcc        54

<210> SEQ ID NO 50
<211> LENGTH: 52
<212> TYPE: DNA
<213> ORGANISM: Artificial sequence
<220> FEATURE:
<223> OTHER INFORMATION: primer

<400> SEQUENCE: 50
atctggaggg ggtggtagcg gtggaggcgg gagtgacatc cagatgactc ag          52

<210> SEQ ID NO 51
<211> LENGTH: 22
<212> TYPE: DNA
<213> ORGANISM: Artificial sequence
<220> FEATURE:
<223> OTHER INFORMATION: primer

<400> SEQUENCE: 51
gtcgacccgt ttgatttcca gc                                           22

<210> SEQ ID NO 52
<211> LENGTH: 30
<212> TYPE: DNA
<213> ORGANISM: Artificial sequence
<220> FEATURE:
<223> OTHER INFORMATION: primer

<400> SEQUENCE: 52
cccaagctta ctggatggtg ggaagatgga                                   30

<210> SEQ ID NO 53
<211> LENGTH: 24
<212> TYPE: DNA
<213> ORGANISM: Artificial sequence
<220> FEATURE:
<223> OTHER INFORMATION: peptide

<400> SEQUENCE: 53
actagtacaa tccctgggca caat                                         24

<210> SEQ ID NO 54
<211> LENGTH: 24
<212> TYPE: DNA
<213> ORGANISM: Artificial sequence
<220> FEATURE:
<223> OTHER INFORMATION: peptide

<400> SEQUENCE: 54
actagtcttg ggtattctag gctc                                         24

<210> SEQ ID NO 55
<211> LENGTH: 36
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (11)..(11)
```

```
<223> OTHER INFORMATION: n is a or g
<220> FEATURE:
<221> NAME/KEY: misc_feature
<222> LOCATION: (23)..(23)
<223> OTHER INFORMATION: n is a or t
<220> FEATURE:
<221> NAME/KEY: misc_feature
<222> LOCATION: (26)..(26)
<223> OTHER INFORMATION: n is c or t
<220> FEATURE:
<221> NAME/KEY: misc_feature
<222> LOCATION: (31)..(31)
<223> OTHER INFORMATION: n is a, c, t or g
<220> FEATURE:
<221> NAME/KEY: misc_feature
<222> LOCATION: (32)..(32)
<223> OTHER INFORMATION: n is a or t

<400> SEQUENCE: 55
cgacatgagg ncccctgctc agnttnttgg nntctt                                36

<210> SEQ ID NO 56
<211> LENGTH: 30
<212> TYPE: DNA
<213> ORGANISM: Artificial sequence
<220> FEATURE:
<223> OTHER INFORMATION: primer

<400> SEQUENCE: 56
ggatcccata tgcaggttac tctgaaagag                                       30

<210> SEQ ID NO 57
<211> LENGTH: 48
<212> TYPE: DNA
<213> ORGANISM: Artificial sequence
<220> FEATURE:
<223> OTHER INFORMATION: primer

<400> SEQUENCE: 57
gctaccaccc cctccagatc cgccacctcc tgaggagacg gcgactga                   48

<210> SEQ ID NO 58
<211> LENGTH: 52
<212> TYPE: DNA
<213> ORGANISM: Artificial sequence
<220> FEATURE:
<223> OTHER INFORMATION: primer

<400> SEQUENCE: 58
atctggaggg ggtggtagcg gtggaggcgg gagtgacatc cagatgactc ag              52

<210> SEQ ID NO 59
<211> LENGTH: 26
<212> TYPE: DNA
<213> ORGANISM: Artificial sequence
<220> FEATURE:
<223> OTHER INFORMATION: primer

<400> SEQUENCE: 59
gtcgacccgt ttgatttcca gcttgg                                           26

<210> SEQ ID NO 60
<211> LENGTH: 31
<212> TYPE: DNA
<213> ORGANISM: Artificial sequence
<220> FEATURE:
<223> OTHER INFORMATION: primer
<220> FEATURE:
<221> NAME/KEY: misc_feature
```

```
<222> LOCATION: (10)..(10)
<223> OTHER INFORMATION: n is c or t
<220> FEATURE:
<221> NAME/KEY: misc_feature
<222> LOCATION: (13)..(13)
<223> OTHER INFORMATION: n is c or t
<220> FEATURE:
<221> NAME/KEY: misc_feature
<222> LOCATION: (16)..(16)
<223> OTHER INFORMATION: n is a, c, or g

<400> SEQUENCE: 60
cgacatggtn ctnatntcct tgctgttctg g                           31

<210> SEQ ID NO 61
<211> LENGTH: 30
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (14)..(14)
<223> OTHER INFORMATION: n is c or t
<220> FEATURE:
<221> NAME/KEY: misc_feature
<222> LOCATION: (16)..(16)
<223> OTHER INFORMATION: n is a or g
<220> FEATURE:
<221> NAME/KEY: misc_feature
<222> LOCATION: (18)..(18)
<223> OTHER INFORMATION: n is c, g, or t
<220> FEATURE:
<221> NAME/KEY: misc_feature
<222> LOCATION: (23)..(23)
<223> OTHER INFORMATION: n is c or t
<220> FEATURE:
<221> NAME/KEY: misc_feature
<222> LOCATION: (26)..(26)
<223> OTHER INFORMATION: n is c or t

<400> SEQUENCE: 61
cgacatggct gtcntngngc tgntcntctg                             30

<210> SEQ ID NO 62
<211> LENGTH: 33
<212> TYPE: DNA
<213> ORGANISM: Artificial sequence
<220> FEATURE:
<223> OTHER INFORMATION: primer

<400> SEQUENCE: 62
cgacatgaag ttgcctgtta ggctgttggt gct                         33

<210> SEQ ID NO 63
<211> LENGTH: 29
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n is a or g
<220> FEATURE:
<221> NAME/KEY: misc_feature
<222> LOCATION: (15)..(15)
<223> OTHER INFORMATION: n is c or g
<220> FEATURE:
<221> NAME/KEY: misc_feature
<222> LOCATION: (17)..(17)
<223> OTHER INFORMATION: n is t or g
<220> FEATURE:
```

```
<221> NAME/KEY: misc_feature
<222> LOCATION: (18)..(18)
<223> OTHER INFORMATION: n is t or g
<220> FEATURE:
<221> NAME/KEY: misc_feature
<222> LOCATION: (19)..(19)
<223> OTHER INFORMATION: n is a, c, t, or g
<220> FEATURE:
<221> NAME/KEY: misc_feature
<222> LOCATION: (20)..(20)
<223> OTHER INFORMATION: n is a or g
<220> FEATURE:
<221> NAME/KEY: misc_feature
<222> LOCATION: (26)..(26)
<223> OTHER INFORMATION: n is a or C

<400> SEQUENCE: 63
cgacatggna tggancnnnn tctttntct                                29

<210> SEQ ID NO 64
<211> LENGTH: 23
<212> TYPE: DNA
<213> ORGANISM: Artificial sequence
<220> FEATURE:
<223> OTHER INFORMATION: primer

<400> SEQUENCE: 64
ctcgagactg tggctgcacc atc                                      23

<210> SEQ ID NO 65
<211> LENGTH: 31
<212> TYPE: DNA
<213> ORGANISM: Artificial sequence
<220> FEATURE:
<223> OTHER INFORMATION: primer

<400> SEQUENCE: 65
ggatcctcta gattaacact ctccctgtt g                              31

<210> SEQ ID NO 66
<211> LENGTH: 22
<212> TYPE: DNA
<213> ORGANISM: Artificial sequence
<220> FEATURE:
<223> OTHER INFORMATION: primer

<400> SEQUENCE: 66
ctcgaggcaa gcttcaaggg cc                                       22

<210> SEQ ID NO 67
<211> LENGTH: 31
<212> TYPE: DNA
<213> ORGANISM: Artificial sequence
<220> FEATURE:
<223> OTHER INFORMATION: primer

<400> SEQUENCE: 67
ggatcctcta gattatttac ccggagacag g                             31

<210> SEQ ID NO 68
<211> LENGTH: 84
<212> TYPE: DNA
<213> ORGANISM: Artificial sequence
<220> FEATURE:
<223> OTHER INFORMATION: primer

<400> SEQUENCE: 68
gaattcatga gtgtgcccac tcaggtcctg gggttgctgc tgctgtggct tacagatgcc     60
```

```
agatgtgaca tccagatgac tcag                                              84

<210> SEQ ID NO 69
<211> LENGTH: 26
<212> TYPE: DNA
<213> ORGANISM: Artificial sequence
<220> FEATURE:
<223> OTHER INFORMATION: primer

<400> SEQUENCE: 69
ctcgagccgt tgatttcca gcttgg                                             26

<210> SEQ ID NO 70
<211> LENGTH: 89
<212> TYPE: DNA
<213> ORGANISM: Artificial sequence
<220> FEATURE:
<223> OTHER INFORMATION: primer

<400> SEQUENCE: 70
gaattcagat ctatgggcag gcttacttct tcattcctgc tactgattgt ccctgcatat       60
gtcctgtccc aggttactct gaaagagtc                                         89

<210> SEQ ID NO 71
<211> LENGTH: 23
<212> TYPE: DNA
<213> ORGANISM: Artificial sequence
<220> FEATURE:
<223> OTHER INFORMATION: primer

<400> SEQUENCE: 71
ctcgagtgag gagacggcga ctg                                               23

<210> SEQ ID NO 72
<211> LENGTH: 36
<212> TYPE: DNA
<213> ORGANISM: Artificial sequence
<220> FEATURE:
<223> OTHER INFORMATION: primer

<400> SEQUENCE: 72
catatgtcgg cgggtggtca gctgttctac tctcgc                                 36

<210> SEQ ID NO 73
<211> LENGTH: 49
<212> TYPE: DNA
<213> ORGANISM: Artificial sequence
<220> FEATURE:
<223> OTHER INFORMATION: primer

<400> SEQUENCE: 73
catatgctag gcggtctacc cacagaattg atttcgtcgg cgggtggtc                   49

<210> SEQ ID NO 74
<211> LENGTH: 58
<212> TYPE: DNA
<213> ORGANISM: Artificial sequence
<220> FEATURE:
<223> OTHER INFORMATION: primer

<400> SEQUENCE: 74
catatgatag cgcttaccct gtttaacctt gctgacaccc tgctaggcgg tctaccca         58

<210> SEQ ID NO 75
```

```
<211> LENGTH: 33
<212> TYPE: DNA
<213> ORGANISM: Artificial sequence
<220> FEATURE:
<223> OTHER INFORMATION: primer

<400> SEQUENCE: 75
gaattcacca ccatgatagc gcttaccctg ttt                               33

<210> SEQ ID NO 76
<211> LENGTH: 7
<212> TYPE: PRT
<213> ORGANISM: Artificial
<220> FEATURE:
<223> OTHER INFORMATION: synthetic peptide

<400> SEQUENCE: 76

His Ala Ile Tyr Pro Arg His
1               5

<210> SEQ ID NO 77
<211> LENGTH: 7
<212> TYPE: PRT
<213> ORGANISM: Artificial
<220> FEATURE:
<223> OTHER INFORMATION: synthetic peptide

<400> SEQUENCE: 77

His Trp Gly Met Trp Ser Tyr
1               5

<210> SEQ ID NO 78
<211> LENGTH: 7
<212> TYPE: PRT
<213> ORGANISM: Artificial
<220> FEATURE:
<223> OTHER INFORMATION: synthetic peptide

<400> SEQUENCE: 78

Pro Val Gln Met Pro Trp Leu
1               5

<210> SEQ ID NO 79
<211> LENGTH: 7
<212> TYPE: PRT
<213> ORGANISM: Artificial
<220> FEATURE:
<223> OTHER INFORMATION: synthetic peptide

<400> SEQUENCE: 79

Ile Thr Asn Asp Phe Lys Gln
1               5

<210> SEQ ID NO 80
<211> LENGTH: 7
<212> TYPE: PRT
<213> ORGANISM: Artificial
<220> FEATURE:
<223> OTHER INFORMATION: synthetic peptide

<400> SEQUENCE: 80

Ser Leu Pro Thr Leu Thr Leu
1               5

<210> SEQ ID NO 81
<211> LENGTH: 7
<212> TYPE: PRT
```

```
<213> ORGANISM: Artificial
<220> FEATURE:
<223> OTHER INFORMATION: synthetic peptide

<400> SEQUENCE: 81

Ser Thr Leu Phe Met Asn Phe
1               5

<210> SEQ ID NO 82
<211> LENGTH: 7
<212> TYPE: PRT
<213> ORGANISM: Artificial
<220> FEATURE:
<223> OTHER INFORMATION: synthetic peptide

<400> SEQUENCE: 82

Ser Ala His Val Leu Ser Thr
1               5

<210> SEQ ID NO 83
<211> LENGTH: 7
<212> TYPE: PRT
<213> ORGANISM: Artificial
<220> FEATURE:
<223> OTHER INFORMATION: synthetic peptide

<400> SEQUENCE: 83

Ser Pro Pro Asn Val Arg Thr
1               5

<210> SEQ ID NO 84
<211> LENGTH: 7
<212> TYPE: PRT
<213> ORGANISM: Artificial
<220> FEATURE:
<223> OTHER INFORMATION: synthetic peptide

<400> SEQUENCE: 84

Ser Pro Lys Met Pro Ile Leu
1               5

<210> SEQ ID NO 85
<211> LENGTH: 7
<212> TYPE: PRT
<213> ORGANISM: Artificial
<220> FEATURE:
<223> OTHER INFORMATION: synthetic peptide

<400> SEQUENCE: 85

Phe Ser Tyr Leu Pro Ser His
1               5

<210> SEQ ID NO 86
<211> LENGTH: 7
<212> TYPE: PRT
<213> ORGANISM: Artificial
<220> FEATURE:
<223> OTHER INFORMATION: synthetic peptide

<400> SEQUENCE: 86

Val Ser Trp Asn Ser Leu Val
1               5

<210> SEQ ID NO 87
<211> LENGTH: 7
<212> TYPE: PRT
<213> ORGANISM: Artificial
```

```
<220> FEATURE:
<223> OTHER INFORMATION: synthetic peptide

<400> SEQUENCE: 87

Tyr Gln Asp Ser Ala Lys Thr
1               5

<210> SEQ ID NO 88
<211> LENGTH: 7
<212> TYPE: PRT
<213> ORGANISM: Artificial
<220> FEATURE:
<223> OTHER INFORMATION: synthetic peptide

<400> SEQUENCE: 88

Thr Tyr Leu Pro Trp Pro Ala
1               5

<210> SEQ ID NO 89
<211> LENGTH: 7
<212> TYPE: PRT
<213> ORGANISM: Artificial
<220> FEATURE:
<223> OTHER INFORMATION: synthetic protein

<400> SEQUENCE: 89

Asn His Trp Ala Ser Pro Arg
1               5

<210> SEQ ID NO 90
<211> LENGTH: 7
<212> TYPE: PRT
<213> ORGANISM: Artificial
<220> FEATURE:
<223> OTHER INFORMATION: synthetic peptide

<400> SEQUENCE: 90

Ser Ser Tyr Glu Trp Phe Ile
1               5

<210> SEQ ID NO 91
<211> LENGTH: 7
<212> TYPE: PRT
<213> ORGANISM: Artificial
<220> FEATURE:
<223> OTHER INFORMATION: synthetic peptide

<400> SEQUENCE: 91

Ser Ala Pro Ser Ser Lys Asn
1               5

<210> SEQ ID NO 92
<211> LENGTH: 7
<212> TYPE: PRT
<213> ORGANISM: Artificial
<220> FEATURE:
<223> OTHER INFORMATION: synthetic peptide

<400> SEQUENCE: 92

Ile Asn Gln Lys Pro Thr Leu
1               5

<210> SEQ ID NO 93
<211> LENGTH: 7
<212> TYPE: PRT
<213> ORGANISM: Artificial
<220> FEATURE:
```

<223> OTHER INFORMATION: synthetic peptide

<400> SEQUENCE: 93

Ser Ser Met Phe Phe Tyr Arg
1               5

<210> SEQ ID NO 94
<211> LENGTH: 7
<212> TYPE: PRT
<213> ORGANISM: Artificial
<220> FEATURE:
<223> OTHER INFORMATION: synthetic peptide

<400> SEQUENCE: 94

Ser Leu Val Thr Gly Ile Leu
1               5

<210> SEQ ID NO 95
<211> LENGTH: 7
<212> TYPE: PRT
<213> ORGANISM: Artificial
<220> FEATURE:
<223> OTHER INFORMATION: synthetic peptide

<400> SEQUENCE: 95

Thr Asn Leu Arg Leu Asp Ser
1               5

<210> SEQ ID NO 96
<211> LENGTH: 7
<212> TYPE: PRT
<213> ORGANISM: Artificial
<220> FEATURE:
<223> OTHER INFORMATION: synthetic peptide

<400> SEQUENCE: 96

Tyr Gln Asp Ser Ala Lys Thr
1               5

<210> SEQ ID NO 97
<211> LENGTH: 7
<212> TYPE: PRT
<213> ORGANISM: Artificial
<220> FEATURE:
<223> OTHER INFORMATION: synthetic peptide

<400> SEQUENCE: 97

Met Leu Trp Gly Pro Ser Asp
1               5

<210> SEQ ID NO 98
<211> LENGTH: 7
<212> TYPE: PRT
<213> ORGANISM: Artificial
<220> FEATURE:
<223> OTHER INFORMATION: synthetic peptide

<400> SEQUENCE: 98

Gln Pro Ala Thr Trp Asn Thr
1               5

<210> SEQ ID NO 99
<211> LENGTH: 7
<212> TYPE: PRT
<213> ORGANISM: Artificial
<220> FEATURE:
<223> OTHER INFORMATION: synthetic peptide

```
<400> SEQUENCE: 99

Gly Gly Trp Gly Pro Phe Ala
1               5

<210> SEQ ID NO 100
<211> LENGTH: 7
<212> TYPE: PRT
<213> ORGANISM: Artificial
<220> FEATURE:
<223> OTHER INFORMATION: synthetic peptide

<400> SEQUENCE: 100

Ala Leu Trp Gly Pro Thr Ser
1               5

<210> SEQ ID NO 101
<211> LENGTH: 24
<212> TYPE: DNA
<213> ORGANISM: Artificial sequence
<220> FEATURE:
<223> OTHER INFORMATION: primer

<400> SEQUENCE: 101
ggatcccata tggacattga ccca                                          24

<210> SEQ ID NO 102
<211> LENGTH: 27
<212> TYPE: DNA
<213> ORGANISM: Artificial sequence
<220> FEATURE:
<223> OTHER INFORMATION: primer

<400> SEQUENCE: 102
gaattcttaa acaacagtag tttccgg                                       27

<210> SEQ ID NO 103
<211> LENGTH: 59
<212> TYPE: DNA
<213> ORGANISM: Artificial sequence
<220> FEATURE:
<223> OTHER INFORMATION: primer

<400> SEQUENCE: 103
gtggtactgg atccggtggt ggaggttcag gaggaggtgg ttccagggaa ttagtagtc    59

<210> SEQ ID NO 104
<211> LENGTH: 56
<212> TYPE: DNA
<213> ORGANISM: Artificial sequence
<220> FEATURE:
<223> OTHER INFORMATION: primer

<400> SEQUENCE: 104
ccggatccag taccaccacc tccagaacca cctccaccat cttccaaatt acttcc       56

<210> SEQ ID NO 105
<211> LENGTH: 23
<212> TYPE: DNA
<213> ORGANISM: Artificial sequence
<220> FEATURE:
<223> OTHER INFORMATION: primer

<400> SEQUENCE: 105
gaattcttaa acaacagtag ttt                                           23
```

```
<210> SEQ ID NO 106
<211> LENGTH: 44
<212> TYPE: DNA
<213> ORGANISM: Artificial sequence
<220> FEATURE:
<223> OTHER INFORMATION: primer

<400> SEQUENCE: 106
ggatcccatc ctactctttt gcgtattggt ggtggaggtt cagg            44

<210> SEQ ID NO 107
<211> LENGTH: 44
<212> TYPE: DNA
<213> ORGANISM: Artificial sequence
<220> FEATURE:
<223> OTHER INFORMATION: primer

<400> SEQUENCE: 107
ggatcctcta ttctgccgta tccttatggt ggtggaggtt cagg            44
```